United States Patent
Deretic et al.

(10) Patent No.: US 11,819,498 B2
(45) Date of Patent: Nov. 21, 2023

(54) METHODS AND COMPOSITIONS FOR TREATING AUTOPHAGY RELATED DISEASE STATES AND CONDITIONS UTILIZING AMPK ACTIVATION

(71) Applicant: UNM RAINFOREST INNOVATIONS, Albuquerque, NM (US)

(72) Inventors: Vojo P. Deretic, Placitas, NM (US); Jia Cassano, Albuquerque, NM (US); Bhawana Bissa, Albuquerque, NM (US)

(73) Assignee: UNM RAINFOREST INNOVATIONS, Albuquerque, NM (US)

( * ) Notice: Subject to any disclaimer, the term of this patent is extended or adjusted under 35 U.S.C. 154(b) by 88 days.

(21) Appl. No.: 17/136,608

(22) Filed: Dec. 29, 2020

(65) Prior Publication Data

US 2021/0205286 A1    Jul. 8, 2021

Related U.S. Application Data

(60) Provisional application No. 62/977,944, filed on Feb. 18, 2020, provisional application No. 62/955,255, filed on Dec. 30, 2019.

(51) Int. Cl.
| | |
|---|---|
| *A61K 31/4164* | (2006.01) |
| *A61K 31/4184* | (2006.01) |
| *A61K 31/438* | (2006.01) |
| *A61K 31/133* | (2006.01) |
| *A61K 31/198* | (2006.01) |
| *A61K 31/155* | (2006.01) |
| *A61K 31/4439* | (2006.01) |
| *A61K 31/585* | (2006.01) |
| *A61K 31/7004* | (2006.01) |
| *A61K 31/618* | (2006.01) |
| *A61K 31/4365* | (2006.01) |
| *A61K 31/496* | (2006.01) |
| *A61K 31/519* | (2006.01) |
| *A61K 31/437* | (2006.01) |
| *A61K 31/485* | (2006.01) |
| *A61K 31/4545* | (2006.01) |
| *A61K 31/4418* | (2006.01) |
| *A61K 31/192* | (2006.01) |
| *A61K 31/58* | (2006.01) |
| *A61K 31/365* | (2006.01) |

(52) U.S. Cl.
CPC ........ *A61K 31/4439* (2013.01); *A61K 31/133* (2013.01); *A61K 31/155* (2013.01); *A61K 31/192* (2013.01); *A61K 31/198* (2013.01); *A61K 31/365* (2013.01); *A61K 31/4164* (2013.01); *A61K 31/4184* (2013.01); *A61K 31/437* (2013.01); *A61K 31/438* (2013.01); *A61K 31/4365* (2013.01); *A61K 31/4418* (2013.01); *A61K 31/4545* (2013.01); *A61K 31/485* (2013.01); *A61K 31/496* (2013.01); *A61K 31/519* (2013.01); *A61K 31/58* (2013.01); *A61K 31/585* (2013.01); *A61K 31/618* (2013.01); *A61K 31/7004* (2013.01)

(58) Field of Classification Search
CPC .. A61K 31/155; A61K 31/198; A61K 31/133; A61K 31/4164; A61K 31/4184; A61K 31/438; A61P 31/06
See application file for complete search history.

(56) References Cited

PUBLICATIONS

Yew et al., Tuberculosis, 2019, 115, p. 76-80, Available online Feb. 13, 2019. (Year: 2019).*
Nakahira et al., Am. J. Physiol. Lung Cell Mol. Physiol., 2013, 305, p. L93-L107. (Year: 2013).*
Li et al., FEBS Letters, 2000, 470, p. 35-39. (Year: 2000).*
Jia J; et al. AMPK, a Regulator of Metabolism and Autophagy, Is Activated by Lysosomal Damage via a Novel Galectin-Directed Ubiquitin Signal Transduction System. Molecular Cell, 2020;77:1-19.
Jia J; et al. Galectin-3 Coordinates a Cellular System for Lysosomal Repair and Removal. Developmental Cell, 2020;52:1-19.

* cited by examiner

*Primary Examiner* — Jonathan S Lau
(74) *Attorney, Agent, or Firm* — Henry D. Coleman; R. Neil Sudol

(57) ABSTRACT

The present invention is directed to the discovery that AMPK activation through Galectin 9 induces autophagy and affects other related processes in response to lyosomal damage which occurs and the use of that mechanism in the treatment of autophagy disease states and/or conditions. The use of modulators of AMPK and optionally a modulator of Galectin 9, TAK1 and/or a lysosomotropic agent for the treatment of autophagy-mediated disease states and/or conditions is described as are pharmaceutical compositions.

3 Claims, 18 Drawing Sheets

Specification includes a Sequence Listing.

FIGURE S6
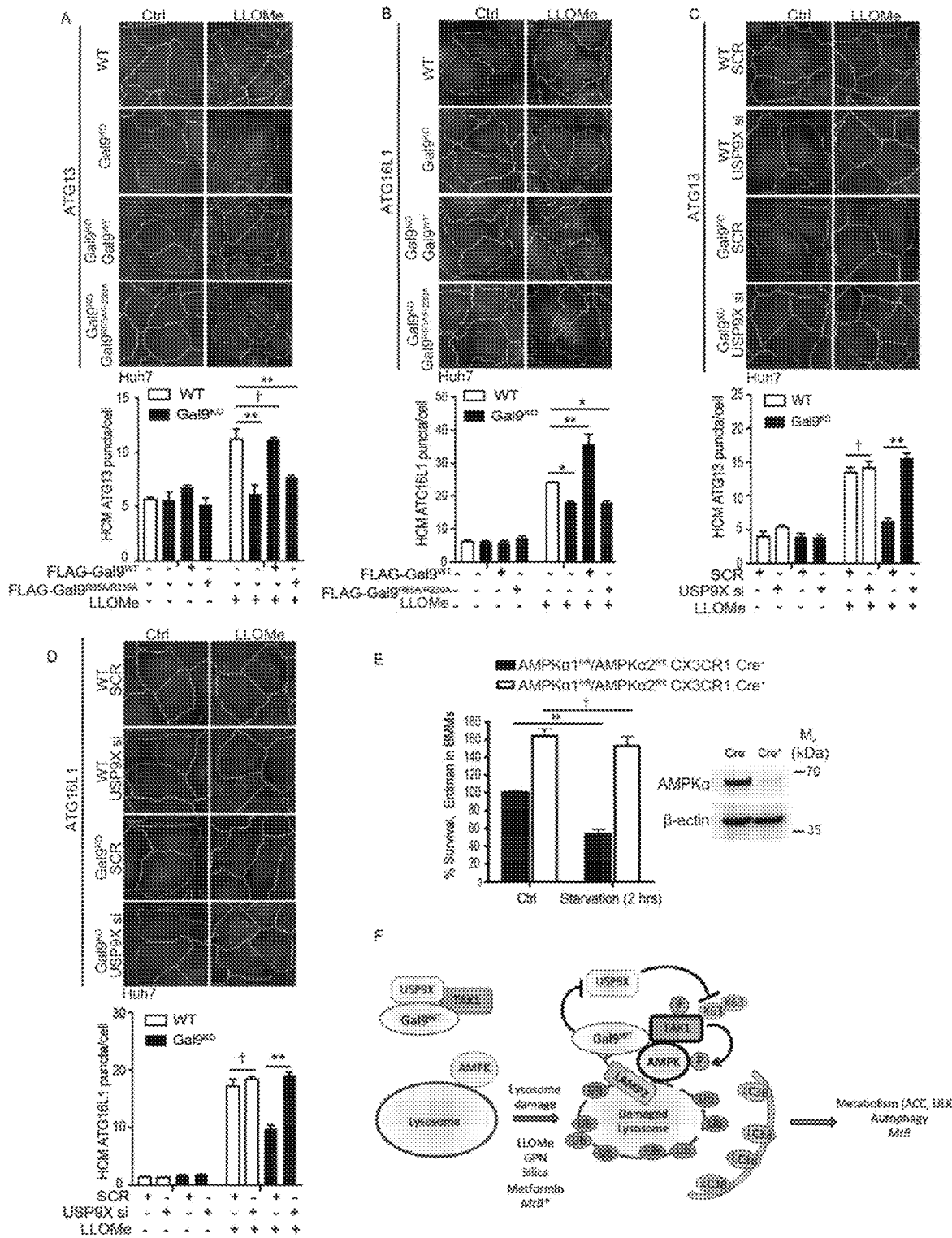

SEQUENCE LISTING

```
<160> NUMBER OF SEQ ID NOS: 3

<210> SEQ ID NO 1
<211> LENGTH: 355
<212> TYPE: PRT
<213> ORGANISM: Homo sapiens

<400> SEQUENCE: 1

Met Ala Phe Ser Gly Ser Gln Ala Pro Tyr Leu Ser Pro Ala Val Pro
1               5                   10                  15

Phe Ser Gly Thr Ile Gln Gly Gly Leu Gln Asp Gly Leu Gln Ile Thr
            20                  25                  30

Val Asn Gly Thr Val Leu Ser Ser Ser Gly Thr Arg Phe Ala Val Asn
        35                  40                  45

Phe Gln Thr Gly Phe Ser Gly Asn Asp Ile Ala Phe His Phe Asn Pro
    50                  55                  60

Arg Phe Glu Asp Gly Gly Tyr Val Val Cys Asn Thr Arg Gln Asn Gly
65                  70                  75                  80

Ser Trp Gly Pro Glu Glu Arg Lys Thr His Met Pro Phe Gln Lys Gly
                85                  90                  95

Met Pro Phe Asp Leu Cys Phe Leu Val Gln Ser Ser Asp Phe Lys Val
            100                 105                 110

Met Val Asn Gly Ile Leu Phe Val Gln Tyr Phe His Arg Val Pro Phe
        115                 120                 125

His Arg Val Asp Thr Ile Ser Val Asn Gly Ser Val Gln Leu Ser Tyr
    130                 135                 140

Ile Ser Phe Gln Asn Pro Arg Thr Val Pro Val Gln Pro Ala Phe Ser
145                 150                 155                 160

Thr Val Pro Phe Ser Gln Pro Val Cys Phe Pro Pro Arg Pro Arg Gly
                165                 170                 175

Arg Arg Gln Lys Pro Pro Gly Val Trp Pro Ala Asn Pro Ala Pro Ile
            180                 185                 190

Thr Gln Thr Val Ile His Thr Val Gln Ser Ala Pro Gly Gln Met Phe
        195                 200                 205

Ser Thr Pro Ala Ile Pro Pro Met Met Tyr Pro His Pro Ala Tyr Pro
    210                 215                 220
```

```
Met Pro Phe Ile Thr Thr Ile Leu Gly Gly Leu Tyr Pro Ser Lys Ser
225                 230                 235                 240

Ile Leu Leu Ser Gly Thr Val Leu Pro Ser Ala Gln Arg Phe His Ile
                245                 250                 255

Asn Leu Cys Ser Gly Asn His Ile Ala Phe His Leu Asn Pro Arg Phe
            260                 265                 270

Asp Glu Asn Ala Val Val Arg Asn Thr Gln Ile Asp Asn Ser Trp Gly
        275                 280                 285

Ser Glu Glu Arg Ser Leu Pro Arg Lys Met Pro Phe Val Arg Gly Gln
    290                 295                 300

Ser Phe Ser Val Trp Ile Leu Cys Glu Ala His Cys Leu Lys Val Ala
305                 310                 315                 320

Val Asp Gly Gln His Leu Phe Glu Tyr Tyr His Arg Leu Arg Asn Leu
                325                 330                 335

Pro Thr Ile Asn Arg Leu Glu Val Gly Gly Asp Ile Gln Leu Thr His
            340                 345                 350

Val Gln Thr
        355

<210> SEQ ID NO 2
<211> LENGTH: 20
<212> TYPE: DNA
<213> ORGANISM: Homo sapiens

<400> SEQUENCE: 2
acacacacac ctggttccac                                               20

<210> SEQ ID NO 3
<211> LENGTH: 77
<212> TYPE: DNA
<213> ORGANISM: Homo sapiens

<400> SEQUENCE: 3
actgtcaatg ggaccgttct cagctccagt ggaaccaggt gtgtgtgtat atggatggaa    60
acgtttcact ccagcct                                                  77
```

METHODS AND COMPOSITIONS FOR TREATING AUTOPHAGY RELATED DISEASE STATES AND CONDITIONS UTILIZING AMPK ACTIVATION

RELATED APPLICATIONS AND GRANT SUPPORT

This application claims the benefit of priority of provisional application Ser. Nos. 62/955,255, filed Dec. 30, 2019 and 62/977,944, filed Feb. 18, 2020, the entire contents of said applications being incorporated by reference in their entireties herein.

This invention was made with government support under grant nos. P20 GM121176, RO1 AI042999 and R37 AI042999, awarded by the National Institutes of Health. The government has certain rights in the invention.

FIELD OF THE INVENTION

The present invention is directed to the discovery that adenosine 5' monophosphate-activated protein kinase (AMPK) activation through Galectin 9 induces autophagy and affects other related processes in response to lyosomal damage which occurs and the use of that mechanism in the treatment of autophagy disease states and/or conditions. This invention relates to the use of AMPK modulators (agonists or antagonists) alone or in combination with other agents for the treatment of autophagy related disease states and/or disorders.

BACKGROUND AND OVERVIEW OF THE INVENTION

Autophagy is a cellular degradation pathway that contributes to metabolic homeostasis as well as ensures quality control. AMPK is a known regulator of autophagy and recently we have reported that lysosomal damage activates AMPK. However, the molecular and cellular details of how AMPK activation occurs in response to lysosomal damage and how this in turn modulates autophagy are not known.

AMP-activated protein kinase (AMPK) is a ubiquitous metabolic regulator in eukaryotes (Hardie, 2014) acting as a cellular energy sensor and as a keeper of homeostatic levels of ATP (Herzig and Shaw, 2018; Lin and Hardie, 2018). Activation of AMPK results in inhibition of anabolic pathways that consume ATP and activation of catabolic pathways that generate ATP, reprograming cellular metabolism to preserve and restore energy balance (Hardie, 2014). Although the best known effects of AMPK are on intermediary metabolism (Hardie, 2014), AMPK has global functions (Herzig and Shaw, 2018; Lin and Hardie, 2018), including cell cycle, proliferation and senescence (Jones et al., 2005), transcriptional activation of mitochondrial biogenesis (Jager et al., 2007), cell polarity (Lee et al., 2007) and autophagy (Egan et al., 2011; Garcia and Shaw, 2017; Herrero-Martin et al., 2009a; Kim et al., 2013; Kim et al., 2011).

AMPK's role in metabolic reprogramming, along with the action of its polar opposite, mTOR, which activates anabolic pathways (Saxton and Sabatini, 2017), have been implicated in disease states with major metabolic perturbations (Garcia and Shaw, 2017) such as diabetes (He and Wondisford, 2015; Zhou et al., 2001) and cancer (Pineda et al., 2015). AMPK is also an important modulator of the immune system, with immunometabolism being increasingly recognized as an important determinant of innate and adaptive immune responses (Gaber et al., 2017; O'Neill et al., 2016). By their opposing actions during immunometabolic switching, AMPK and mTOR influence innate and adaptive immunity responses (Gaber et al., 2017; O'Neill et al., 2016). AMPK (Egan et al., 2011; Garcia and Shaw, 2017; Herrero-Martin et al., 2009a; Herzig and Shaw, 2018; Kim et al., 2013; Kim et al., 2011) and mTOR (Ganley et al., 2009; Hosokawa et al., 2009; Jung et al., 2009; Saxton and Sabatini, 2017) together control autophagy (Levine and Kroemer, 2019), a versatile homeostatic process with roles in aging (Hansen et al., 2018; Madeo et al., 2019), obesity (Zhang et al., 2018), diabetes (Rivera et al., 2014), cancer (Kimmelman and White, 2017), immunity, inflammation and cell-autonomous defense against intracellular pathogens (Deretic et al., 2013), neurodegenerative and other diseases (Levine and Kroemer, 2019; Mizushima et al., 2008; Rubinsztein et al., 2015).

Distinctively, autophagy plays a dual role as a metabolic process (Kimmelman and White, 2017; Kopitz et al., 1990; Rabinowitz and White, 2010) and as a cytoplasmic quality control (QC) pathway (Dikic and Elazar, 2018; Randow and Youle, 2014; Rogov et al., 2014). Autophagy's metabolic contributions are manifested as starvation-induced turn-over of bulk cytosolic proteins (Abu-Remaileh et al., 2017; Kopitz et al., 1990; Seglen et al., 1990) and degradation of ribosomes as major cellular reservoirs of basic amino acids and nucleosides (An and Harper, 2018; Wyant et al., 2018). In addition, autophagy acts in mobilization and catabolism of lipids (Dupont et al., 2014; Kopitz et al., 1990; Rambold et al., 2015; Seo et al., 2017: Settembre et al., 2013; Singh et al., 2009) and glycogen (Zirin et al., 2013). The QC functions of autophagy are manifested in selective removal of defunct or surplus organelles such as mitochondria (Lazarou et al., 2015), ER (Khaminets et al., 2015), peroxisomes (Marcassa et al., 2018), protein aggregates (Bjorkoy et al., 2005; Dikic and Elazar, 2018; Rogov et al., 2014) and damaged lysosomes (Maejima et al., 2013). When autophagy acts as an innate defense against invading microbes, this too falls under the rubric of cytoplasmic QC (Deretic et al., 2013).

Lysosomal damage strongly induces autophagy exceeding starvation as induction benchmark (Chauhan et al., 2016; Jia et al., 2018). Autophagy acts to remove damaged lysosomes (Maejima et al., 2013) once they are beyond repair (Radulovic et al., 2018; Skowyra et al., 2018). The complexity of the relationship between autophagy and lysosomes is that autophagosomal and endolysosomal organelles merge during the final steps of autophagy so that the sequestered autophagic cargo can be digested in autolysosomes or otherwise eliminated (Levine and Kroemer, 2019). Thus, lysosomal homeostasis and maintenance (Radulovic et al., 2018; Skowyra et al., 2018), including their reformation (Yu et al., 2010) and de novo biogenesis (Sardiello et al., 2009; Settembre et al., 2011) is of a paramount importance for cellular capacity to maintain functional autophagy. Hence, countering lysosomal injury, via membrane repair (Radulovic et al., 2018; Skowyra et al., 2018) or elimination of damaged lysosomes (lysophagy) (Maejima et al., 2013) coupled with their replacement through biogenesis (Sardiello et al., 2009; Settembre et al., 2011), is necessary for cellular fitness. Lysosome damage occurs physiologically, e.g. during exposure to exogenous and endogenous agents including biologically active crystals of silica, monosodium urate, and cholesterol (Maejima et al., 2013; Razani et al., 2012; Schroder and Tschopp, 2010), proteopathic fibrils/amyloid (Heneka et al., 2013; Masters et al., 2010; Papadopoulos et al., 2017; Parry et al., 2015), and microbial invasion involving directly or indirectly lysosomal compartments (Fujita et al., 2013; Jia et al., 2018; Maejima et al., 2013).

AMPK can be activated by different stressors that alter cellular energy levels including glucose starvation, hypoxia, ischemia, and oxidative damage (Hardie, 2011; Herzig and Shaw, 2018; Lin and Hardie, 2018). In the majority of these processes. AMPK subunits react to reduced cellular energy charge (e.g. increased AMP:ATP ratios). However, AMPK can be activated by nucleotide-independent mechanisms (Lin and Hardie, 2018) whereby the absence of a specific glycolytic intermediate, fructose 1,6 bisphosphate (FBP), triggers AMPK activation on lysosomes (Li et al., 2019; Zhang et al., 2017). Whether other signals activating AMPK utilize this new or other yet to be uncovered pathways is not known. There are three upstream kinases, LKB1 (Woods et al., 2003). CAMKK2 (Hawley et al., 2005) and TAK1 (Momcilovic et al., 2006) that can activate AMPK by phosphorylation at T172. LKB1 is considered to be the dominant AMPK kinase (Hardie, 2014; Herzig and Shaw, 2018; Lin and Hardie, 2018). CAMKK2 is a well-accepted alternative AMPK kinase contributing to AMPK's responses to various physiological conditions; a residual response of AMPK in tumors lacking LKB1 is often attributed to CAMMK2 (Herzig and Shaw, 2018). TAK1 is a less prominent T172 kinase of AMPK still in a search of its true physiological role in AMPK activation (Neumann, 2018). TAK1 can activate AMPK under diverse conditions (Chen et al., 2013; Herrero-Martin et al., 2009a, b; Jing et al., 2015; Lee et al., 2010; Xie et al., 2006; Zippel et al., 2013), including bacterial infection (Liu et al., 2018). Importantly, activation of TAK1 does not always lead to AMPK activation (Herrero-Martin et al., 2009a), and thus whether AMPK is activated by TAK1 likely depends on the context and additional factors that focus and determine the outcome. At present, a unifying physiological context of AMPK activation by TAK1 remains elusive (Neumann, 2018).

We have recently reported that AMPK is activated by lysosomal damage, but the mechanism has not been elucidated (Jia et al., 2018). Previous studies have indicated that during lysosomal damage two seemingly independent systems spring into action—galectin and ubiquitin. Galectins are a family of cytosolic lectins recognizing β-galactoside glycans, with less understood intracellular functions and primarily being appreciated for their extracellular signaling (Johannes et al., 2018). Ubiquitin has been well studied during various aspects of selective autophagy and it opsonizes cargo for recognition by autophagic receptors (Kirkin et al., 2009). Ubiquitination also plays a regulatory role during autophagy controlling stability of several factors (Liu et al., 2016; Nazio et al., 2013). Additionally, ubiquitin remodeling on lysosomes by VCP/p97 is needed for efficient lysophagy (Papadopoulos et al., 2017). During lysophagy, galectin and ubiquitin responses are considered to act as "eat me" signals recruiting autophagy receptors and autophagy machinery (Chauhan et al., 2016; Maejima et al., 2013; Papadopoulos et al., 2017). In this context, the best example is the autophagic receptor NDP52 which binds both Galectin 8 (Gal8) and ubiquitin (Thurston et al., 2012). A recent study demonstrating that cytoplasmic Gal8 inhibits mTOR during lysosomal damage (Jia et al., 2018), suggests that intracellular galectins may play a broader regulatory role. However, that is yet to be broadly investigated. Furthermore, any functional interplay between galectin and ubiquitination responses have not been addressed beyond the intuitive model that they may provide additive opsonization signals for uptake by autophagic receptor during lysophagy.

In the present application, the inventors show how AMPK is activated in response to lysosomal damage and that both galectin and ubiquitination play regulatory and cooperative roles in AMPK activation leading up to autophagy induction. This cascade starts by the recognition of membrane damage by galectins, specifically by Gal9. Unexpectedly, the inventors found that Gal9 was necessary for efficient ubiquitination during lysosomal damage. One of the ubiquitinated proteins was TAK1, and it was responsible for activation of AMPK in response to lysosomal injury. These studies uncover a novel signal transduction pathway between galectin and ubiquitin systems, triggering AMPK activation and autophagy during lysosomal damage.

BRIEF DESCRIPTION OF THE INVENTION

In the present study, the inventors show that AMPK recruitment to lysosomes is enhanced upon lysosomal damage using the LysoIP method. Furthermore, Galectin9 (Gal9), which promptly detects lysosomal damage by binding to exposed exofacial glycans, facilitates the recruitment of AMPK to damaged lysosomes, resulting in activation of AMPK. Unexpectedly, the inventors found that Gal9 was necessary for efficient ubiquitination during lysosomal damage and that one of the ubiquitinated proteins was TAK1, and it was responsible for activation of AMPK in response to lysosomal injury. These studies uncover a novel signal transduction pathway between galectin and ubiquitin systems, triggering AMPK activation and autophagy during lysosomal damage. One of the ubiquitinated proteins was TAK1, and it was responsible for activation of AMPK in response to lysosomal injury Gal9 assists in AMPKα1 localization since Gal9 knockout cells fail to activate and recruit AMPK to damaged lysosomes. By using subcellular membrane fractionation the inventors found that following lysosomal damage LAMP2 shifted from heavier, typically lysosomal membranes to lighter membrane fractions that are positive for LC3-II, along with Gal9 and AMPK. This is interpreted as a shift of lysosomes to mixed-membrane fractions, likely of autophagosomal nature based on LC3-II as a marker. AMPK recruitment was required for this shift of lysosomes to the LC3-II+ lighter mixed-membrane fractions. Additionally, it was investigated whether lysosomal damage caused metabolic reprogramming/shifts in cells as measured by Seahorse Mito Stress test. This application and the related examples advance our understanding of how the Gal9-AMPK system responds during endomembrane damage by activating AMPK and targeting AMPK to damaged lysosomes. This is an example of how an apex regulator of cellular metabolism, AMPK, which also serves as an upstream regulator of autophagy, becomes engaged and properly targeted to the sites of action where autophagy exerts its quality control function.

In an embodiment, the present invention is directed to a method of treating autophagy mediated diseases by providing a AMPK agonist or antagonist, either alone or in combination with an agonist or antagonist of Galectin 9 and/or an agonist or antagonist of TAK1 to induce and/or enhance autophagy or to down regulate autophagy in the treatment of autophagy mediated disease. In alternative embodiments, a AMPK agonist or antagonist, often a AMPK agonist may be combined with a lysosomotropic agent as described herein for the treatment of autophagy mediated disease states and/or conditions. The AMPK agonist(s) and lysosomotropic agent(s) may be used alone or combined with a Galectin 9 agonist or antagonist and/or a TAK1 agonist or antagonist for the treatment of autophagy mediated disease states or conditions.

In embodiments, an AMPK agonist selected from the group consisting of metformin, 5-aminoimidazole-4-carboxamide (AICAR), 2-Deoxy-D-Glucose (2DG), salicylate, 4-Hydroxy-3-(2'-hydroxy-1,1'-biphenyl-4-yl)-6-oxo-6,7-dihydrothieno[2,3-b]pyridine-5-carbonitrile. (A-769662, CAS No. 844499-71-4), PF-249 (CAS No. 1467059-70-6), BL-AD008, PF-06885249, AMPK Activator 991 (CAS No. 1219739-36-2), AMPK Activator SC4, GSK621, ameliorate sodium and their pharmaceutically acceptable salts and mixtures thereof, among others alone or more preferably in combination with at least one lysosomotropic agent is administered to a patient or subject in need to treat an autophagy mediated disease state or condition as otherwise describe herein. In embodiments, the lysosomotropic agent is siramesine, sphingosine, N-dodecylimidazole, a lysosomotropic amine exhibiting a pKa between 5 and 9 often having an imidazole group or a morpholine group and a straight chain hydrocarbon of 9-14 carbon atoms, O-methyl-serinedodecyl amine and LZ-106 (emoxacin-benzimidazole hybrid where a benzimidazole group replaces the carboxylic acid group in emoxacin).

In embodiments, at least one AMPK inhibitor or a pharmaceutically acceptable salt thereof alone or in combination with at least one TAK1 Inhibitor and/or a galectin 9 inhibitor or a pharmaceutically acceptable salt thereof is administered to a patient or subject to treat any one or more fibrinolytic diseases or conditions including fibrosis, such as pulmonary fibrosis, idiopathic pulmonary fibrosis, cystic fibrosis, fibrothorax, radiation-induced lung injury, bridging fibrosis, glial scarring, athrofibrosis, Dupuytren's contracture, keloid fibrosis, scleroderma % systemic sclerosis, adhesive capsulitis, mediastinal fibrosis, myelofibrosis, peyronie's disease, nephrogenic systemic fibrosis, progressive massive fibrosis, retroperitoneal fibrosis, cardiac fibrosis. (endo)myocardial fibrosis, interstitial fibrosis, replacement fibrosis, cirrhosis, non-alcohol fatty liver disease (NAFLD), non-alcoholic steatohepatitis (NASH), chronic kidney disease, stromal fibrosis and epidural fibrosis, among others. Numerous cancers may also be treated in this manner. In embodiments, the AMPK inhibitor is desomorphin (compound C), (S)-4-(2-(4-Amino-1,2,5-oxadiazol-3-yl)-1-ethyl-7-(piperidin-3-ylmethoxy)-1H-imidazo[4,5-c]pyridin-4-yl)-2-methylbut-3-yn-2-ol (GSK 690693), (±) Bay K 8644 or a pharmaceutically acceptable salt, stereoisomer or enantiomer thereof or a mixture thereof. In embodiments, the TAK1 inhibitor is dehydroabietic acid, NG25 (CAS No. 1315355-93-1), sarsasapogenin, takinib, 1-(3-(tert-Butyl)-1-(3-cyanophenyl)-1H-pyrazol-5-yl)-3-(3-methyl-4-(pyridin-4-yloxy)phenyl)urea (PF-05381941 or CAS: 1474022-02-0), 5Z-7-oxozeaenol, TAK1-IN1, minnelide, triptolide or a pharmaceutically acceptable salt or mixture thereof.

In embodiments, a AMPK agonist or antagonist is combined with a Galectin 9 agonist or antagonist and/or a TAK1 agonist or antagonist and/or a lysosomotropic agent in further combination with a pharmaceutically acceptable carrier, additive or excipient to provide pharmaceutical compositions or to treat autophagy mediated disease states and/or conditions. In certain preferred embodiments, at least one AMPK agonist is combined with at least one lysosomotropic agent in effective amounts in further combination with a pharmaceutically acceptable carrier, additive or excipient to provide pharmaceutical compositions. In embodiments, the AMPK agonist is metformin, 5-aminoimidazole-4-carboxamide (AICAR), 2-Deoxy-D-Glucose (2DG), salicylate, 4-Hydroxy-3-(2'-hydroxy-1 b enyl-4-yl)-6-oxo-6,7-dihydrothieno[2,3-b]pyridine-5-carbonitrile, (A-769662, CAS No. 844499-71-4), PF-249 (CAS No. 1467059-70-6), BL-AD008, PF-06885249, AMPK Activator 991 (CAS No. 1219739-36-2), AMPK Activator SC4, GSK621, ameliorate sodium and their pharmaceutically acceptable salts and mixtures thereof, among others. In embodiments, the lysomotropic agent is siramesine, sphingosine, N-dodecylimidazole, a lysosomotropic amine exhibiting a pKa between 5 and 9 often having an imidazole group or a morpholine group and a straight chain hydrocarbon of 9-14 carbon atoms, O-methyl-serinedodecyl amine and LZ-106 (emoxacin-benzimidazole hybrid where a benzimidazole group replaces the carboxylic acid group in emoxacin) or a pharmaceutically acceptable salt or mixture thereof.

Certain conclusions are evidenced by the experimental results presented in the attached experiments and figures which facilitate the treatment of autophagy mediated disease states and/or conditions:

AMPK is activated in response to lysosomal damage and is translocated to damaged lysosomes in a Gal9 dependent manner. Gal9 recognizes damaged lysosomes by its ability to bind exposed glycans and thereby assists AMPK tra nslocation to damaged lysosomes. Further, damaged lysosomes move to lighter opti-prep fractions along with Gal9, AMPK and LC3-II.

Moreover, glycosylation mutants of Gal9 fail to bind AMPK and LAMP2, thereby highlighting the importance of glycan recognition by Gal9 as a signal for AMPK activation. Lysosomal damage also caused metabolic reprogramming as assessed by Mitostress test. Overall, the study advances the knowledge of how metabolic regulator. AMPK along with Gal9 plays in important role in endomembrane damage.

Mitogen-activated protein kinase kinase kinase 7 (TAK1, also known as MAP3K7) is also shown to activate AMPK.

In one embodiment the present invention is directed to a method of treating an autophagy related disease state or condition, the method comprising administering an agonist or antagonist of AMPK in combination with an agonist or antagonist of galectin 9 and/or an antagonist of TAK1 and/or an a lysosomotropic agent optionally in combination with a pharmaceutically acceptable carrier, additive or excipient. In certain preferred embodiments, the present invention is directed to the treatment of numerous autophagy mediated disease states and/or conditions by upregulating AMPK, alone or in combination with Galectin 9 upregulation and/or TAK1 upregulation and/or at least one lysosomotropic agent to increase autophagy and favorably treat the outcome of numerous autophagy-mediated disease states and/or conditions as otherwise described herein. In still other embodiments, the present invention is directed to the treatment of autophagy disease states and/or conditions which can be favorably treated by inhibiting AMPK as described herein. In this method, a patient or subject in need is administered at least one inhibitor of AMPK as described herein, optionally in combination with at least one galectin 9 inhibitor and/or at least one TAK1 inhibitor.

In certain embodiments, the MAPK agonist is combined with a galectin 9 agonist and/or a lysosomotropic agent and optionally, a pharmaceutically acceptable carrier, additive and/or excipient for the treatment of a patient or subject in need of therapy for an autophagy mediated disease state or condition. In embodiments, a MAPK antagonist is combined with a galectin 9 antagonist and/or a TAK1 antagonist for the treatment of disease states and/or conditions. Such disease states or conditions include fibrolytic disease states or conditions such as cystic fibrosis, fibrolytic disesase states of the liver including cirrhosis and non-alcohol steatohepatitis (NASH) and other liver diseases including non-alcohol fatty liver disease (NAFLD) as well as cardiovascular disease states and numerous other conditions where impaired fibrinolysis and fibrosis is a causative component, such as coronary heart disease and vascular disease.

In another embodiment, the present invention is directed to pharmaceutical compositions which comprise a modulator of AMPK in combination with an agonist of Galectin 9 and/or an agonist of TAK1 and/or a lysosomotropic agent in combination with a pharmaceutically acceptable carrier, additive or excipient. In preferred embodiments, the AMPK agonist is used in combination with a lysosomotropic agent. In embodiments, the AMPK agonist is agonist selected from the group consisting of metformin, 5-aminoimidazole-4-carboxamide (AICAR), 2-Deoxy-D-Glucose (2DG), salicylate, 4-Hydroxy-3-(2'-hydroxy-1,1'-biphenyl-4-yl)-6-oxo-6,7-dihydrothieno[2,3-b]pyridine-5-carbonitrile. (A-769662, CAS No. 844499-71-4), PF-249 (CAS No. 1467059-70-6), BL-AD008, PF-06885249, AMPK Activator 991 (CAS No. 1219739-36-2), AMPK Activator SC4, GSK621, ameliorate sodium and their pharmaceutically acceptable salts and mixtures thereof, among others. In embodiments, the lysosomotropic agent is siramesine, sphingosine, N-dodecylimidazole, a lysosomotropic amine exhibiting a pKa between 5 and 9 often having an imidazole group or a morpholine group and a straight chain hydrocarbon of 9-14 carbon atoms, O-methyl-serinedodecyl amine and LZ-106 (emoxacin-benzimidazole hybrid where a benzimidazole group replaces the carboxylic acid group in emoxacin).

In another embodiment, the present invention is directed to pharmaceutical compositions comprising an effective amount of a AMPK antagonist in combination with a TAK1 antagonist in combination with a pharmaceutically acceptable carrier, additive or excipient. In embodiments, the AMPK antagonist is desomorphin (compound C), (S)-4-(2-(4-Amino-1,2,5-oxadiazol-3-yl)-1-ethyl-7-(piperidin-3-ylmethoxy)-1H-imidazo[4,5-c]pyridin-4-yl)-2-methylbut-3-yn-2-ol (GSK 690693), (±) Bay K 8644 or a pharmaceutically acceptable salt, stereoisomer or enantiomer thereof or a mixture thereof. In embodiments, the TAK1 inhibitor is dehydroabietic acid, NG25 (CAS No. 1315355-93-1), sarsasapogenin, takinib, 1-(3-(tert-Butyl)-1-(3-cyanophenyl)-1H-pyrazol-5-yl)-3-(3-methyl-4-(pyridin-4-yloxy)phenyl)urea (PF-05381941 or CAS No. 1474022-02-0), 5Z-7-oxozeaenol, TAK1-IN1, minnelide, triptolide or a pharmaceutically acceptable salt or mixture thereof.

BRIEF DESCRIPTION OF THE FIGURES

FIG. 6S, related to FIG. 7 shows that Gal9-USP9X mediated signaling regulates autophagy during lysosomal damage. (A) Quantification of ATG13 response affected by Gal9$^{WT}$ and its mutant Gal9$^{R65A/R239A}$. Gal9KO$^{Huh7}$ transfected with FLAG-tagged Gal9$^{WT}$ or Gal9$^{R65A/R239A}$ were treated with 1 mM LLOMe for 30 min in full medium and subjected to HCM analysis of ATG13 puncta. White masks, algorithm defined cell boundaries (primary objects); green masks, computer-identified ATG13 puncta (target objects). Ctrl, control untreated cells. (B) Quantification of ATG16L1 response affected by Gal9$^{WT}$ and its mutant Gal9$^{R65A/R239A}$. Gal9KO$^{Huh7}$ transfected with FLAG-tagged Gal9$^{WT}$ or Gal9$^{R65A/R239A}$ were treated with 1 mM LLOMe for 30 min in full medium and subjected to HCM analysis of ATG116L1 puncta. White masks, algorithm defined cell boundaries (primary objects); green masks, computer-identified ATG16L1 puncta (target objects). Ctrl, control untreated cells. (C) HCM visualization of ATG13 puncta. Gal9WT$^{Huh7}$ and Gal9KO$^{Huh7}$ transfected with respective siRNA were treated with LLOMe for 30 min in full medium and the average area of ATG13 puncta per cell was analyzed by HCM. White masks, algorithm defined cell boundaries; red masks, computer-identified ATG13 puncta. Ctrl, control untreated cells. SCR, scrambled siRNA control. (D) HCM visualization of ATG16L1 puncta. Gal9WT$^{Huh7}$ and Gal9KO$^{Huh7}$ transfected with respective siRNA were treated with LLOMe for 30 min in full medium and the average area of ATG16L1 puncta per cell was analyzed by HCM. White masks, algorithm defined cell boundaries; red masks, computer-identified ATG16L1 puncta. Ctrl, control untreated cells. SCR, scrambled siRNA control. (E) *M. tuberculosis* survival assay in AMPKα1$^{fl/fl}$/α2$^{fl/fl}$ CX3CR1 Cre$^-$ and Cre$^+$ BMMs. Right: Western blot showing AMPKα knockout. Left. Percent survival of *M. tuberculosis* in AMPKα1$^{fl/}$ fl/α2$^{fl/fl}$ CX3CR1 Cre$^-$ and Cre$^+$ BMMs. BMMs were infected with *M. tuberculosis* strain Erdman at MOI 10 and incubated with full medium for 18 h or 16 h with following 2 h EBSS. CFU was enumerated 3 weeks later. Data indicate means±SEM (percentage of remaining colony-forming units relative to AMPKα1$^{fl/fl}$/α2$^{fl/fl}$ CX3CR1 Cre$^-$ BMMs incubated in full medium). (F) Overall model of Gal9 recruitment to damaged lysosomes and AMPK activation. A simplified model of how Gal9 recognizes exposed glycans on damaged lysosomes (FIG. 2), departs from USP9X (FIG. 3), promotes TAK1 ubiquitination (FIG. 4) followed by AMPK activation (FIGS. 5 and 6), and culminating on autophagic removal of damaged lysosomes (FIG. 7). Data, means±SEM; immunoblots, n≥3; HCM, n≥3 (each experiment: 500 valid primary objects/cells per well, ≥5 wells/sample). † p≥0.05 (not significant), *p<0.05, **p<0.01. ANOVA.

DETAILED DESCRIPTION OF THE INVENTION

Figure 1:
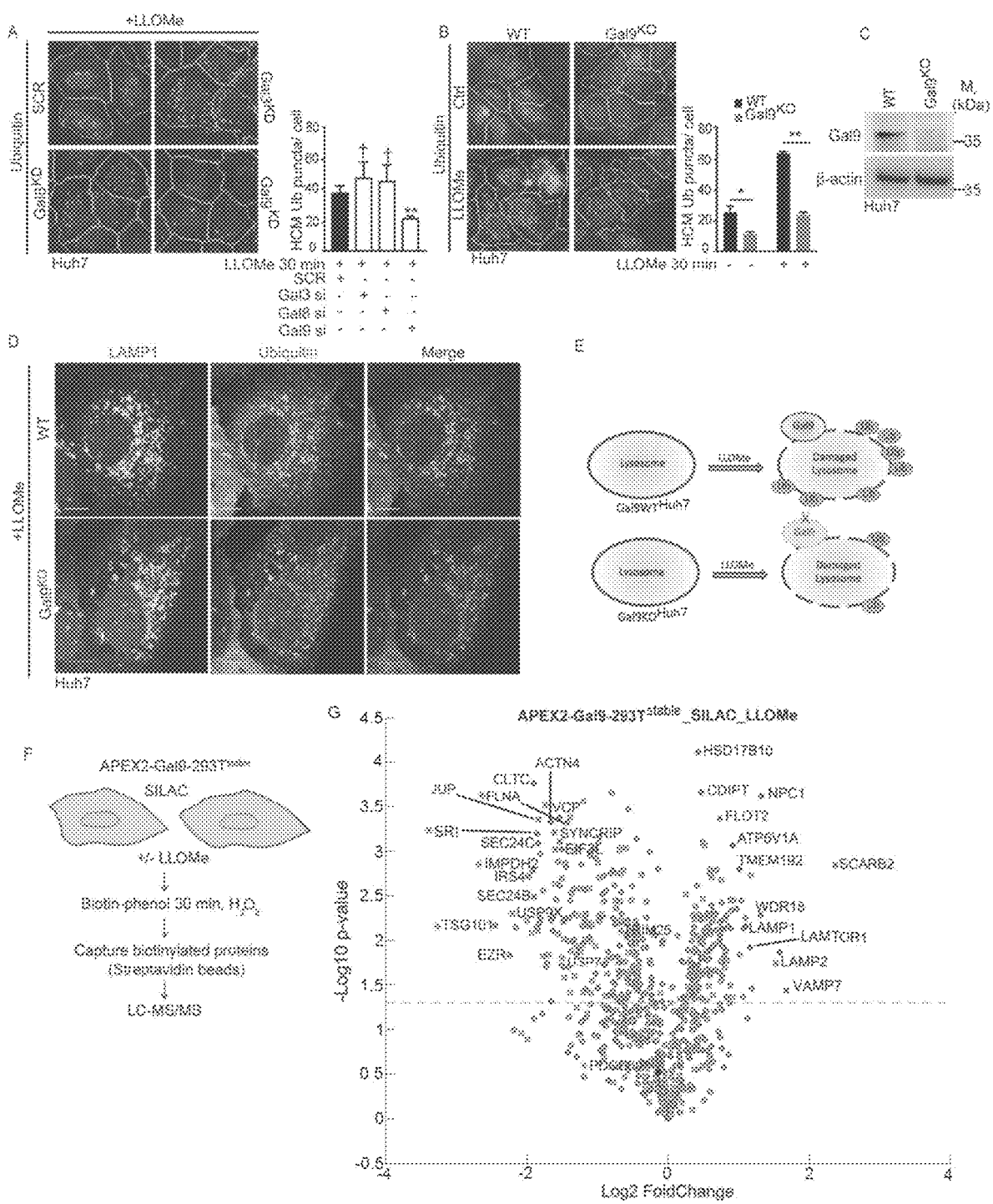
FIG. 1 shows that Gal9 is required for ubiquitination in response to lysosomal damage. (A) HCM (high content microscopy) quantification of endogenous ubiquitin (Ub) puncta formation in Huh7 cells transfected with respective siRNA and treated with lysosomal damaging agent (0 mM LLOMe) in full medium for 30 min. measured by (blue: nuclei, Hoechst 33342; green: anti-Ub FK2 antibody, Alexa-488). SCR, scrambled siRNA control. White masks, computer algorithm-defined cell boundaries (primary objects); green masks, computer-identified ubiquitin puncta (target objects). (B) Ub puncta (FK2) in Gal9WT$^{Huh7}$ and Gal9KO$^{Huh7}$ cells quantified by HCM. Treatment as in (A). Ctrl, control untreated cells. Masks as in A. (C) Western Blot (WB) analysis of Gal9 knockouts (Gal9WT$^{Huh7}$ and Gal9KO$^{Huh7}$). (D) Immunofluorescence confocal microscopy of Ub localization relative to LAMP1-positive lysosomes. Red florescence (LAMP1), Alexa-568. Green florescence (Ub), Alexa-488. Scale bar, 10 µM. (E) Schematic summary of the findings in FIG. 1. (F) Schematic steps for LC-MS/MS proteomic analysis using stable APEX2-Gal9-293T$^{stable}$ (see STAR Methods). (G) Volcano plot depicting dynamic changes in protein interactions/proximity relative to Gal9 in response to lysosomal damage. The plot is based on proteomic data in Table S1 (Tabs 2 and 3); treatment: 1 mM LLOMe, 1 h). Red and green circles, reduced and increased abundance of Gal9 proximity proteins, respectively (scale: Log 2 fold change) observed in at least two out of three biological replicates of stable APEX2-myc-Gal9 HEK293T cells subjected to separate LC-MS/MS analyses. Blue stars, proteins also identified in the LC-MS/MS analysis with 100 µM GPN treatment (see FIG. 3A). See also FIG. 3A and Table S1 (Tabs 2 and 3). Data, means±SEM; immunoblots, n≥3; HCM, n≥3 (each experiment: 500 valid primary objects/cells per well, ≥5 wells/sample). † p≥0.05 (not significant), *p<0.05, **p<0.01, ANOVA. See also Figure S1.

It is noted that, as used in this specification and the appended claims, the singular forms "a," "an," and "the," include plural referents unless expressly and unequivocally limited to one referent. Thus, for example, reference to "a compound" includes two or more different compound. As used herein, the term "include" and its grammatical variants are intended to be non-limiting, such that recitation of items in a list is not to the exclusion of other like items that can be substituted or other items that can be added to the listed items.

The term "compound" or "agent", as used herein, unless otherwise indicated, refers to any specific chemical compound or composition (such as a Galectin protein, agonist antagonist, an AMPK agonist or antagonist or other compound) disclosed herein, a TAK1 agonist or antagonist or a lysosomotropic agent and includes tautomers, regioisomers, geometric isomers as applicable, and also where applicable, stereoisomers, including diastereomers, optical isomers (e.g. enantiomers) thereof, as well as pharmaceutically acceptable salts thereof. Within its use in context, the term compound generally refers to a single compound, but also may include other compounds such as stereoisomers, regioisomers and/or optical isomers (including racemic mixtures) as well as specific enantiomers or enantiomerically enriched mixtures of disclosed compounds as well as diastereomers and epimers, where applicable, in context. The term also refers, in context to prodrug forms of compounds which have been modified to facilitate the administration and delivery of compounds to a site of activity.

The term "patient" or "subject" is used throughout the specification within context to describe an animal, generally a mammal, including a domesticated mammal including a farm animal (dog, cat, horse, cow, pig, sheep, goat, etc.) and preferably a human, to whom treatment, including prophylactic treatment (prophylaxis), with the methods and compositions according to the present invention is provided. For treatment of those conditions or disease states which are specific for a specific animal such as a human patient, the term patient refers to that specific animal, often a human.

The terms "effective" or "pharmaceutically effective" are used herein, unless otherwise indicated, to describe an amount of a compound or composition which, in context, is used to produce or affect an intended result, usually the modulation (inhibition or upregulation) of autophagy within the context of a particular treatment or alternatively, the effect of a bioactive agent which is coadministered with the autophagy modulator (autotoxin) in the treatment of disease.

The terms "treat", "treating", and "treatment", etc., as used herein, refer to any action providing a benefit to a patient at risk for or afflicted by an autophagy mediated disease state or condition as otherwise described herein, especiallyi where excessive inflammation results from the disease state and/or condition. The benefit may be in curing the disease state or condition, inhibiting its progression, or ameliorating, lessening or suppressing one or more symptom of an autophagy mediated disease state or condition, especially including excessive inflammation caused by the disease state and/or condition. Treatment, as used herein, encompasses therapeutic treatment and in certain instances, prophylactic treatment, depending on context.

As used herein, the term "autophagy mediated disease state or condition" refers to a disease state or condition that results from disruption in autophagy or cellular self-digestion and in particular, causes or is a risk for causing excessive inflammation. Autophagy is a cellular pathway involved in protein and organelle degradation, and has a large number of connections to human disease. Autophagic dysfunction which causes inflammation is associated with inflammatory diseases, including neurodegeneration, autoimmune diseases, microbial infections, cardiovascular diseases and metabolic diseases including diabetes mellitus, among numerous other disease states and/or conditions. Although autophagy plays a principal role as a protective process for the cell, it also plays a role in cell death. Disease states and/or conditions which are mediated through autophagy (which refers to the fact that the disease state or condition may manifest itself as a function of the increase or decrease in autophagy in the patient or subject to be treated and treatment requires administration of an inhibitor or agonist of autophagy in the patient or subject) include, for example, lysosomal storage diseases (discussed hereinbelow), neurodegeneration (including, for example, Alzheimer's disease, Parkinson's disease. Huntington's disease; other ataxias), immune response (T cell maturation, B cell and T cell homeostasis, counters damaging inflammation), autoimmune diseases and chronic inflammatory diseases resulting in excessive inflammation (these disease states may promote excessive cytokines when autophagy is defective), including, for example, inflammatory bowel disease, including Crohn's disease, rheumatoid arthritis, lupus, multiple sclerosis, chronic obstructive pulmony disease/COPD, pulmonary fibrosis, cystic fibrosis. Sjogren's disease; hyperglycemic disorders, diabetes (I and II), affecting lipid metabolism islet function and/or structure, excessive autophpagy may lead to pancreatic β-cell death and related hyperglycemic disorders, including severe insulin resistance, hyperinsulinemia, insulin-resistant diabetes (e.g. Mendenhall's Syndrome, Werner Syndrome, leprechaunism, and lipoatrophic diabetes) and dyslipidemia (e.g. hyperlipidemia as expressed by obese subjects, elevated low-density lipoprotein (LDL), depressed high-density lipoprotein (HDL), and elevated triglycerides) and metabolic syndrome, liver disease (excessive autophagic removal of cellular entities—endoplasmic reticulum), renal disease (apoptosis in plaques, glomerular disease), cardiovascular disease (especially including infarction, ischemia, stroke, pressure overload and complications during reperfusion), muscle degeneration and atrophy, symptoms of aging (including amelioration or the delay in onset or severity or frequency of aging-related symptoms and chronic conditions including muscle atrophy, frailty, metabolic disorders, low grade inflammation, gout, silicosis, atherosclerosis and associated conditions such as cardiac and neurological both central and peripheral manifestations including stroke, age-associated dementia and sporadic form of Alzheimer's disease, and psychiatric conditions including depression), stroke and spinal cord injury, arteriosclerosis, infectious diseases (microbial infections, removes microbes, provides a protective inflammatory response to microbial products, limits adapation of authophagy of host by microbe for enhancement of microbial growth, regulation of innate immunity) including bacterial, fungal, cellular and viral (including secondary disease states or conditions associated with infectious diseases especially including Mycobacterial infections such as *M. tuberculosis*, and viral infections such as heptais B and C and HIV I and II), including AIDS, among others.

In addition, an autophagy disease state or condition includes autoimmune diseases such as myocarditis, Antiglomercular Base Membrane Nephritis, lupus erythematosus, lupus nephritis, autoimmune hepatitis, primary biliary cirrhosis, alopecia areata, autoimmune urticaria, bullous pemphagoid, dermatitis herpetiformis, epidermolysis bullosa acquisita, linear IgA disease (LAD), pemphigus vulgaris, psoriasis. Addison's disease, autoimmune polyendocrine syndrome I, II and III (APS I, APS II, APS III), autoimmune pancreatitis, type I diabetes, autoimmune thyroiditis, Ord's thyroiditis, Grave's disease, autoimmune oophoritis, Sjogren's syndrome, autoimmune enteropathy, Coeliac disease, Crohn's disease, autoimmune hemolytic anemia, autoimmune lymphoproliferative syndrome, autoimmune neutropenia, autoimmune thrombocytopenic purpura, Cold agglutinin disease, Evans syndrome, pernicious anemia, Adult-onset Still's disease, Felty syndrome, juvenile arthritis, psoriatic arthritis, relapsing polychondritis, rheumatic fever, rheumatoid arthritis, myasthenia gravis, acute disseminated encephalomyelitis (ADEM), balo concentric sclerosis, Guillain-Barre syndrome, Hashimoto's encephalopathy, chronic inflammatory demvelinating polyneuropathy, Lambert-Eaton myasthenic syndrome, multiple sclerosis, autoimmune uveitis, Graves opthalmopathy, Granulomatosis with polyangitis (GPA), Kawasaki's disease, vasculitis and chronic fatigue syndrome, among others.

The term "Galectin-9" or "Galectin protein-9" is used to describe a protein defined by its binding specificity for p-galactoside sugars, such as N-acetyllactosamine (Galβ1-3GlcNAc or Galβ1-4GlcNAc), which can be bound to proteins by either N-linked or O-linked glycosylation. Galectin-9 is a tandem-repeat type galectin with two carbohydrate-recognition domains, and has been identified as an eosinophil chemoattractant and activation factor. Other studies have revealed that galectin-9, similar to other galectins, modulates a variety of biological functions including cell aggregation and adhesion, as well as apoptosis of tumor cells. Galectin-9 has recently been shown to have an antiproliferative effect on cancer cells.

There have been 15 galectins identified in mammals; these include Galectin-1, -2, -3, -4, -7, -8, -9, -10, -12 and -13 have been identified in humans. In preferred aspects of the invention, human galectins are used, more preferably human Galectin-9. As used herein, the term Galectin-9 describes Galectin-9 protein and includes variants and isoforms (1-6) thereof having at least 80%, 85%, 90% or 95% sequence identity to the most common form of the protein, which is preferably the human protein. Preferred Galectin-9 proteins include the following Galectin proteins or variants thereof having at least 80%, 85%, 90% or 95% sequence identity. The following sequence Galectin 9 isoform 1 is representative of the human Galectin proteins which are of preferred use herein.

```
Galectin-9 Accession No. NP_001036150.1
                                             SEQ ID NO: 1
MAFSGSQAPY LSPAVPFSGT IQGGLQDGLQ ITVNGTVLSS
        60         70         80         90

SGTRFAVNFQ TGFSGNDIAF HFNPRFEDGG YVVCNTRQNG
       100        110        120        130

SWGPEERKTH MPFQKGMPFD LCFLVQSSDF KVMVNGILFV
       140        150        160        170

QYFHRVPFHR VDTISVNGSV QLSYISFQNP RTVPVQPAFS
       180        190        200        210

TVPFSQPVCF PPRPRGRRQK PPGVWPANPA PITQTVIHTV
       220        230        240        250

QSAPGQMFST PAIPPMMYPH PAYPMPFITT ILGGLYPSKS
       260        270        280        290

ILLSGTVLPS AQRFHINLCS GNHIAFHLNP RFDENAVVRN
       300        310        320        330

TQIDNSWGSE ERSLPRKMPF VRGQSFSVWI LCEAHCLKVA
       340        350

VDGQHLFEYY HRLRNLPTIN RLEVGGDIQL THVQT
```

The term "lysosomal storage disorder" refers to a disease state or condition that results from a defect in lysosomomal storage. These disease states or conditions generally occur when the lysosome malfunctions. Lysosomal storage disorders are caused by lysosomal dysfunction usually as a consequence of deficiency of a single enzyme required for the metabolism of lipids, glycoproteins or mucopolysaccharides. The incidence of lysosomal storage disorder (collectively) occurs at an incidence of about about 1:5,000-1:10,000. The lysosome is commonly referred to as the cell's recycling center because it processes unwanted material into substances that the cell can utilize. Lysosomes break down this unwanted matter via high specialized enzymes. Lysosomal disorders generally are triggered when a particular enzyme exists in too small an amount or is missing altogether. When this happens, substances accumulate in the cell. In other words, when the lysosome doesn't function normally, excess products destined for breakdown and recycling are stored in the cell. Lysosomal storage disorders are genetic diseases, but these may be treated using autophagy modulators according to the present invention, especially where the disease state or condition produces excessive inflammation as otherwise described herein. All of these diseases share a common biochemical characteristic, i.e., that all lysosomal disorders originate from an abnormal accumulation of substances inside the lysosome. Lysosomal storage diseases mostly affect children who often die as a consequence at an early stage of life, many within a few months or years of birth. Many other children die of this disease following years of suffering from various symptoms of their particular disorder.

Examples of lysosomal storage diseases include, for example, activator deficiency/GM2 gangliosidosis, alpha-mannosidosis, aspartylglucoaminuria, cholesteryl ester storage disease, chronic hexosaminidase A deficiency, cystinosis, Danon disease, Fabry disease, Farber disease, fucosidosis, galactosialidosis, Gaucher Disease (Types I, II and III), GM2 Ganliosidosis, including infantile, late infantile/juvenile and adult/chronic), Hunter syndrome (MPS 11), I-Cell disease/Mucolipidosis II, Infantile Free Sialic Acid Storage Disease (ISSD), Juvenile Hexosaminidase A Deficiency, Krabbe disease, Lysosomal acid lipase deficiency, Metachromatic Leukodystrophy, Hurler syndrome, Scheie syndrome, Hurler-Scheie syndrome, Sanfilippo syndrome, Morquio Type A and B, Maroteaux-Lamy, Sly syndrome, mucolipidosis, multiple sulfate deficiency. Niemann-Pick disease, Neuronal ceroid lipofuscinoses, CLN6 disease, Jansky-Bielschowsky disease, Pompe disease, pycnodysostosis, Sandhoff disease, Schindler disease, Tay-Sachs and Wolman disease, among others.

Autophagy disease states and/or condition described above are treated using at least one AMPK agonist alone or in combination with one or more lyosomotropic agents. In embodiments, the AMPK agonist is a AMPK agonist selected from the group consisting of metformin, 5-amino-imidazole-4-carboxamide (AICAR), 2-Deoxy-D-Glucose (2DG), salicylate, 4-Hydroxy-3-(2'-hydroxy-1,1'-biphenyl-4-yl)-6-oxo-6,7-dihydrothieno[2,3-b]pyridine-5-carbonitrile, (A-769662, CAS No. 844499-71-4), PF-249 (CAS No. 1467059-70-6). BL-AD008, PF-06885249, AMPK Activator 991 (CAS No. 1219739-36-2), AMPK Activator SC4, GSK621, ameliorate sodium and their pharmaceutically acceptable salts and mixtures thereof, among others. In embodiments, the AMPK agonist is preferably used in combination in a single composition or separately with at least one lysosomotropic agent which is administered to a patient or subject in need to treat an autophagy mediated disease state or condition as otherwise describe herein. In embodiments, the lysosomotropic agent is siramesine, sphingosine, N-dodecylimidazole, a lysosomotropic amine exhibiting a pKa between 5 and 9 often having an imidazole group or a morpholine group and a straight chain hydrocarbon of 9-14 carbon atoms. O-methyl-serinedodecyl amine and LZ-106 (emoxacin-benzimidazole hybrid where a benzimidazole group replaces the carboxylic acid group in emoxacin).

In embodiments, an AMPK inhibitor is used alone or in combination with a TAK1 inhibitor and/or a galectin 9 inhibitor for the treatment of a disease state or condition in which fibrosis occurs, such as pulmonary fibrosis, idiopathic pulmonary fibrosis, cystic fibrosis, fibrothorax, radiation-induced lung injury, bridging fibrosis, glial scarring, athrofibrosis, Dupuytren's contracture, keloid fibrosis, scleroderma % systemic sclerosis, adhesive capsulitis, mediastinal fibrosis, myelofibrosis, peyronie's disease, nephrogenic systemic fibrosis, progressive massive fibrosis, retroperitoneal fibrosis, cardiac fibrosis. (endo)myocardial fibrosis, interstitial fibrosis, replacement fibrosis, cirrhosis, non-alcohol fatty liver disease (NAFLD), non-alcoholic steatohepatitis (NASH), chronic kidney disease, stromal fibrosis and epidural fibrosis, among others. In addition, these agents are useful in the treatment of numerous cancers as otherwise described herein. In embodiments, the AMPK inhibitor is desomorphin (compound C). (S)-4-(2-(4-Amino-1,2,5-oxadiazol-3-yl)-1-ethyl-7-(piperidin-3-ylmethoxy)-1H-imidazo[4,5-c]pyridin-4-yl)-2-methylbut-3-yn-2-ol (GSK 690693), (±) Bay K 8644 or a pharmaceutically acceptable salt, stereoisomer or enantiomer thereof or a mixture thereof. In embodiments, the TAK1 inhibitor is dehydroabietic acid, NG25 (CAS No. 1315355-93-1), sarsasapogenin, takinib, 1-(3-(tert-Butyl)-1-(3-cyanophenyl)-1H-pyrazol-5-yl)-3-(3-methyl-4-(pyridin-4-yloxy)phenyl)urea (PF-05381941 or CAS: 1474022-02-0), 5Z-7-oxozeaenol, TAK1-IN1, minnelide, triptolide or a pharmaceutically acceptable salt or mixture thereof.

The term "modulator of autophagy", "regulator of autophagy" or "autostatin" is used to refer to a compound which functions as an agonist (inducer or up-regulator) or antagonist (inhibitor or down-regulator) of autophagy. Depending upon the disease state or condition, autophagy may be upregulated (and require inhibition of autophagy for therapeutic intervention) or down-regulated (and require upregulation of autophagy for therapeutic intervention). In most instances, in the case of cancer treatment with a modulator of autophagy as otherwise described herein, the autophagy modulator is often an antagonist (down-regulator or inhibitor) of autophagy. In the case of cancer, the antagonist (inhibitor) of autophagy may be used alone or combined with an agonist of autophagy. In other instances, the modulator is an upregulator of autophagy.

The following compounds have been identified as autophagy modulators according to the present invention and can be used in the treatment of an autophagy mediated disease state or condition as otherwise described herein. These include interferon types I and II, especially interferon-alpha, interferon-beta, interferon interferon-gamma (IFN-gamma), pegylated interferon (PEG-IFN) type 1 or type 2 (especially including interferon alpha 2a and/or 2b), mixtures thereof, other cytokines and related compounds and mixtures thereof. In addition, Galectin proteins (1, 2, 3, 4, 7, 8, 9, 10, 12 and 13), preferably human Galectin proteins may also be included as autophagy modulators, especially Galectin-9, with Galectin-9 being especially preferred. Agonists and/or inhibitors of Galectin-9, including a galactose containing sugar or other sugar compound (especially lactose, including N-linked and O-linked lactose such as N-acetyl lactosamine which acts as an agonist or an inhibitor such as a galactoside inhibitor or alternatively, a lactulose amine such as N-lactulose-octamethylenediamine (LDO); N,N-dilactulose-octamethylenediamine (D-LDO), and N,N-dilactulose-dodecamethylenediamine (D-LDD)), GR-MD-02, GM-CT-01, GCS-100, ipilimumab, a pectin, or a taloside inhibitor may also be used.

In addition, the following sugars may also be used as inhibitors and/or agonists of the Galectins, especially Galectin-9. These sugars include, for example, monosaccharides, including β-galactoside sugars, such as galactose, including N- or O-linked (e.g., acetylated) galactosides and disaccharides, oligosaccharides and polysaccharides which contain at least one galactose sugar moiety. These include lactose, mannobiose, melibiose (which may have the glucose residue and/or the galactose residue optionally N-acetylated), melibiulose (which may have the galactose residue optionally N-acetylated), rutinose, (which may have the glucose residue optionally N-acetylated), rutinose and xylobiose, among others, and trehalose, all of which can be N and O-linked. Oligosaccharides for use in the present invention as can include any sugar of three or more (up to about 100) individual sugar (saccharide) units as described above (i.e., any one or more saccharide units described above, in any order, especially including galactose units such as galactooligosaccharides and mannan-oligosaccharides ranging from three to about ten-fifteen sugar units in size.

Sugars which are galactosides or contain galactose (galactose derivatives) are preferred for use in the present invention. These sugars may function as inhibitors or agonists of galectins, especially galectin 3. One or more of these above sugars may be combined with an agonist or antagonist of AMPK, further optionally with an interferon, a biguanide, a salicylate and a biguanide, berberine, ambroxol or a mixture thereof in order to upregulate autophagy and treat the autophagy diseases where upregulation is beneficial (e.g., inflammatory disease states and/or conditions including a microbial infection such as a *Mycobacterium* infection, among numerous others, an inflammatory disorder, a lysosomal storage disorder, an immune disorder, a neurodegenerative disorder, an autoimmune disease).

Alternatively, one or more sugars described above may function as an inhibitor or agonist of Galectin 9 to be used in combination with an agonist or inhibitor of AMPK (e.g. AMPK itself, a peptide fragment agonist of AMPK or a peptide antagonist of AMPK and/or an anti-AMPK antibody or AICAR, PF-06409577, PF-249, BL-AD008, PF-06885249, AMPK Activator 991, AMPK Activator SC4 and GSK621, among others) for the treatment of autophagy mediated disease states and/or conditions including cancers. Useful AMPK agonists for use in the present invention include metformin, 5-aminoimidazole-4-carboxamide (AICAR), 2-Deoxy-D-Glucose (2DG), salicylate, 4-Hydroxy-3-(2'-hydroxy-1,1'-biphenyl-4-yl)-6-oxo-6,7-dihydrothieno[2,3-b]pyridine-5-carbonitrile, (A-769662, CAS No. 844499-71-4), PF-249 (CAS No. 1467059-70-6), BL-AD008, PF-06885249, AMPK Activator 991 (CAS No. 1219739-36-2), AMPK Activator SC4, GSK621, ameliorate sodium and their pharmaceutically acceptable salts and mixtures thereof, among others. Useful AMPK inhibitors include desomorphin (compound C), (S)-4-(2-(4-Amino-1, 2,5-oxadiazol-3-yl)-1-ethyl-7-(piperidin-3-ylmethoxy)-1H-imidazo[4,5-c]pyridin-4-yl)-2-methylbut-3-yn-2-ol (GSK 690693), (±) Bay K 8644 or a pharmaceutically acceptable salt, stereoisomer or enantiomer thereof or a mixture thereof. Useful galectin inhibitors include galactoside inhibitors or alternatively, a lactulose amine such as N-lactulose-octamethylenediamine (LDO); N,N-dilactulose-octamethylenediamine (D-LDO), and N,N-dilactulose-dodecamethylenediamine (D-LDD)), GR-MD-02, ipilimumab, a pectin, or a taloside inhibitor, among others may be used as an inhibitor of a galectin as described herein, especially galectin 9. These agents are particularly effective as anticancer agents with certain cancers especially when combined with AMPK modulators (often an AMPK inhibitor).

The following compounds have been identified as autophagy modulators which may be used in combination with the above-identified autophagy agents. These agents include, for example flubendazole, hexachlorophene, propidium iodide, bepridil, clomiphene citrate (Z,E), GBR 12909, propafenone, metixene, dipivefrin, fluvoxamine, dicyclomine, dimethisoquin, ticlopidine, memantine, bromhexine, ambroxol, norcyclobenzaprine, diperodon and nortriptyline, tetrachlorisophthalonitrile, phenylmercuric acetate and pharmaceutically acceptable salts thereof. It is noted that flubendazole, hexachlorophene, propidium iodide, bepridil, clomiphene citrate (Z,E), GBR 12909, propafenone, metixene, dipivefrin, fluvoxamine, dicyclomine, dimethisoquin, ticlopidine, memantine, bromhexine, norcyclobenzaprine, diperodon, nortriptyline, benzethonium, niclosamide, monensin, bromperidol, levobunolol, dehydroisoandosterone 3-acetate, sertraline, tamoxifen, reserpine, hexachlorophene, dipyridamole, harmaline, prazosin, lidoflazine, thiethylperazine, dextromethorphan, desipramine, mebendazole, canrenone, chlorprothixene, maprotiline, homochlorcyclizine, loperamide, nicardipine, dexfenfluramine, nilvadipine, dosulepin, biperiden, denatonium, etomidate, toremifene, tomoxetine, clorgyline, zotepine, beta-escin, tridihexethyl, ceflazidime, methoxy-6-harmalan, melengestrol, albendazole, rimantadine, chlorpromazine, pergolide, cloperastine, prednicarbate, haloperidol, clotrimazole, nitrofural, iopanoic acid, naftopidil, Methimazole, Trimeprazine, Ethoxyquin, Clocortolone, Doxycycline, Pirlindole mesylate, Doxazosin, Deptropine, Nocodazole, Scopolamine, Oxybenzone, Halcinonide, Oxybutynin, Miconazole, Clomipramine, Cyproheptadine, Doxepin. Dyclonine, Salbutamol, Flavoxate, Amoxapine, Fenofibrate. Pimethixene, and mixtures thereof.

The term "co-administration" or "combination therapy" is used to describe a therapy in which at least two active compounds in effective amounts are used to treat an autophagy mediated disease state or condition as otherwise described herein, either at the same time or within dosing or administration schedules defined further herein or ascertainable by those of ordinary skill in the art. Although the term co-administration preferably includes the administration of two active compounds to the patient at the same time, it is not necessary that the compounds be administered to the patient at the same time, although effective amounts of the individual compounds will be present in the patient at the same time. In addition, in certain embodiments, co-administration will refer to the fact that two compounds are administered at significantly different times, but the effects of the two compounds are present at the same time. Thus, the term co-administration includes an administration in which one active agent (especially an autophagy modulator) is administered at approximately the same time (contemporaneously), or from about one to several minutes to about 24 hours or more than the other bioactive agent coadministered with the autophagy modulator.

The additional bioactive agent may be any bioactive agent, but is generally selected from an additional autophagy mediated compound or another agent such as a mTOR inhibitor such as Torin, pp242, rapamycin/serolimus (which also may function as an autophagy modulator), everolimus, temsirolomis, ridaforolimis, zotarolimis, 32-dexoy-rapamycin, among others including epigallocatechin gallate (EGCG), caffeine, curcumin or reseveratrol (which mTOR inhibitors find particular use as enhancers of autophagy using the compounds disclosed herein. In certain embodiments, an mTOR inhibitor selected from the group consisting of Torin, pp242, rapamycin/serolimus, everolimus, temsirolomis, ridaforolimis, zotarolimis, 32-dexoy-rapamycin, epigallocatechin gallate (EGCG), caffeine, curcumin or reseveratrol and mixtures thereof may be combined with at least one agent selected from the group consisting of digoxin, xylazine, hexetidine and sertindole, the combination of such agents being effective as autophagy modulators in combination.

The terms "cancer" and "neoplasia" are used throughout the specification to refer to the pathological process that results in the formation and growth of a cancerous or malignant neoplasm, i.e., abnormal tissue that grows by cellular proliferation, often more rapidly than normal and continues to grow after the stimuli that initiated the new growth cease. Malignant neoplasms show partial or complete lack of structural organization and functional coordination with the normal tissue and most invade surrounding tissues, metastasize to several sites, and are likely to recur after attempted removal and to cause the death of the patient unless adequately treated.

As used herein, the terms malignant neoplasia and cancer are used synonymously to describe all cancerous disease states and embraces or encompasses the pathological process associated with malignant hematogenous, ascitic and solid tumors. Representative cancers include, for example, stomach, colon, rectal, liver, pancreatic, lung, breast, cervix uteri, corpus uteri, ovary, prostate, testis, bladder, renal, brain/CNS, head and neck, throat, Hodgkin's disease, non-Hodgkin's lymphoma, multiple myeloma, leukemia, melanoma, non-melanoma skin cancer (especially basal cell carcinoma or squamous cell carcinoma), acute lymphocytic leukemia, acute myelogenous leukemia, Ewing's sarcoma, small cell lung cancer, choriocarcinoma, rhabdomyosarcoma, Wilms' tumor, neuroblastoma, hairy cell leukemia, mouth/pharynx, oesophagus, larynx, kidney cancer and lymphoma, among others, which may be treated by one or more compounds according to the present invention. In certain aspects, the cancer which is treated is lung cancer, breast cancer, ovarian cancer and/or prostate cancer.

Neoplasms include, without limitation, morphological irregularities in cells in tissue of a subject or host, as well as pathologic proliferation of cells in tissue of a subject, as compared with normal proliferation in the same type of tissue. Additionally, neoplasms include benign tumors and malignant tumors (e.g., colon tumors) that are either invasive or noninvasive. Malignant neoplasms (cancer) are distinguished from benign neoplasms in that the former show a greater degree of anaplasia, or loss of differentiation and orientation of cells, and have the properties of invasion and metastasis. Examples of neoplasms or neoplasias from which the target cell of the present invention may be derived include, without limitation, carcinomas (e.g., squamous-cell carcinomas, adenocarcinomas, hepatocellular carcinomas, and renal cell carcinomas), particularly those of the bladder, bowel, breast, cervix, colon, esophagus, head, kidney, liver, lung, neck, ovary, pancreas, prostate, stomach and thyroid; leukemias; benign and malignant lymphomas, particularly Burkitt's lymphoma and Non-Hodgkin's lymphoma; benign and malignant melanomas; myeloproliferative diseases; sarcomas, particularly Ewing's sarcoma, hemangiosarcoma, Kaposi's sarcoma, liposarcoma, myosarcoma, peripheral neuroepithelioma, and synovial sarcoma; tumors of the central nervous system (e.g., gliomas, astrocytomas, oligodendrogliomas, ependymomas, gliobastomas, neuroblastomas, ganglioneuromas, gangliogliomas, medulloblastomas, pineal cell tumors, meningiomas, meningeal sarcomas, neurofibromas, and Schwannomas); germ-line tumors (e.g., bowel cancer, breast cancer, prostate cancer, cervical cancer, uterine cancer, lung cancer, ovarian cancer, testicular cancer, thyroid cancer, astrocytoma, esophageal cancer, pancreatic cancer, stomach cancer, liver cancer, colon cancer, and melanoma); mixed types of neoplasias, particularly carcinosarcoma and Hodgkin's disease; and tumors of mixed origin, such as Wilms' tumor and teratocarcinomas (Beers and Berkow (eds.), The Merck Manual of Diagnosis and Therapy, 17.sup.th ed. (Whitehouse Station, N.J.: Merck Research Laboratories, 1999) 973-74, 976, 986, 988, 991). All of these neoplasms may be treated using compounds according to the present invention.

Representative common cancers to be treated with compounds according to the present invention include, for example, prostate cancer, metastatic prostate cancer, stomach, colon, rectal, liver, pancreatic, lung, breast, cervix uteri, corpus uteri, ovary, testis, bladder, renal, brain/CNS, head and neck, throat, Hodgkin's disease, non-Hodgkin's lymphoma, multiple myeloma, leukemia, melanoma, non-melanoma skin cancer, acute lymphocytic leukemia, acute myelogenous leukemia, Ewing's sarcoma, small cell lung cancer, choriocarcinoma, rhabdomyosarcoma, Wilms' tumor, neuroblastoma, hairy cell leukemia, mouth/pharynx, oesophagus, larynx, kidney cancer and lymphoma, among others, which may be treated by one or more compounds according to the present invention. Because of the activity of the present compounds, the present invention has general applicability treating virtually any cancer in any tissue, thus the compounds, compositions and methods of the present invention are generally applicable to the treatment of cancer and in reducing the likelihood of development of cancer and/or the metastasis of an existing cancer.

In certain particular aspects of the present invention, the cancer which is treated is metastatic cancer, a recurrent cancer or a drug resistant cancer, especially including a drug resistant cancer. Separately, metastatic cancer may be found in virtually all tissues of a cancer patient in late stages of the disease, typically metastatic cancer is found in lymph system/nodes (lymphoma), in bones, in lungs, in bladder tissue, in kidney tissue, liver tissue and in virtually any tissue, including brain (brain cancer/tumor). Thus, the present invention is generally applicable and may be used to treat any cancer in any tissue, regardless of etiology.

The term "tumor" is used to describe a malignant or benign growth or tumefacent.

The term "additional anti-cancer compound", "additional anti-cancer drug" or "additional anti-cancer agent" is used to describe any compound (including its derivatives) which may be used to treat cancer. The "additional anti-cancer compound", "additional anti-cancer drug" or "additional anti-cancer agent" can be an anticancer agent which is distinguishable from a CIAE-inducing anticancer ingredient such as a taxane, *vinca* alkaloid and/or radiation sensitizing agent otherwise used as chemotherapy/cancer therapy agents herein. In many instances, the co-administration of another anti-cancer compound according to the present invention results in a synergistic anti-cancer effect. Exemplary anti-cancer compounds for co-administration with formulations according to the present invention include antimetabolites agents which are broadly characterized as antimetabolites, inhibitors of topoisomerase I and II, alkylating agents and microtubule inhibitors (e.g., taxol), as well as tyrosine kinase inhibitors (e.g., surafenib), EGF kinase inhibitors (e.g., tarceva or erlotinib) and tyrosine kinase inhibitors or ABL kinase inhibitors (e.g. imatinib).

Anti-cancer compounds for co-administration include, for example, agent(s) which may be co-administered with compounds according to the present invention in the treatment of cancer. These agents include chemotherapeutic agents and include one or more members selected from the group consisting of everolimus, trabectedin, abraxane, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, a FLT-3 inhibitor, a VEGFR inhibitor, an EGFR TK inhibitor, an aurora kinase inhibitor, a PIK-1 modulator, a Bcl-2 inhibitor, an HDAC inhbitor, a c-MET inhibitor, a PARP inhibitor, a Cdk inhibitor, an EGFR TK inhibitor, an IGFR-TK inhibitor, an anti-HGF antibody, a PI3 kinase inhibitors, an AKT inhibitor, a JAK/STAT inhibitor, a checkpoint-1 or 2 inhibitor, a focal adhesion kinase inhibitor, a Map kinase kinase (mek) inhibitor, a VEGF trap antibody, pemetrexed, erlotinib, dasatanib, nilotinib, decatanib, panitumumab, amrubicin, oregovomab, Lep-etu, nolatrexed, azd2171, batabulin, ofatumumab, zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL 13-PE38QQR, INO 1001, IPdR$_1$ KRX-0402, lucanthone, LY 317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, doxorubicin, liposomal doxorubicin, 5'-deoxy-5-fluorouridine, vincristine, temozolomide. ZK-304709, seliciclib; PD0325901, AZD-6244, capecitabine, L-Glutamic acid, N-[4-[2-(2-amino-4,7-dihydro-4-oxo-1H-pyrrolo[2,3-d]pyrimidin-5-yl)ethyl]benzoyl]-, disodium salt, heptahydrate, camptothecin, PEG-labeled irinotecan, tamoxifen, toremifene citrate, anastrazole, exemestane, letrozole, DES(diethylstilbestrol), estradiol, estrogen, conjugated estrogen, bevacizumab, IMC-1C11, CHIR-258); 3-[5-(methylsulfonylpiperadinemethyl)-indolylj-quinolone, vatalanib, AG-013736, AVE-0005, the acetate salt of [D-Ser(Bu t) 6,Azgly 10] (pyro-Glu-His-Trp-Ser-Tyr-D-Ser(Bu t)-Leu-Arg-Pro-Azgly-NH$_2$ acetate [C$_{59}$H$_{84}$N$_{18}$Oi$_4$ —(C$_2$H$_4$O$_2$)x where x=1 to 2.4], goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714; TAK-165, HKI-272, erlotinib, lapatanib, canertinib. ABX-EGF antibody, erbitux. EKB-569, PKI-166, GW-572016, Ionafamib, BMS-214662, tipifamib; amifostine, NVP-LAQ824, suberoyl analide hydroxamic acid, valproic acid, trichostatin A, FK-228, SU11248, sorafenib, KRN951, aminoglutethimide, amsacrine, anagrelide, L-asparaginase, Bacillus Calmette-Guerin (BCG) vaccine, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gemcitabine, hydroxyurea, idarubicin, ifosfamide, imatinib, leuprolide, levamisole, lomustine, mechlorethamine, melphalan, 6-mercaptopurine, mesna, methotrexate, mitormycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deoxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin diftitox, gefitinib, bortezimib, paclitaxel, cremophor-free paclitaxel, docetaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, topotecan, PTK787/ZK 222584, VX-745, PD 184352, rapamycin, 40-O-(2-hydroxyethyl)-rapamycin, temsirolimus, AP-23573, RAD001, ABT-578, BC-210. LY294002, LY292223, LY292696, LY293684, LY293646, wortmannin, ZM336372, L-779, 450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonists, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, erythropoietin, epoetin alfa, darbepoetin alfa, ipilimumab, nivolomuab, pembrolizumab, dabrafenib, trametinib and vemurafenib among others.

Co-administration of one of the formulations of the invention with another anticancer agent will often result in a synergistic enhancement of the anticancer activity of the other anticancer agent, an unexpected result. One or more of the present formulations comprising an AMPK modulator optionally in combination with a galectin 9 modulator and/or a TAK1 modulator and/or a lysosomotropic agent an autophagy modulator (autostatin) as described herein may also be co-administered with another bioactive agent (e.g., antiviral agent, antihyperproliferative disease agent, agents which treat chronic inflammatory disease, among others as otherwise described herein).

The term "antiviral agent" refers to an agent which may be used in combination with authophagy modulators (autostatins) as otherwise described herein to treat viral infections, especially including HIV infections, HBV infections and/or HCV infections. Exemplary anti-HIV agents include, for example, nucleoside reverse transcriptase inhibitors (NRTI), non-nucloeoside reverse transcriptase inhibitors (NNRTI), protease inhibitors, fusion inhibitors, among others, exemplary compounds of which may include, for example, 3TC (Lamivudine), AZT (Zidovudine), (−)-FTC, ddI (Didanosine), ddC (zalcitabine), abacavir (ABC), tenofovir (PMPA). D-D4FC (Reverset), D4T (Stavudine), Racivir, L-FddC, L-FD4C, NVP (Nevirapine), DLV (Delavirdine), EFV (Efavirenz), SQVM (Saquinavir mesylate), RTV (Ritonavir), IDV (Indinavir), SQV (Saquinavir), NFV (Nelfinavir), APV (Amprenavir), LPV (Lopinavir), fusion inhibitors such as T20, among others, fuseon and mixtures thereof, including anti-HIV compounds presently in clinical trials or in development. Exemplary anti-HBV agents include, for example, hepsera (adefovir dipivoxil), lamivudine, entecavir, telbivudine, tenofovir, emtricitabine, clevudine, valtoricitabine, amdoxovir, pradefovir, racivir, BAM 205, nitazoxanide, UT 231-B, Bay 41-4109, EHT899, zadaxin (thymosin alpha-1) and mixtures thereof. Anti-HCV agents include, for example, interferon, pegylated intergeron, ribavirin, NM 283, VX-950 (telaprevir), SCH 50304, TMC435, VX-500, BX-813, SCH503034, R1626, ITMN-191 (R7227), R7128, PF-868554, TT033, CGH-759, GI 5005, MK-7009, SIRNA-034, MK-0608, A-837093, GS 9190, ACH-1095, GSK625433, TG4040 (MVA-HCV), A-831, F351, NS5A, NS4B, ANA598, A-689, GNI-104, IDX102, ADX184, GL59728, GL60667, PSI-7851, TLR9 Agonist, PHX1766, SP-30 and mixtures thereof.

An "inflammation-associated metabolic disorder" includes, but is not limited to, lung diseases, hyperglycemic disorders including diabetes and disorders resulting from insulin resistance, such as Type I and Type II diabetes, as well as severe insulin resistance, hyperinsulinemia, and dyslipidemia or a lipid-related metabolic disorder (e.g. hyperlipidemia (e.g., as expressed by obese subjects), elevated low-density lipoprotein (LDL), depressed high-density lipoprotein (HDL), and elevated triglycerides) and insulin-resistant diabetes, such as Mendenhall's Syndrome, Weiner Syndrome, leprechaunism, and lipoatrophic diabetes, renal disorders, such as acute and chronic renal insufficiency, end-stage chronic renal failure, glomerulonephritis, interstitial nephritis, pyelonephritis, glomerulosclerosis, e.g., Kimmelstiel-Wilson in diabetic patients and kidney failure after kidney transplantation, obesity, GH-deficiency, GH resistance, Turner's syndrome, Laron's syndrome, short stature, increased fat mass-to-lean ratios, immunodeficiencies including decreased CD4$^+$ T cell counts and decreased immune tolerance or chemotherapy-induced tissue damage, bone marrow transplantation, diseases or insufficiencies of cardiac structure or function such as heart dysfunctions and congestive heart failure, neuronal, neurological, or neuromuscular disorders, e.g., diseases of the central nervous system including Alzheimer's disease, or Parkinson's disease or multiple sclerosis, and diseases of the peripheral nervous system and musculature including peripheral neuropathy, muscular dystrophy, or myotonic dystrophy, and catabolic states, including those associated with wasting caused by any condition, including, e.g., mental health condition (e.g., anorexia nervosa), trauma or wounding or infection such as with a bacterium or human virus such as HIV, wounds, skin disorders, gut structure and function that need restoration, and so forth.

An "inflammation-associated metabolic disorder" also includes a cancer and an "infectious disease" as defined herein, as well as disorders of bone or cartilage growth in children, including short stature, and in children and adults disorders of cartilage and bone in children and adults, including arthritis and osteoporosis. An "inflammation-associated metabolic disorder" includes a combination of two or more of the above disorders (e.g., osteoporosis that is a sequela of a catabolic state). Specific disorders of particular interest targeted for treatment herein are diabetes and obesity, heart dysfunctions, kidney disorders, neurological disorders, bone disorders, whole body growth disorders, and immunological disorders.

In one embodiment. "inflammation-associated metabolic disorder" includes: central obesity, dyslipidemia including particularly hypertriglyceridemia, low HDL cholesterol, small dense LDL particles and postpranial lipemia; glucose intolerance such as impaired fasting glucose; insulin resistance and hypertension, and diabetes. The term "diabetes" is used to describe diabetes mellitus type I or type II. The present invention relates to a method for improving renal function and symptoms, conditions and disease states which occur secondary to impaired renal function in patients or subjects with diabetes as otherwise described herein. It is noted that in diabetes mellitus type I and II, renal function is impaired from collagen deposits, and not from cysts in the other disease states treated by the present invention.

Mycobacterial infections often manifest as diseases such as tuberculosis. Human infections caused by mycobacteria have been widespread since ancient times, and tuberculosis remains a leading cause of death today. Although the incidence of the disease declined, in parallel with advancing standards of living, since the mid-nineteenth century, mycobacterial diseases still constitute a leading cause of morbidity and mortality in countries with limited medical resources. Additionally, mycobacterial diseases can cause overwhelming, disseminated disease in immunocompromised patients. In spite of the efforts of numerous health organizations worldwide, the eradication of mycobacterial diseases has never been achieved, nor is eradication imminent. Nearly one third of the world's population is infected with *Mycobacterium tuberculosis* complex, commonly referred to as tuberculosis (TB), with approximately 8 million new cases, and two to three million deaths attributable to TB yearly. Tuberculosis (TB) is the cause of the largest number of human deaths attributable to a single etiologic agent (see Dye et al., J. Am. Med. Association, 282, 677-686, (1999); and 2000 WHO/OMS Press Release).

Mycobacteria other than *M. tuberculosis* are increasingly found in opportunistic infections that plague the AIDS patient. Organisms from the *M. avium-intracellulare* complex (MAC), especially serotypes four and eight, account for 68% of the mycobacterial isolates from AIDS patients. Enormous numbers of MAC are found (up to $10^{10}$ acid-fast bacilli per gram of tissue), and consequently, the prognosis for the infected AIDS patient is poor.

In many countries the only measure for TB control has been vaccination with *M bovis* bacille Calmette-Guerin (BCG). The overall vaccine efficacy of BCG against TB, however, is about 50% with extreme variations ranging from 0% to 80% between different field trials. The widespread emergence of multiple drug-resistant *M. tuberculosis* strains is also a concern.

*M. tuberculosis* belongs to the group of intracellular bacteria that replicate within the phagosomal vacuoles of resting macrophages, thus protection against TB depends on T cell-mediated immunity. Several studies in mice and humans, however, have shown that Mycobacteria stimulate antigen-specific, major histocompatibility complex (MHC) class II- or class I-restricted CD4 and CD8 T cells, respectively. The important role of MHC class I-restricted CD8 T cells was convincingly demonstrated by the failure of D2-microglobulin) deficient mice to control experimental *M. tuberculosis* infection.

As used herein, the term "tuberculosis" comprises disease states usually associated with infections caused by mycobacteria species comprising *M. tuberculosis* complex. The term "tuberculosis" is also associated with mycobacterial infections caused by mycobacteria other than *M. tuberculosis*. Other mycobacterial species include *M. avium-intracellulare*, M. kansarii, *M. fortuitum, M. chelonae, M leprae. M. africanum*, and *M. microti, M. avium* paratuberculosis, *M. intracellulare, M. scrofulaceum, M. xenopi, M. marinum, M. ulcerans*.

An "infectious disease" includes but is limited to those caused by bacterial, mycological, parasitic, and viral agents. Examples of such infectious agents include the following: *staphylococcus, streptococcaceae, neisseriaaceae, cocci, enterobacteriaceae, pseudomonadaceae, vibrionaceae, campylobacter, pasteurellaceae, bordetella, francisella, brucella, legionellaceae, bacteroidaceae,* gram-negative *bacilli, clostridium, corynebacterium, propionibacterium*, gram-positive bacilli, anthrax, *actinomyces, nocardia, mycobacterium, treponema, borrelia, leptospira, mycoplasma, ureaplasma, rickettsia*, chlamydiae, systemic mycoses, opportunistic mycoses, protozoa, nematodes, trematodes, cestodes, adenoviruses, herpesviruses, poxviruses, papovaviruses, hepatitis viruses, orthomyxoviruses, paramyxoviruses, coronaviruses, picornaviruses, reoviruses, togaviruses, flaviviruses, bunyaviridae, rhabdoviruses, human immunodeficiency virus and retroviruses.

In certain embodiments, an "infectious disease" is selected from the group consisting of tuberculosis, leprosy, Crohn's Disease, aquired immunodeficiency syndrome, Lyme disease, cat-scratch disease, Rocky Mountain spotted fever and influenza or a viral infection selected from HIV (I and/or II), hepatitis B virus (HBV) or hepatitis C virus (HCV).

In certain embodiments, a disease state or condition in which fibrosis is a principal mechanism may be treated by compounds according to the present invention. In embodiments, an AMPK inhibitor and optionally a galectin 9 inhibitor and/or a TAK1 inhibitor in effective amounts is administered to a patient or subject for the treatment of a disease state or condition in which fibrosis is a principal mechanism. In embodiments, these disease states or conditions include fibrosis, such as pulmonary fibrosis, idiopathic pulmonary fibrosis, cystic fibrosis, fibrothorax, radiation-induced lung injury, bridging fibrosis, glial scarring, athrofibrosis, Dupuytren's contracture, keloid fibrosis, scleroderma/systemic sclerosis, adhesive capsulitis, mediastinal fibrosis, myelofibrosis, peyronie's disease, nephrogenic systemic fibrosis, progressive massive fibrosis, retroperitoneal fibrosis, cardiac fibrosis, (endo)myocardial fibrosis, interstitial fibrosis, replacement fibrosis, cirrhosis, non-alcohol fatty liver disease (NAFLD), non-alcoholic steatohepatitis (NASH), chronic kidney disease, stromal fibrosis and epidural fibrosis, among others. In preferred embodiments disease states or conditions which may be treated pursuant to this approach include cystic fibrosis, fibrolytic disesase states of the liver including cirrhosis and non-alcohol steatohepatitis (NASH) and other liver diseases including non-alcohol fatty liver disease (NAFLD) as well as cardiovascular disease states and numerous other conditions where impaired fibrinolysis and fibrosis is a causative component, such as coronary heart disease and vascular disease.

In embodiments, the AMPK antagonist is desomorphin (compound C), (S)-4-(2-(4-Amino-1,2,5-oxadiazol-3-yl)-1-ethyl-7-(piperidin-3-ylmethoxy)-1H-imidazo[4,5-c]pyridin-4-yl)-2-methylbut-3-yn-2-ol (GSK 690693), (±) Bay K 8644 or a pharmaceutically acceptable salt, stereoisomer or enantiomer thereof or a mixture thereof. In embodiments, the TAK1 inhibitor is dehydroabietic acid, NG25 (CAS No. 1315355-93-1), sarsasapogenin, takinib, 1-(3-(tert-Butyl)-1-(3-cyanophenyl)-1H-pyrazol-5-yl)-3-(3-methyl-4-(pyridin-4-yloxy)phenyl)urea (PF-05381941 or CAS No. 1474022-02-0), 5Z-7-oxozeaenol, TAK1-IN1, minnelide, triptolide or a pharmaceutically acceptable salt or mixture thereof. In embodiments, the galectin 9 inhibitor is as otherwise described herein.

According to various embodiments, the combination of compositions and/or compounds according to the present invention may be used for treatment or prevention purposes in the form of a pharmaceutical composition. This pharmaceutical composition may comprise one or more of an active ingredient as described herein.

As indicated, the pharmaceutical composition may also comprise a pharmaceutically acceptable excipient, additive or inert carrier. The pharmaceutically acceptable excipient, additive or inert carrier may be in a form chosen from a solid, semi-solid, and liquid. The pharmaceutically acceptable excipient or additive may be chosen from a starch, crystalline cellulose, sodium starch glycolate, polyvinylpyrolidone, polyvinylpolypyrolidone, sodium acetate, magnesium stearate, sodium laurylsulfate, sucrose, gelatin, silicic acid, polyethylene glycol, water, alcohol, propylene glycol, vegetable oil, corn oil, peanut oil, olive oil, surfactants, lubricants, disintegrating agents, preservative agents, flavoring agents, pigments, and other conventional additives. The pharmaceutical composition may be formulated by admixing the active with a pharmaceutically acceptable excipient or additive.

The pharmaceutical composition may be in a form chosen from sterile isotonic aqueous solutions, pills, drops, pastes, cream, spray (including aerosols), capsules, tablets, sugar coating tablets, granules, suppositories, liquid, lotion, suspension, emulsion, ointment, gel, and the like. Administration route may be chosen from subcutaneous, intravenous, intestinal, parenteral, oral, buccal, nasal, intramuscular, transcutaneous, transdermal, intranasal, intraperitoneal, and topical. The pharmaceutical compositions may be immediate release, sustained/controlled release, or a combination of immediate release and sustained/controlled release depending upon the compound(s) to be delivered, the compound(s), if any, to be coadministered, as well as the disease state and/or condition to be treated with the pharmaceutical composition. A pharmaceutical composition may be formulated with differing compartments or layers in order to facilitate effective administration of any variety consistent with good pharmaceutical practice.

The subject or patient may be chosen from, for example, a human, a mammal such as domesticated animal, or other animal. The subject may have one or more of the disease states, conditions or symptoms associated with autophagy as otherwise described herein.

The compounds according to the present invention may be administered in an effective amount to treat or reduce the likelihood of an autophagy-mediated disease and/or condition as well one or more symptoms associated with the disease state or condition. One of ordinary skill in the art would be readily able to determine an effective amount of active ingredient by taking into consideration several variables including, but not limited to, the animal subject, age, sex, weight, site of the disease state or condition in the patient, previous medical history, other medications, etc.

For example, the dose of an active ingredient which is useful in the treatment of an autophagy mediated disease state, condition and/or symptom for a human patient is that which is an effective amount and may range from as little as 100 µg or even less to at least about 500 mg or more, which may be administered in a manner consistent with the delivery of the drug and the disease state or condition to be treated. In the case of oral administration, active is generally administered from one to four times or more daily. Transdermal patches or other topical administration may administer drugs continuously, one or more times a day or less frequently than daily, depending upon the absorptivity of the active and delivery to the patient's skin. Of course, in certain instances where parenteral administration represents a favorable treatment option, intramuscular administration or slow IV drip may be used to administer active. The amount of active ingredient (including combinations of agents) which is administered to a human patient is an effective amount and preferably ranges from about 0.05 mg/kg to about 20 mg/kg, about 0.1 mg/kg to about 7.5 mg/kg, about 0.25 mg/kg to about 6 mg/kg., about 1.25 to about 5.7 mg/kg.

The dose of a compound according to the present invention may be administered at the first signs of the onset of an autophagy mediated disease state, condition or symptom. For example, the dose may be administered for the purpose of lung or heart function and/or treating or reducing the likelihood of any one or more of the disease states or conditions which become manifest during an inflammation-associated metabolic disorder or tuberculosis or associated disease states or conditions, including pain, high blood pressure, renal failure, or lung failure. The dose of active ingredient may be administered at the first sign of relevant symptoms prior to diagnosis, but in anticipation of the disease or disorder or in anticipation of decreased bodily function or any one or more of the other symptoms or secondary disease states or conditions associated with an autophagy mediated disorder to condition.

These and other aspects of the invention are described further in the following illustrative examples which are provided for illustration of the present invention and are not to be taken to limit the present invention in any way.

EXAMPLES

Figure 1S:
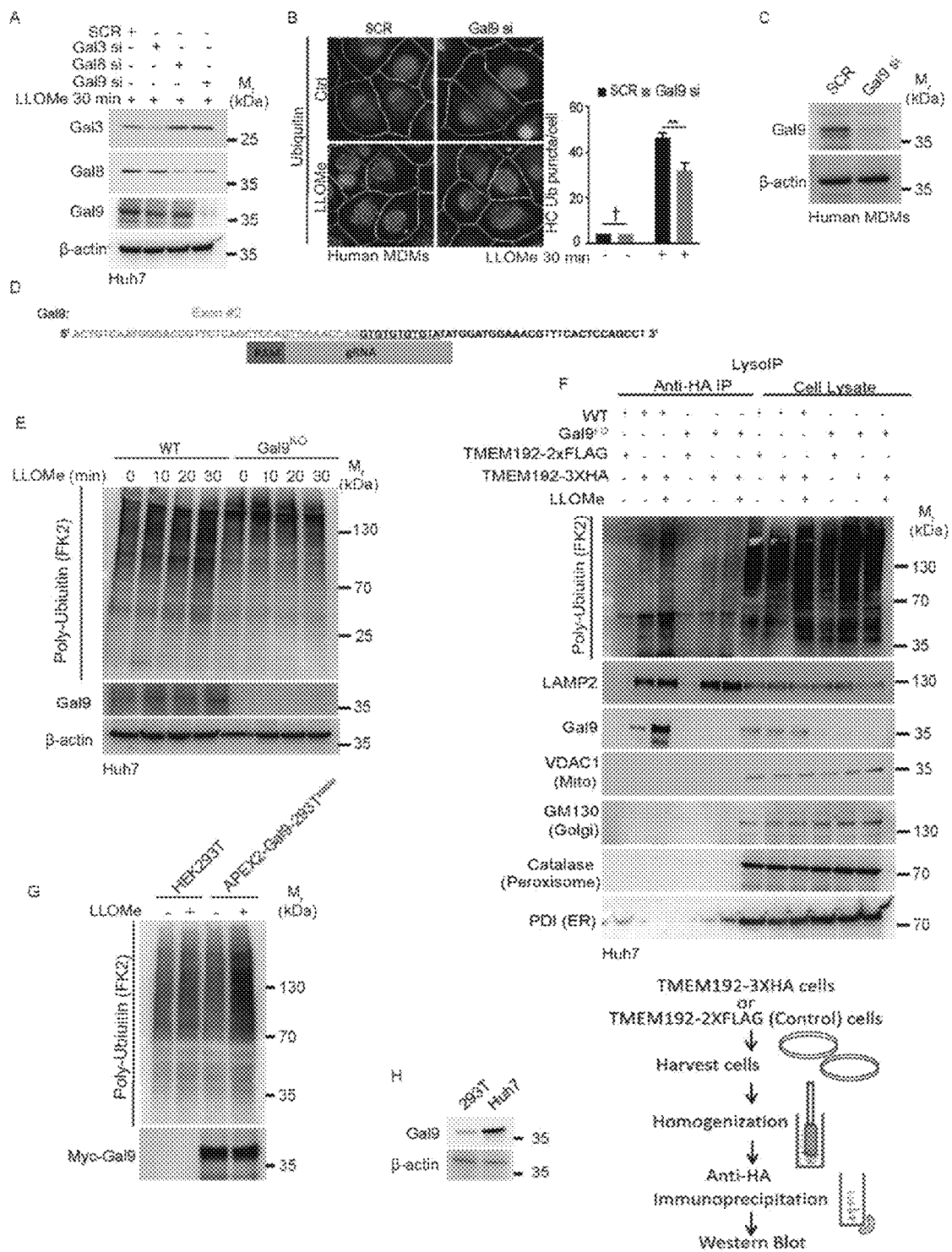
FIG. 1S, related to FIG. 1, shows the loss of Gal9 reduces lysosomal damage induced ubiquitination. (A) WB depicting knockdown of Gal3, Gal8 and Gal9 in Huh7. β-actin used as loading control. (B) Analysis of endogenous ubiquitin (Ub) puncta formation in human MDM cells transfected with respective siRNA and treated with lysosomal damaging agent (1 mM LLOMe) in full medium for 30 min, measured by HCM (high content microscopy) (blue: nuclei, Hoechst 33342; green: anti-FK2 antibody, Alexa-488). Cells transfected with scrambled siRNA as control (SCR). Ctrl, control untreated cells. White masks, computer algorithm-defined cell boundaries (primary objects); green masks, computer-identified ubiquitin puncta (target objects). (C) Western Blot (WB) analysis of Gal9 and β-actin in human MDM cells transfected with control siRNA (SCR) and Gal9 siRNA. (D) Schematic diagram for CRISPR/Cas9-mediated knockout of Gal9 in Huh7 cells. (E) WB analysis of Poly-ubiquitin (using anti-FK2) and β-actin in Gal9WT$^{Huh7}$ and Gal9KO$^{Huh7}$ treated with LLOMe in a time dependent manner. (F) Lysosome immunoprecipitation (LysoIP) analysis for indicated proteins in cell lysates or lysosomes purified from Gal9WT$^{Huh7}$ and Gal9KO$^{Huh7}$ cells subjected to 1 mM LLOMe treatment for 30 min. 2xFLAG-tagged TMEM192 were used as control. ER, endoplasmic reticulum. (G) WB analysis of Poly-ubiquitin (using anti-FK2) and myc-Gal9 in HEK293T and APEX2-Gal9-293T$^{stable}$ treated with LLOMe in full medium for 30 min. (H) WB analysis of endogenous expression level of Gal9 in HEK293T and Huh7 cells.

Results
Lysosomal Damage-Induced Ubiquitination Depends on Gal9
Lysosomal damage affects mTOR and AMPK, by inactivating the former and activating the latter (Jia et al., 2018). Both of these regulators represent master regulators of cellular metabolism (Garcia and Shaw, 2017; Hardie, 2011; Herzig and Shaw, 2018; Lin and Hardie, 2018; Saxton and Sabatini, 2017). In keeping with this, and likely including additional changes, lysosomal damage affected metabolism as indicated by metabolomic analyses (Table S1, Tab1). Here, we focused on the mechanism of how lysosomal damage activated AMPK. Lysosomal membrane damage induces both galectin and ubiquitin responses (Aits et al., 2015; Chauhan et al., 2016; Maejima et al., 2013; Papadopoulos et al., 2017). We wondered whether the two might be connected. There are three major galectin responders, Galectin 3 (Gal3), Gal8 and Gal9, to lysosomal (Aits et al., 2015; Chauhan et al., 2016; Jia et al., 2018; Maejima et al., 2013) and endolysosomal/phagosomal damage (Dupont et al., 2009a; Fujita et al., 2013, Garin et al., 2001; Paz et al., 2010; Thurston et al., 2012). Gal3, Gal8 and Gal9 form puncta on lysosomes when damage is inflicted by a panel of agents such as polymers of Leu-Leu-OMe (LLOMe) (Aits et al., 2015; Jia et al., 2018: Thiele and Lipsky, 1990), glycyl-L-phenylalanine 2-naphththylamide (GPN) (Berg et al., 1994) and silica (causing physical damage) (Jia et al., 2018; Maejima et al., 2013). Gal3, Gal8, and Gal9 show variable expression in different cell lines, which complicates comparative analysis. However, Huh7 liver adenocarcinoma cells display consistent endogenous expression of all three responder galectins, Gal3, Gal8, and Gal9. We tested whether knockdowns of galectins affected ubiquitination responses in Huh7 cells treated with LLOMe. No effect was observed with Gal3 and Gal8, however Gal9 knockdown reduced the ubiquitin response to LLOMe treatment as quantified by high content microscopy (HCM) (FIGS. 1A and 1SA). We confirmed these relationships in primary cells using human peripheral blood monocyte derived macrophages whereby Gal9 knockdown reduced the ubiquitin response (FIGS. 1SB and S1C). We further demonstrated this effect by generating a CRISPR Gal9 knockout in Huh7 cells (Gal9KO$^{Huh7}$) (FIGS. 1C and 1SD). Gal9KO$^{Huh7}$ cells showed diminished ubiquitin puncta formation in response to LLOMe (FIGS. 1B and 1C). Ubiquitin puncta were associated with lysosomes, and reduced ubiquitin expression and association with lysosomes was observed in Gal9KO$^{Huh7}$ cells (FIG. 1D). By immunobloting, we observed reduced levels of protein ubiquitination in whole cell lysates (FIG. 1SE). We confirmed diminished levels of ubiquitination in Gal9KO$^{Huh7}$ cells relative to WT Huh7 cells (Gal9WT$^{Huh7}$) in lysosomal preparations purified by LysoIP (Abu-Remaileh et al., 2017). In this assay, TMEM192-3xHA transfected cells are used to immunopurify lysosomal organelles on anti-HA beads, and, in parallel, TMEM192-2xFLAG transfected cells are used as a control for specificity of immunoisolation on anti-HA beads (FIG. 1SF). Thus, Gal9 is required for the ubiquitination response during lysosomal damage (FIG. 1E).

Proteomic Proximity Analysis of Gal9 During Lysosomal Damage

We next wanted to investigate interacting partners of Gal9 that may provide a clue regarding molecular machinery that allows Gal9 to control ubiquitination response to lysosomal damage. Our prior studies with APEX2-Gal8 proteomic analysis were performed in HEK293T cells using liquid chromatography tandem mass spectrometry (LC-MS/MS) in conjunction with proximity biotinylation with APEX2 (Jia et al., 2018). We thus generated a stable cell line expressing APEX2-myc-Gal9 in HEK293T (APEX2-Gal9-293T$^{stable}$) cells and subjected them to differential SILAC labeling and lysosomal damage employing LLOMe (FIG. 1F). Consistent with a positive role for Gal9 in the ubiquitination response to lysosomal damage, APEX2-Gal9-293T$^{stable}$ cells showed a robust ubiquitination response to LLOMe treatment in immunoblots relative to HEK293T cells, which normally display detectable but low levels of endogenous Gal9 (FIGS. 1SG and 1SH). Volcano plots of SILAC LC-MS/MS results quantifying alterations in the proximity of APEX2-Gal9 to cellular proteins (FIG. 1G) revealed dynamic changes upon lysosomal damage in a number of newly identified Gal9 interaction candidates, belonging to several recognizable functional groups: (i) integral lysosomal membrane proteins (e.g. LAMP1, LAMP2, SCARB/LIMP-2, VAMP7, TMEM192; showing increased association); (ii) lysosomal and other lipid metabolism proteins (NPC1, CDIPT/PIS, HSD17B10; displaying increased association); (iii) ubiquitin transactions proteins (TRIM25, VCP, USP7 and USP9X; showing damage-neutral or decreased association); (iv) ESCRT or ESCRT-related proteins (TSG101, PDCD6IP/ALIX, SRI; displaying decreased or damage-neutral association); (v) TORC1 regulators and mTOR effectors (LAMTOR1, EIF3L; showing increased or decreased associations); and (vi) a group of diverse partners (SYNCRIP, IMPDH2, a rate-limiting enzyme in the de novo guanine nucleotide biosynthesis, EZR, JUP/catenin, ACTN4/actinin, SEC24B/C; primarily with reduced associations).

APEX2-Gal9 showed strong proximity to integral membrane lysosomal proteins LAMP1, LAMP2, and TMEM192, as well as the SNARE protein VAMP7, all previously shown to be targeted by FBXO27, which is a glycan-recognizing component of the SCF (SKP1/CUL1/F-box protein) ubiquitin ligase complex (Yoshida et al., 2017). This result is consistent with Gal9 translocation to lysosomes after lysosomal damage, as previously reported in several cell lines (Aits et al., 2015: Jia et al., 2018; Thurston et al., 2012).

Gal9 Recruitment to Damaged Lysosomes Regulates Ubiquitination Response

Figure 2:
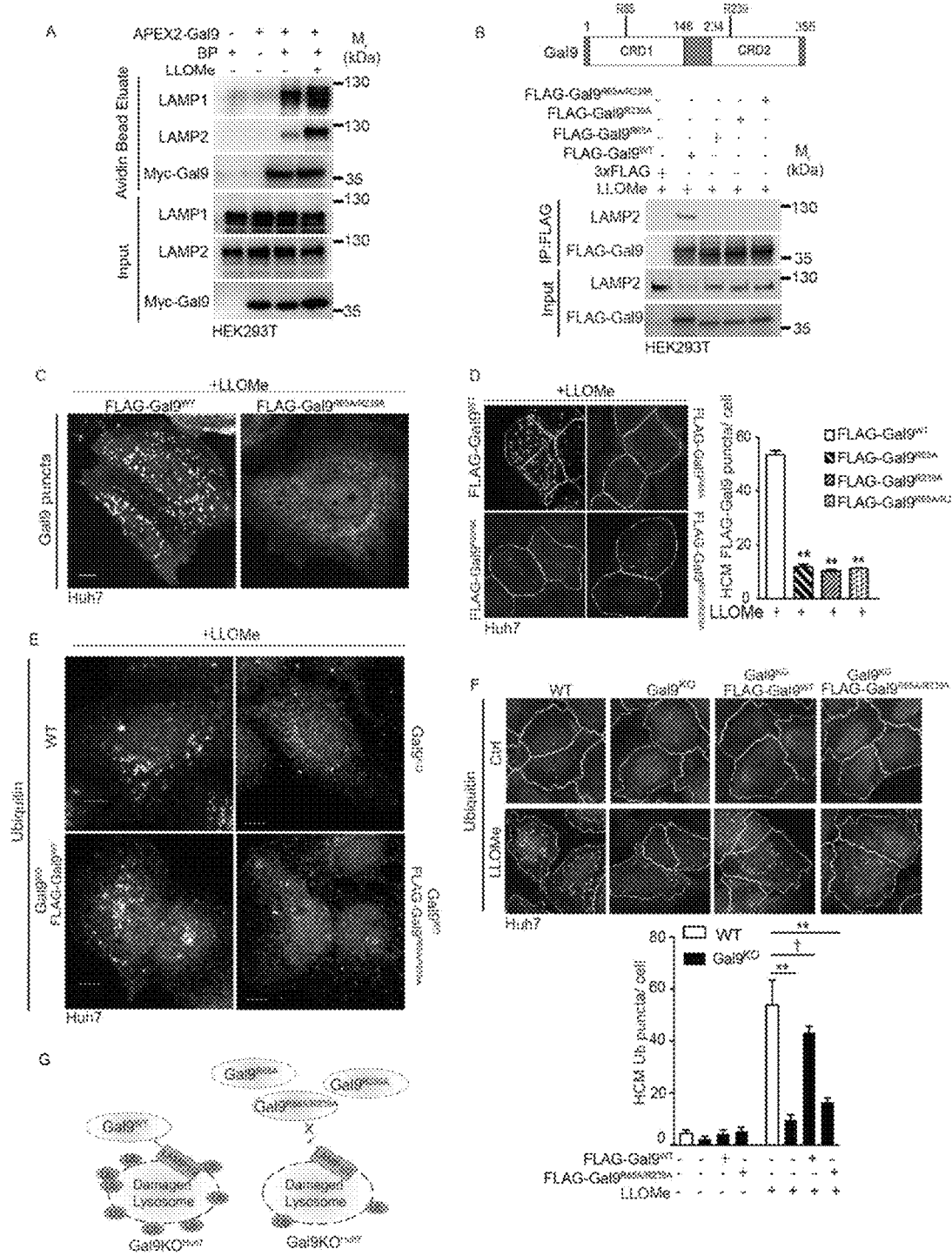
FIG. 2 shows that Gal9 recruitment to damaged lysosomes regulates ubiquitination response. (A) APEX2 proximity biotinylation analysis. HEK293T cells or APEX2-Gal9-293T$^{stable}$ cells which stably express APEX2-myc-Gal9 were incubated with or without biotin-phenol (BP); and pulsed with $H_2O_2$. Biotinylated proteins were then affinity-isolated on streptavidin beads and analyzed by immunoblotting in response to LLOMe. (B) Co-immunoprecipitation (Co-IP) analysis of interactions between LAMP2 and Gal9. HEK293T cells expressing FLAG-tagged Gal9 or glycan recognition mutant forms of Gal9 (individual R65A, R239A, or double/combined R65A/R239A were treated with 1 mM LLOMe for 30 min in full medium. IP, anti-FLAG antibody; immunoblotting with endogenous LAMP2. (C) Immunofluorescence confocal microscopy visualization of Gal9 puncta in Huh7 cells transfected with FLAG-Gal9$^{WT}$ or double mutant FLAG-Gal9$^{R65A/R239A}$ and treated with lysosomal damaging agent (1 mM LLOMe) in full medium for 30 min. Cells were immunostained for FLAG-Gal9. Scale bar, 10 µM. (D) Analysis of FLAG-Gal9 puncta formation in Huh7 WT cells transfected with FLAG-Gal9 and respective mutants. Cells as in (C) were treated as in (C), measured by HCM (blue: nuclei, Hoechst 33342; green: anti-FLAG antibody, Alexa-488). White masks, computer algorithm-defined cell boundaries; green masks, computer-identified Gal9 puncta. (E) Immunofluorescence confocal microscopy visualization of Ub puncta in Gal9WT$^{Huh7}$ and Gal9KO$^{Huh7}$ cells complemented with FLAG-Gal9$^{WT}$ or FLAG-Gal9$^{R65A/R239A}$ Treatment as in (D) and immunostained for endogenous Ub. Scale bar, 10 µM. (F) Endogenous Ub puncta quantified by HCM. Cells treatment as in (E). Ctrl, control untreated cells. White masks, computer algorithm-defined cell boundaries; green masks, computer-identified Ub puncta. (G) Schematic summary of the findings in FIG. 2 and S2. Data, means±SEM; immunoblots, n≥3; HCM, n≥3 (each experiment: 500 valid primary objects/cells per well, ≥5 wells/sample). † p≥0.05 (not significant), **p<0.01, ANOVA. See also Figure S2.
Figure 2S:
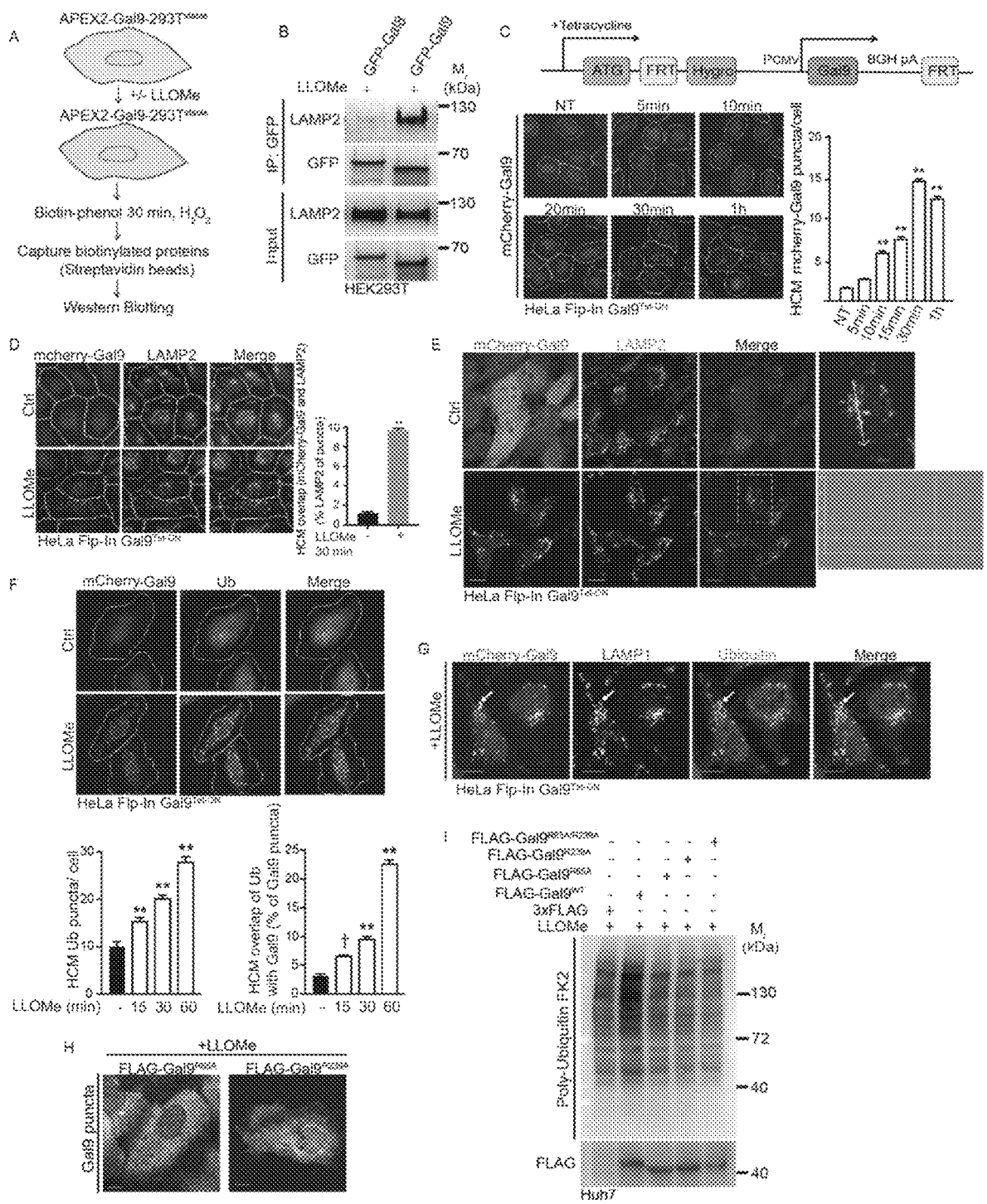
FIG. 2S, related to FIG. 2 shows that Gal9 mediated rescue of ubiquitination is dependent on glycosylation. (A) Schematic, strategy for APEX2-Gal9-293T$^{stable}$ Western blot analysis (see STAR Methods). (B) Co-IP analysis of galectins and LAMP2. Cells expressing GFP-tagged galectins were subjected to anti-GFP immunoprecipitation followed by immunoblotting for endogenous LAMP2. (C) Schematic, strategy for stable HeLa Flp-In Gal9$^{Tet-ON}$ which stably express mCherry-Gal9 induced by tetracycline. HeLa Flp-In Gal9$^{Tet-ON}$ cells treated with LLOMe in a time dependent manner quantified by HCM. (D) HCM visualization of mCherry-Gal9 localization relative to LAMP2-positive lysosomes. Cells as in (C) were treated with LLOMe for 30 min in full medium and immunostained for endogenous LAMP2 and mCherry Gal9. (E) Immunofluorescence confocal microscopy visualization of mCherry-Gal9 localization relative to LAMP2-positive lysosomes. Cells as in (D) immunostained for endogenous LAMP2 and mCherry Gal9. Scale bar, 10 µM. (F) HCM visualization of mCherry-Gal9 localization relative to endogenous Ub puncta. Cells as in (C) were treated with LLOMe for 30 min in full medium and immunostained for endogenous Ub and mCherry Gal9. (G) Immunofluorescence confocal microscopy visualization of mcherry-Gal9 localization relative to endogenous Ub and LAMP1-positive lysosomes. Cells as in (C) were treated with LLOMe for 30 min in full medium and immunostained for endogenous Ub, LAMP1 and mCherry Gal9. Scale bar, 10 µM. (H) Immunofluorescence confocal microscopy visualization of Gal9 puncta in Huh7 cells transfected with Gal9 mutants FLAG-Gal9$^{R65A}$ or FLAG-Gal9$^{R239A}$ and treated with lysosomal damaging agent (1 mM LLOMe) in full medium for 30 min. Cells were immunostained for FLAG-Gal9. Scale bar, 10 µM. (I) WB analysis of Poly-ubiquitin (using anti-FK2) in Gal9WT$^{Huh7}$ cells transfected with respective plasmids and treated with 1 mM LLOMe for 30 min. Data, means±SEM; immunoblots, n≥3; HCM, n≥3 (each experiment: 500 valid primary objects/cells per well, ≥5 wells/sample). † p≥0.05 (not significant), **p<0.01, ANOVA.

We confirmed proteomic data indicating possible interactions of LAMP1 and LAMP2 with Gal9 using APEX2-Gal9-293T$^{stable}$ cells and proximity biotinylation combined with affinity enrichment on Avidin beads and immunoblotting (FIGS. 2A and 2SA) and by co-IP between GFP-Gal9 and endogenous LAMP2 (FIG. 2SB). The interaction was specific for Gal9, as Gal8 did not co-IP with LAMP2 when compared to Gal9 (FIG. 2SB). The interaction between Gal9 and LAMP2 depended on the ability of Gal9 to recognize glycans exposed on lysosomal membranes following damage. When the two critical residues R65 and R239 in carbohydrate recognition domains 1 and 2 (CRD1 and CRD2) were mutated, previously shown to abrogate Gal9's ability to recognize β-galactoside-endowed glycoconjugates (Matsushita et al., 2000; Zhu et al., 2005), the association between mutant Gal9 and LAMP2 was lost relative to Gal9$^{WT}$ in co-IP experiments (FIG. 2B).

To analyze Gal9 response by microscopy, we generated an inducible (Tet-ON) stable cell line using the FLP-FRT recombination system (HeLa Flp-In Gal9$^{Tet-ON}$) and detected time-dependent Gal9 puncta formation as early as at 10 min with a maximum/plateau at 30 min-1 h (quantified by HCM; FIG. 2SC). The mCherry-Gal9 puncta overlapped with LAMP2, as quantified by HCM (FIG. 2SD) and observed by confocal microscopy (FIG. 2SE). The mCherry-Gal9 puncta also overlapped with ubiquitin dots elicited by LLOMe damage (FIG. 2SF). There was significant colocalization of the three markers (mCherry-Gal9, LAMP1 and ubiquitin dots) (FIG. 2SG). To test whether Gal9-puncta depended on glycan recognition, we compared FLAG-Gal9$^{WT}$ transfected-cells with FLAG-Gal9$^{R65A/R239A}$ mutant (FIG. 2C) and individual CRD mutants FLAG-Gal9$^{R65A}$ and FLAG-Gal9$^{R239A}$ and found that glycan-binding mutants lost the ability to form puncta upon lysosomal damage observed by confocal microscopy (FIGS. 2C and 2SH) and quantified by HCM (FIG. 2D).

We used Gal9 glycosylation mutants to test in complementation experiments whether this aspect of Gal9 was important for ubiquitin response to lysosomal damage. Using immunoblotting analysis of the ubiquitination response after 30 min incubation with LLOMe as in FIG. 1SE, complementation of Gal9KO$^{Huh7}$ cells was achieved. i.e. ubiquitination levels elicited by LLOMe treatment were restored, only with FLAG-Gal9$^{WT}$ but not with the FLAG-Gal9$^{R65A}$, FLAG-Gal9$^{R239A}$, or FLAG-Gal9$^{R65A/R239A}$ expression constructs (FIG. 2SI). In imaging experiments, FLAG-Gal9$^{R65A/R239A}$ mutant did not rescue emergence of ubiquitin puncta in response to lysosomal damage in Gal9KO$^{Huh7}$ cells whereas FLAG-Gal9$^{WT}$ did, as detected by confocal microscopy (FIG. 2E) and quantified by HCM (FIG. 2F).

We conclude that upon lysosomal membrane damage, Gal9 is recruited to lysosomes where it interacts with LAMPs (FIG. 2G) via exposed-glycan recognition by Gal9 CRDs, and potentially with additional glycosylated molecules such as integral membrane proteins LIMP-2/SCARB2 (Gonzalez et al., 2014) and TMEM192 (Liu et al., 2012). This binding is important for the positive role of Gal9 in the ubiquitination response to lysosomal damage.

Figure 3:
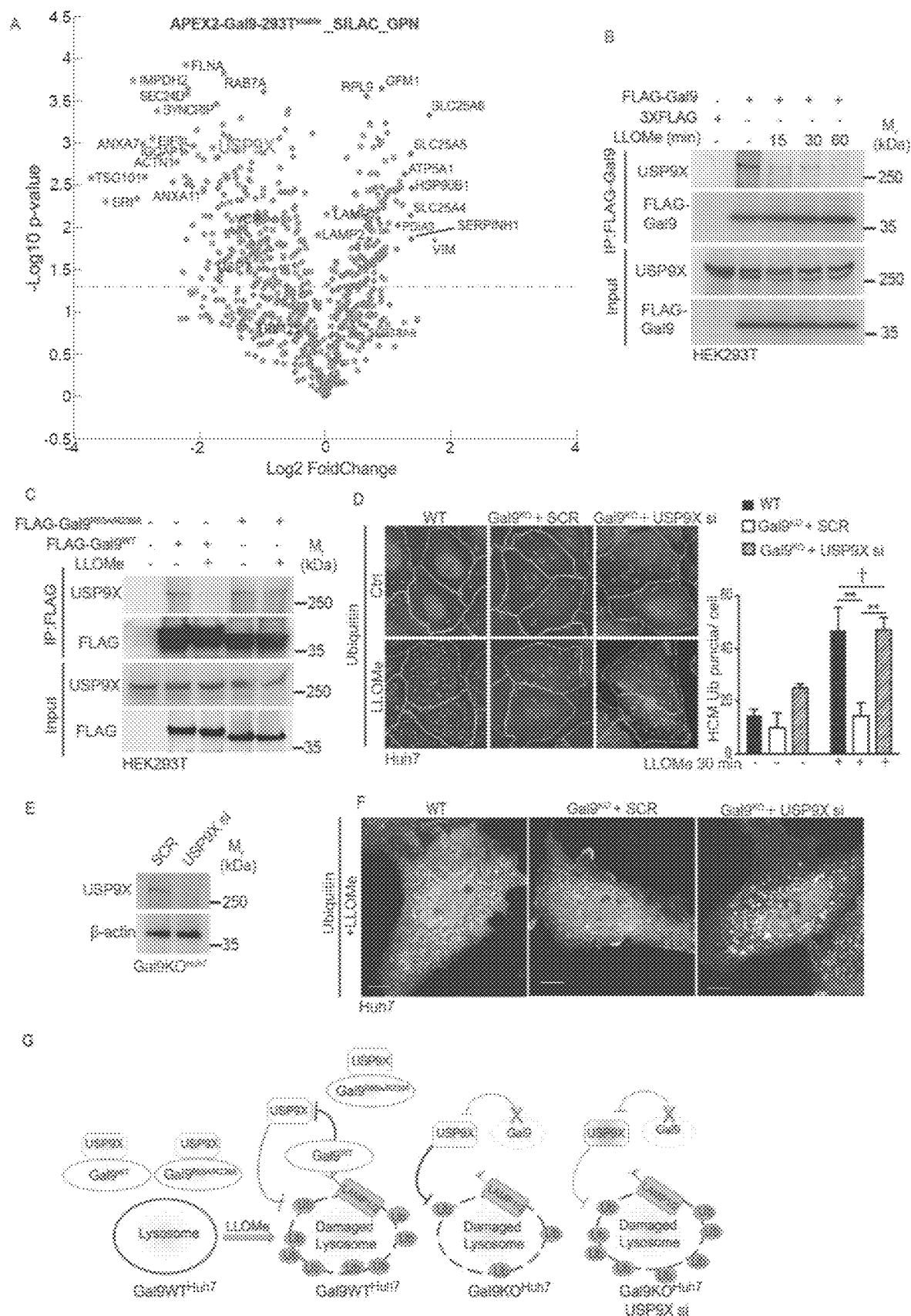
FIG. 3 shows that deubiquitinating enzyme USP9X is a Gal9 interactor and plays a role in ubiquitin response to lysosomal damage. (A) Volcano plot depicting dynamic changes in protein proximity relative to Gal9 in response to lysosomal damage caused by exposure to 100 µM GPN for 1 h, based on proteomic data in Table S1 (Tabs 2 and 4). Red circles, reduced interactions/proximities; Green circles, increased interactions/proximities (using Log 2 fold change) observed in at least two out of three complete biological replicates of APEX2-Gal9-293$^{stable}$ cells subjected to separate LC-MS/MS analyses. Blue stars, examples of proteins also identified in the LC-MS/MS analysis with 1 mM LLOMe treatment (see FIG. 1G). (B) Co-IP analysis of interactions between FLAG-Gal9$^{WT}$ and endogenous USP9X. HEK293T cells expressing FLAG-tagged Gal9 were treated with 1 mM LLOMe in full medium in time dependent manner. IP, anti-FLAG antibody; immunoblotting with endogenous USP9X. (C) Co-IP analysis of interactions between FLAG-Gal9$^{WT}$ or FLAG-Gal9$^{R65A/R239A}$ and endogenous USP9X. HEK293T cells expressing FLAG-tagged Gal9 or glycan recognition mutant forms of Gal9 were treated with 1 mM LLOMe in full medium for 30 min. IP, anti-FLAG antibody; immunoblotting with endogenous USP9X. (D) HCM analysis of endogenous Ub puncta formation in Gal9WT$^{Huh7}$ and Gal9KO$^{Huh7}$ cells transfected with respective siRNA and treated with 1 mM LLOMe in full medium for 30 min, measured by HCM (blue: nuclei, Hoechst 33342; green: anti-FK2 antibody, Alexa-488). Cells transfected with scrambled siRNA as control (SCR). Nonetreated cells were used as control (Ctrl). (E) WB analysis of USP9X and β-actin in Gal9KO$^{Huh7}$ cells. (F) Immunofluorescence confocal microscopy visualization of Ub puncta. Immunostained for endogenous Ub of cells as in (E). Scale bar, 10 μM. Data, means±SEM; immunoblots, n≥3; HCM, n≥3 (each experiment: 500 valid primary objects/cells per well, ≥5 wells/sample). † p≥0.05 (not significant), **p<0.01, ANOVA.

Deubiquitinating Enzyme USP9X is a Gal9 Effector and Plays a Role in Ubiquitin Response to Lysosomal Damage The lack of FBXO27 and other components of the SCF E3 ligase among Gal9 interactors suggests that Gal9 may employ a mechanism different than a simple recruitment of SCF$^{FBXO27}$ that in turn would increase ubiquitination elicited during lysosomal damage (Yoshida et al., 2017). To gain further insight, an additional proteomic proximity biotinylation analysis with APEX2-Gal9-293T$^{stable}$ cells was carried out using a different agent, GPN, titrated to cause only mild lysosomal damage (FIG. 3A). Albeit several differences were observed, a number of entities from the protein groups observed with LLOMe were found in proximity to Gal9. This included TSG101 and SRI of the ESCRT or ESCRT-related group, previously implicated in lysosomal damage repair (Skowyra et al., 2018), integral lysosomal proteins LAMP1 and LAMP2; ubiquitin transactions proteins including deubiquitinases (DUBs) USP7 (Pozhidaeva and Bezsonova, 2019) and USP9X (Paudel et al., 2019; Schwickart et al., 2010), a ubiquitin E3 ligase TRIM25 (Gack et al., 2007), and VCP, a part of the ELDR complex (p97/UBXD1/PLAA/YOD1) involved in remodeling of K48 ubiquitin chains on damaged lysosomes (Papadopoulos et al., 2017). Again, FBXO27 or other components of the SCF E3 ubiquitin ligase (Yoshida et al., 2017) were not found to be Gal9 interactors using GPN as in the case of LLOMe. Of the Gal9-effector candidates from overlaps between LLOMe and GPN proximity biotinylation proteomic analyses. TRIM25 did not show a change during lysosomal damage. VCP has previously been shown to play a role in removal of K48 ubiquitin chains on lysosomal substrates as a prelude to other events leading to lysosomal homeostasis (Arhzaouy et al., 2019). However, we did not find other components of the ELDR complex and thus focused on the DUBs identified in both LLOMe and GPN proximity biotinylation proteomic analyses. Of the two (USP7 and UPS9X), USP9X peptide counts were higher (20,27,26, in three experiments with GPN and 21,25,23 in LLOMe experiments) vs USP7 (3,4,3, in three experiments with GPN and 2,3,2 in LLOMe experiments) and Log 2 fold change for USP9X was greater in both LLOMe and GPN experiments and the p value for the change showed greater statistical significance (see volcano plots in FIGS. 1G and 3A and Table S1, Tabs 2-3). Thus we focused in subsequent experiments on USP9X, previously implicated in stabilization of a number of important substrates including Beclin 1 (Elgendy et al., 2014; Li et al., 2018), a regulator of autophagy (Levine and Kroemer, 2019), and in controlling activation of AMPK-related kinases (Al-Hakim et al., 2008).

Figure 3S:
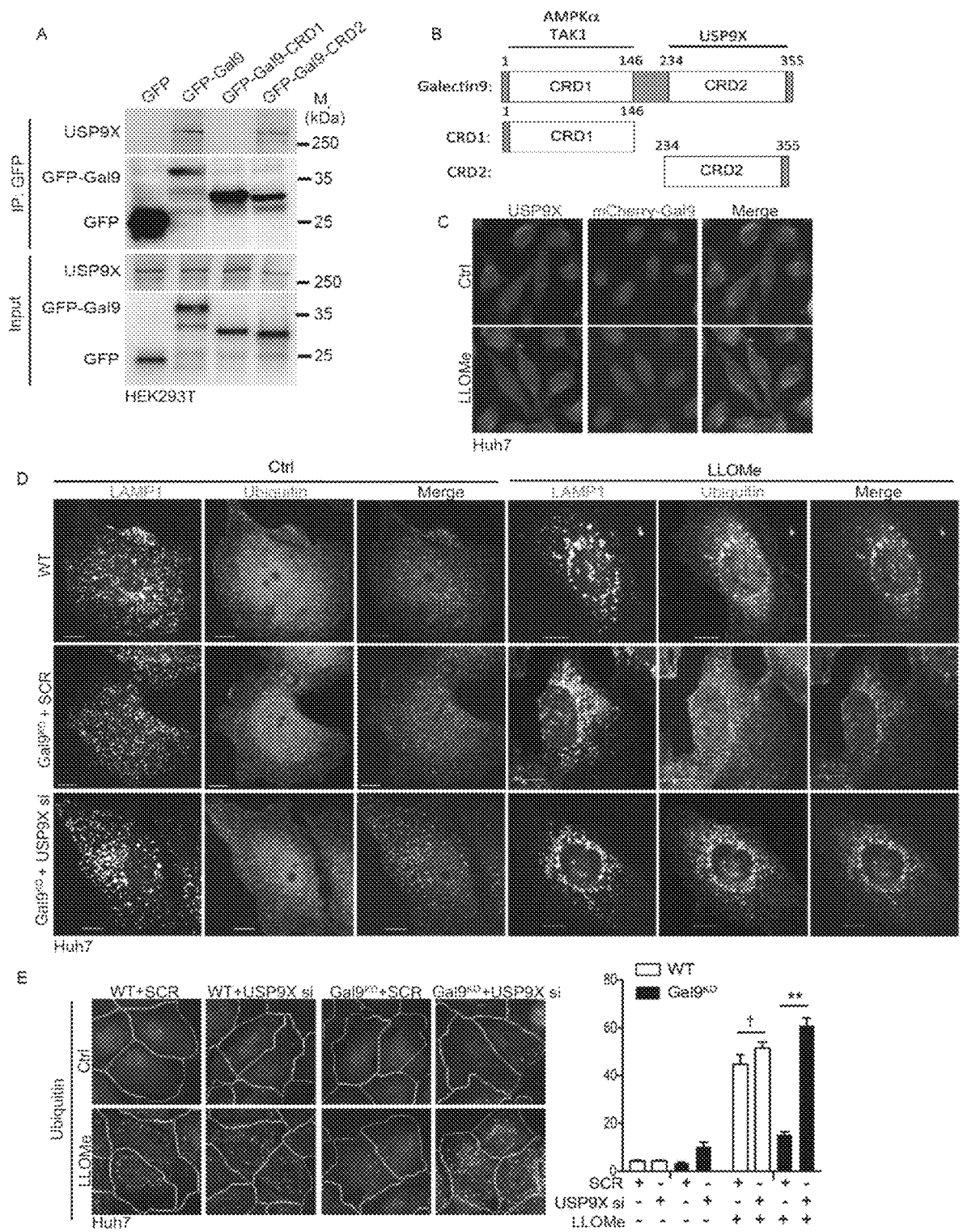
FIG. 3S, related to FIG. 3, shows that Gal9 and USP9X regulate ubiquitination response to lysosomal damage. (A) Co-IP analysis of interactions between GFP-Gal9 or deletion mutants GFP-Gal9-CRD1 and GFP-Gal9-CRD2 and endogenous USP9X. HEK293T cells expressing GFP-tagged Gal9 constructs were analyzed for endogenous USP9X binding. IP, anti-GFP antibody; immunoblotting with endogenous USP9X. (B) Schematic for Gal9 CRD domains and binding to respective proteins. (C) HCM visualization of mCherry-Gal9 localization relative to endogenous USP9X. Cells transfected with mCherry-Gal9 were treated with LLOMe for 30 min in full medium and immunostained for endogenous Ub and mCherry Gal9. None-treated cells were used as control (Ctrl). (D) Immunofluorescence confocal microscopy visualization of Ub localization relative to LAMP1-positive lysosomes. Cells transfected with respective siRNA were treated with LLOMe for 30 min in full medium and immunostained for endogenous LAMP1 (red florescence. Alexa-568) and Ub (green florescence, Alexa-488). None-treated cells were used as control (Ctrl). Scale bar, 10 µM. (E) HCM analysis of endogenous Ub puncta formation in Gal9WT$^{Huh7}$ and Gal9KO$^{Huh7}$ cells transfected with respective siRNA and treated with 1 mM LLOMe in full medium for 30 min, measured by HCM (blue: nuclei, Hoechst 33342; green: anti-FK2 antibody. Alexa-488). Cells transfected with scrambled siRNA as control (SCR). None-treated cells were used as control (Ctrl). Data, means±SEM; immunoblots, n≥3; HCM, n≥3 (each experiment: 500 valid primary objects/cells per well, ≥5 wells/sample). † p≥0.05 (not significant), **p<0.01, ANOVA.

We first confirmed that Gal9 and USP9X interacted and examined the dynamics of their interactions following lysosomal damage. FLAG-Gal9 and USP9X interacted in resting cells by co-IP (FIG. 3B). We mapped the interaction domain in Gal9 to its CRD2 by co-IP analyses between endogenous USP9X and the Gal9 constructs including GFP-Gal9 full size and deletion mutants GFP-Gal9-CRD1 and GFP-Gal9-CRD2 (FIGS. 3SA and 3SB). We observed decreased interactions between FLAG-Gal9 and USP9X upon treatment with LLOMe (FIG. 3B), in keeping with the results of dynamic proximity biotinylation proteomic analyses with LLOMe (FIG. 1G) and GPN (FIG. 3A) indicating that upon lysosomal damage Gal9 and USP9X separate from each other. USP9X did not form puncta either in resting or cells exposed to LLOMe, the latter being compatible with separation between Gal9 (which forms puncta upon lysosomal damage) and USP9X (which does not) (FIG. 3SC). The ability of Gal9 and USP9X to interact in resting cells was independent of the capacity of Gal9 to recognize exposed glycans, i.e. there was a similar level of interaction of FLAG-Gal9$^{WT}$ and FLAG-Gal9$^{R65A/R239A}$ with USP9X (FIG. 3C), indicating that Gal9 and USP9X interact under homeostatic conditions. However, the dissociation of USP9X from Gal9 complexes depended on the ability of Gal9 to recognize exposed glycoconjugates (FIG. 3C), indicating that exposure of glycans following lysosomal membrane damage and their recognition by Gal9 this acts as a signal promoting separation of Gal9 and USP9X. Thus, USP9X is a Gal9 interacting partner responsive to lysosomal damage (FIG. 3G).

We tested the role of USP9X in ubiquitin response to lysosomal damage. In Gal9KO$^{Huh7}$ cells, knocking down USP9X fully reversed ubiquitin puncta response to lysosomal damage (FIGS. 3D-F). The restored ubiquitin puncta overlapped with LAMP1 (FIG. 3SD). In wild type Huh7 cells, knockdown of USP9X did not have an effect on the ubiquitin puncta response (FIG. 3SE), suggesting that this USP9X phenotype is detected only in cells lacking Gal9 where ubiquitination is diminished. This indicates that in the absence of Gal9, USP9X acts to remove ubiquitin, but when Gal9 is present and can recognize membrane injury, Gal9 excludes USP9X and promotes the ubiquitination response to lysosomal damage (FIG. 3G).

Roles of Gal9, USP9X, and Ubiquitin Converge Upon TAK1, a Regulator of AMPK

Figure 4:
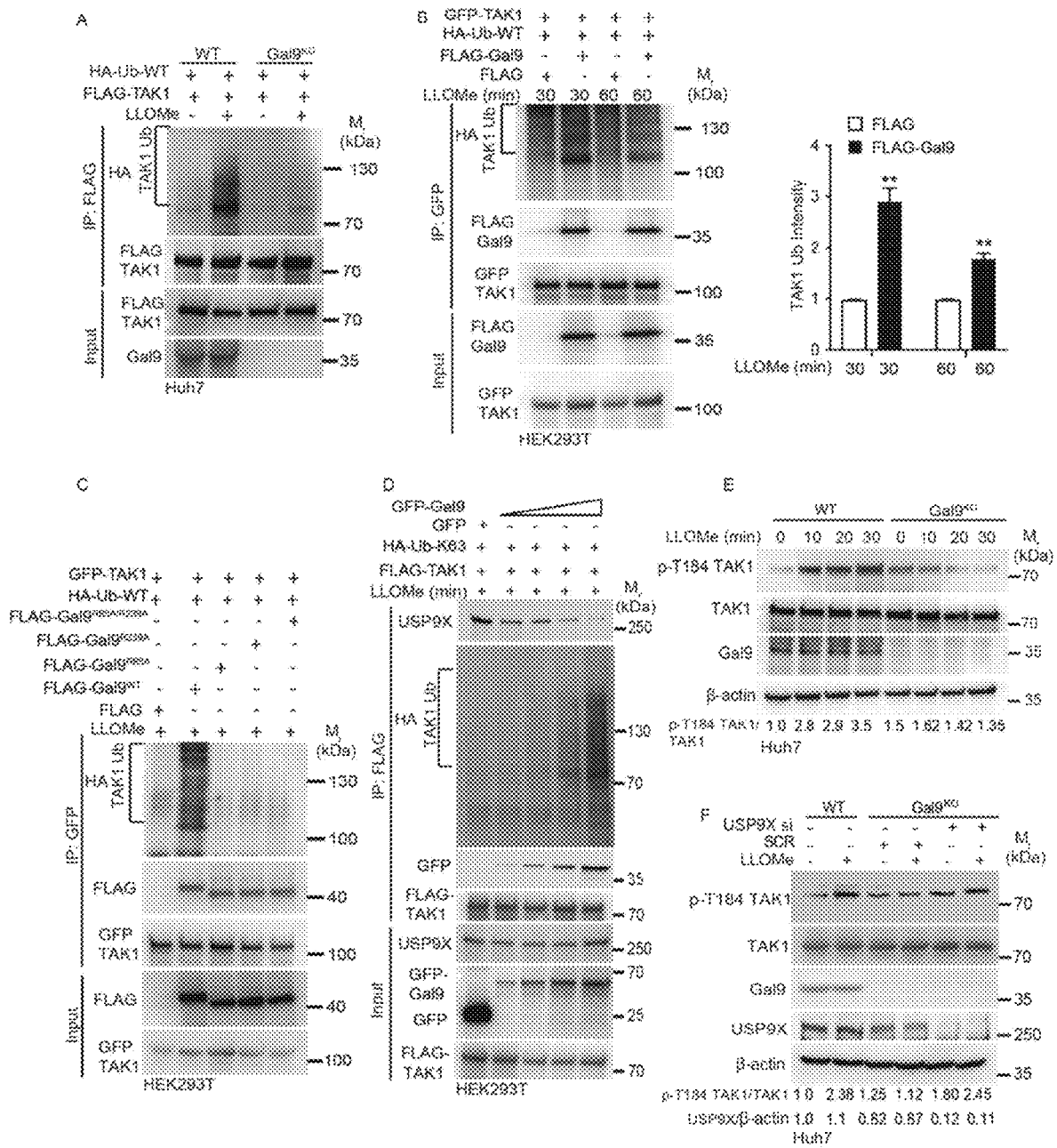
FIG. 4 shows the role of ubiquitin and USP9X in response to lysosomal damage converges upon TAK1, an upstream regulator of AMPK. (A) TAK1 ubiquitination analysis in Gal9WT$^{Huh7}$ and Gal9KO$^{Huh7}$ cells transfected with FLAG-TAK1 and HA-Ub-WT and treated with 1 mM LLOMe in full medium for 30 min. IP, anti-FLAG antibody; immunoblotting with anti-HA antibody. (B) TAK1 ubiquitination analysis in HEK293T cells transfected with GFP-TAK1, HA-Ub-WT and 3XFLAG or FLAG-Gal9 and treated with 1 mM LLOMe in full medium for 30 min or 60 min. IP, anti-GFP antibody; immunoblotting with anti-HA antibody and anti-FLAG antibody. Graph representing quantification of TAK1 ubiquitination. (C) TAK1 ubiquitination analysis in HEK293T cells transfected with GFP-TAK1, HA-Ub-WT and 3XFLAG or FLAG-Gal9$^{WT}$/FLAG-Gal9$^{R65A}$/FLAG-Gal9$^{R239}$/FLAG-Gal9$^{R65A/R239A}$ and treated with 1 mM LLOMe in full medium for 30 min. IP, anti-GFP antibody; immunoblotting with anti-HA antibody and anti-FLAG antibody. (D) Co-IP analysis of interactions between FLAG-TAK1 and endogenous USP9X and TAK1 K63 ubiquitination analysis in HEK293T cells transfected with FLAG-TAK1, HA-Ub-K63 and GFP or GFP-Gal9 in increasing amounts (0.5, 1, 2.5 and 5□g) and treated with 1 mM LLOMe in full medium for 30 min. IP, anti-FLAG antibody; immunoblotting with anti-USP9X, anti-HA antibody and anti-GFP antibody. (E) Western Blot analysis of phospho-TAK1 in Gal9WT$^{Huh7}$ and Gal9KO$^{Huh7}$ cells treated with 1 mM LLOMe in full medium in time dependent manner. Immunoblotting with anti-pT184-TAK1, anti-TAK1, anti-Gal9 and loading control anti-□-actin. (F) Western Blot analysis of phospho-TAK1 in Gal9WT$^{Huh7}$ and Gal9KO$^{Huh7}$ cells, with Gal9KO$^{Huh7}$ transfected with respective siRNA and treated with 1 mM LLOMe in full medium for 30 min. Immunoblotting as in (E) and with anti-USP9X. SCR, scrambled siRNA. Data, means±SEM; immunoblots, n≥3; HCM, n≥3 (each experiment: 500 valid primary objects/cells per well, ≥5 wells/sample). **p<0.01, ANOVA.
Figure 4S:
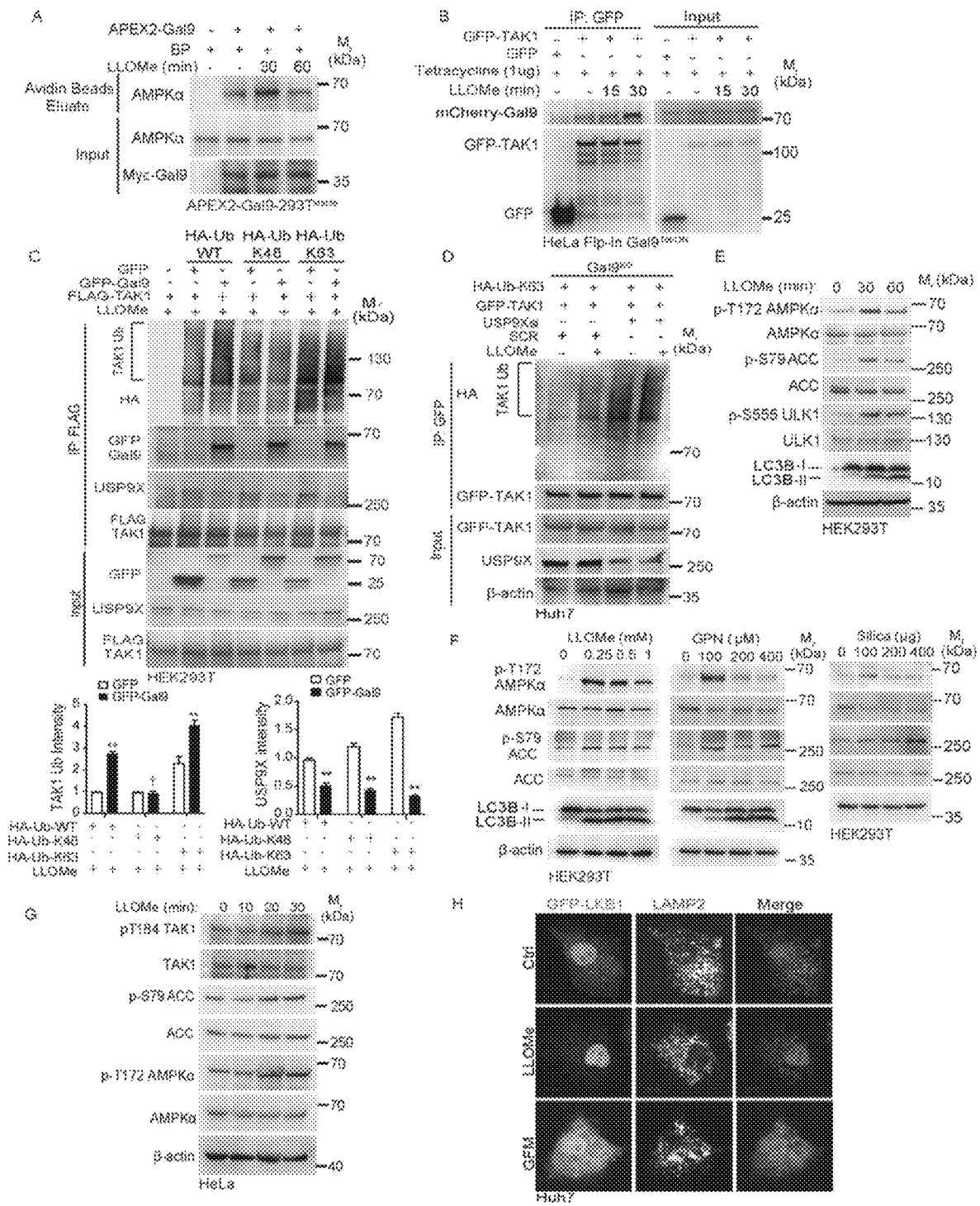
FIG. 4S, related to FIGS. 4 and 5, shows that Gal9 regulates TAK1 ubiquitination upon lysosomal damage. (A) APEX2 proximity biotinylation analysis. HEK293T cells expressing APEX2-Gal9 were incubated with biotin-phenol (BP); and pulsed with $H_2O_2$ and treated with 1 mM LLOMe in full medium for 30 min and 60 min. Biotinylated proteins were then affinity-isolated on streptavidin beads and analyzed by immunoblotting in response to LLOMe. (B) Co-IP analysis of interactions between GFP-TAK1 and mCherry-Gal9 in HeLa Flp-In-Gal9$^{Tet-ON}$ cells treated with tetracycline (1 ug) for 24 h and then treated with 1 mM LLOMe in full medium for 15 min and 30 min. IP, anti-GFP antibody; immunoblotting with anti-mCherry antibody. (C) TAK1 ubiquitination analysis in HEK293T cells transfected with FLAG-TAK1, GFP or GFP-Gal9 and either HA-Ub-WT, HA-Ub-K48 or HA-Ub-K63 and treated with 1 mM LLOMe in full medium for 30 min. IP, anti-FLAG antibody; immunoblotting with anti-HA antibody, anti-GFP antibody and anti-USP9X antibody. Graph representing quantification of TAK1 ubiquitination and USP9X levels. (D) TAK1 ubiquitination analysis in Gal9KO$^{Huh7}$ cells transfected with GFP-TAK1, HA-Ub-K63 and respective siRNA and treated with treated with 1 mM LLOMe in full medium for 30 mm. IP, anti-GFP antibody; immunoblotting with anti-HA antibody. SCR, scrambled siRNA. (E) Western Blot analysis of HEK293T cells treated with 1 mM LLOMe for respective time point. Immunoblotting was done with respective antibodies. (F) Western Blot analysis of HEK293T cells treated with different concentration of LLOMe, GPN or silica for 30 min. Immunoblotting was done with respective antibodies. (G) Western Blot analysis of HEK293T cells treated with 1 mM LLOMe for different time points. Immunoblotting was done with respective antibodies. (H) Immunofluorescence confocal microscopy visualization of GFP-LKB1 localization relative to LAMP2-positive lysosomes. Huh7 cells were treated with LLOMe for 30 min in full medium or Glucose free medium (GFM) for 1 h and immunostained for endogenous LAMP2 (red florescence, Alexa-568) and GFP-LKB1. Scale bar, 10 µM. Data, means±SEM; immunoblots, n≥3; HCM, n≥3 (each experiment: 500 valid primary objects/cells per well, ≥5 wells/sample). † p≥0.05 (not significant), **p<0.01, ANOVA.

Our recent studies have indicated that galectins display a broader role in signaling via mTOR and AMPK (Jia et al., 2018). Specifically, Gal9 was found in complexes with AMPK, and one of its upstream activating kinases TAK1, but whether these complexes respond to lysosomal damage has not been determined. We thus employed APEX2-Gal9 proximity biotinylation combined with affinity enrichment on Avidin beads and immunoblotting and detected increased association between AMPK and Gal9 at 30 min of exposure to LLOMe (FIG. 4SA). A similar increase in mCherry-Gal9 association with GFP-TAK1 was observed at 30 min of LLOMe treatment in HeLa Flp-In Gal9$^{Tet-ON}$ cells (FIG.

4SB). As shown above, Gal9 is important for ubiquitination in response to lysosomal damage whereas TAK1 is activated by K63 ubiquitination (Fan et al., 2010; Yang et al., 2015). TAK1 was ubiquitinated upon lysosomal damage, as detected in IPs of FLAG-TAK1 coexpressed with HA-tagged ubiquitin (FIG. 4A). Gal9 was critical for TAK1 ubiquitination, as evident by comparing Gal9KO$^{Huh7}$ vs WT Huh7 cells (FIG. 4A). When Gal9 was overexpressed in HEK293T cells, which have low levels of endogenous Gal9, this increased TAK1 ubiquitination, correlating with detection of Gal9 in protein complexes with GFP-TAK1 (FIG. 4B). We next tested a series of Gal9 mutants in CRD1, CRD2 or both, expressed as FLAG fusion constructs, which did not translocate to damaged lysosomes (FIGS. 2C and 2D) and could not rescue ubiquitination defect in Gal9KO$^{Huh7}$ (FIGS. 2E and 2F). We found that when overexpressed in HEK293T cells, FLAG-Gal9$^{R65A}$, FLAG-Gal9$^{239A}$ and FLAG-Gal9$^{R65A/R239A}$ did not support TAK1 ubiquitination, whereas FLAG-Gal9$^{WT}$ overexpressed in HEK293T did so in LLOMe-treated cells (FIG. 4C).

The endogenous DUB USP9X was detected in complexes with TAK1 using FLAG-TAK1 expressing 293T cells (FIG. 4D). In cells expressing increasing levels of Gal9, we observed a decrease in TAK1 association with USP9X, which correlated with Gal9 expression levels (FIG. 4D). This corresponded to increased K63 ubiquitination of TAK1 (FIG. 4D). We tested whether ubiquitination of TAK1 enhanced by Gal9 was K48 or K63 linked. For that we co-expressed GFP-Gal9 with either HA-K63-Ub, HA-K48-Ub, or HA-Ub (WT), and observed enhanced ubiquitination of TAK1 with WT and K63 ubiquitin but not with K48 ubiquitin (FIG. 4SC). The Gal9-induced dissociation of TAK1 and USP9X was detected in the same experiments (FIG. 4SC). This was reflected in TAK1 activation monitored by its phosphorylation at T184 (Liu et al., 2018; Yu et al., 2008), which increased upon lysosomal damage in Huh7 WT cells but showed a reverse trend in Gal9KO$^{Huh7}$ (FIG. 4E). Knocking down USP9X in Gal9KO$^{Huh7}$ cells rescued TAK1 activation, reflected in its K63 ubiquitination (FIG. 4SD) and pT184 phosphorylation (FIG. 4F). Thus, by interfering with USP9X, Gal9 is important for TAK1 ubiquitination and activation in response to lysosomal damage and specifically enhances K63 ubiquitination of TAK1, known to play a role in TAK1 activation (Li et al., 2011; Wang et al., 2001).

AMPK Activation During Lysosomal Damage Depends on TAK1

Figure 5:
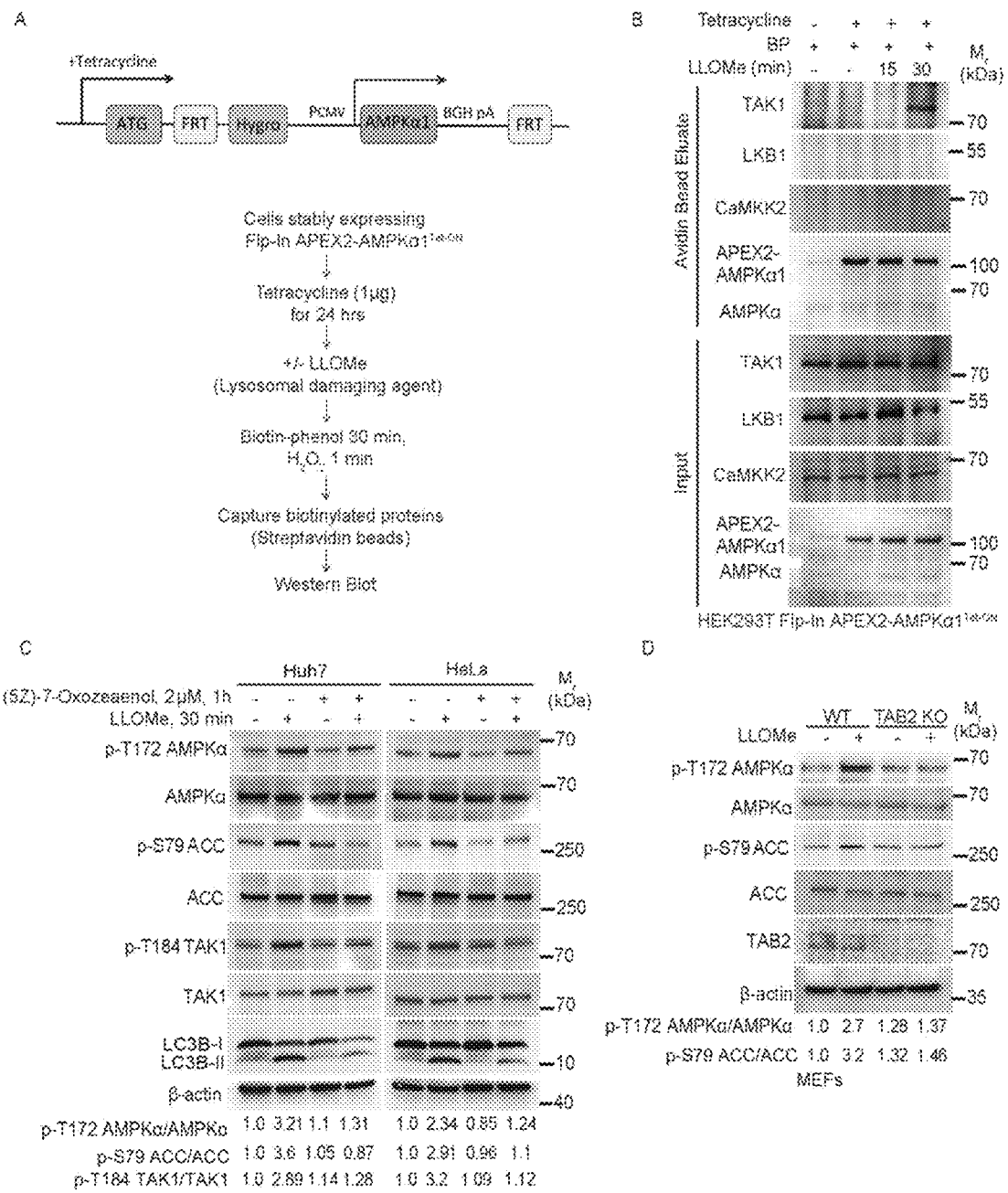
FIG. 5 shows that AMPK activation during lysosomal damage depends on TAK1 (A) Schematic, strategy of Western blot analysis for stable Flp-In APEX2-AMPKα1$^{Tet-ON}$ cells (see STAR Methods). (B) APEX2 proximity biotinylation analysis. HEK293T cells stably expressing Flp-In APEX2-AMPK□1$^{Tet-ON}$ were incubated with or without tetracycline (1 μg) for 24 h followed by incubation with biotin-phenol (BP); and pulsed with H$_2$O$_2$. The cells were treated with 1 mM LLOMe for 15 or 30 mm. Biotinylated proteins were then affinity-isolated on streptavidin beads and analyzed by immunoblotting for TAK1, LKB1 and CaMKK2. (C) Western Blot analysis of Huh7 and HeLa cells, treated with or without TAK1 inhibitor. (5Z)-7-Oxozeaenol and with 1 mM LLOMe in full medium for 30 min. Immunoblotting was done with respective antibodies. (D) Western Blot analysis of WT and TAB2 KO MEFs treated with 1 mM LLOMe in full medium for 30 min. Immunoblotting was done with respective antibodies. Data, means±SEM; immunoblots, n≥3; HCM, n≥3 (each experiment: 500 valid primary objects/cells per well, ≥5 wells/sample).

AMPK was activated upon lysosomal damage in a time and dose dependent manner, and when the injury was caused by various lysosomal damaging agents (LLOMe. GPN, and silica, a mechanical lysosome membrane damaging agent) (FIGS. 4SE-F). This was accompanied by similar responses in AMPK targets, ACC (pS79) (FIGS. S4E-F) and ULK1 (pS555) (FIG. 4SE). An increase in AMPK activation and activation of AMPK's substrate ACC as well as the upstream kinase TAK1 was observed in HeLa cells (FIG. 4SG). TAK1 is the only upstream activating kinase of AMPK previously identified in Gal9 complexes (Jia et al., 2018). We wondered whether TAK1 associated with AMPK and whether this was affected by lysosomal damage. This was addressed by using proximity biotinylation combined with affinity enrichment on Avidin beads and immunoblotting analysis. We generated a stable cell line expressing APEX2-AMPKα1 subunit in 293T cells (Flp-In APEX2-AMPKα1$^{Tet-ON}$; FIG. 5A). TAK1, but not LKB1 or CaMKK2, was detected in proximity of AMPKα1 in cells subjected to lysosomal damage (FIG. 5B). We next tested whether TAK1 inhibition affects AMPKα1 activation. Treatment of Huh7 cells with TAK1 inhibitor resorcylic lactone 5ZO ((5-Z)-7-oxozeaenol) (Okada et al., 2014; Wu et al., 2013) prevented AMPKα1 activation upon lysosomal damage. In Huh7 cells, LKB1 was sequestered in the nucleus and did not translocate to the cytoplasm on LLOMe treatment, although it was responsive to glucose starvation (FIG. 4SH). Furthermore, 5ZO suppressed TAK1 activation with LLOMe in HeLa cells, a cervical cancer-derived cell line notorious for downregulation or absence of LKB1 due to homozygous deletion affecting the LKB1 locus (McCabe et al., 2010) (FIG. 5C). This was accompanied by inhibition of phosphorylation of AMPK□1 (pT172), and its substrate ACC (pS79). Thus, TAK1 is likely responsible for the increase in AMPK activation by lysosomal damage. In addition to using TAK1 enzymatic inhibitors, we employed MEFs lacking TAB2 (TAK1-binding protein 2; TAB2 KO MEFs), an upstream ubiquitin-chain binding activator of TAK1 acting downstream of diverse signals (Criollo et al., 2011; Takaesu et al., 2012), and detected no increase in p172 AMPK□1 and pS79 ACC, although the matching WT TAB2 MEFs displayed an intact response to lysosomal damage (FIG. 5D). Collectively these data show that TAK1 is the kinase activating AMPK in response to lysosomal damage.

Activated AMPK Translocates to Lysosomes in a Gal9-Dependent Manner

Figure 6:
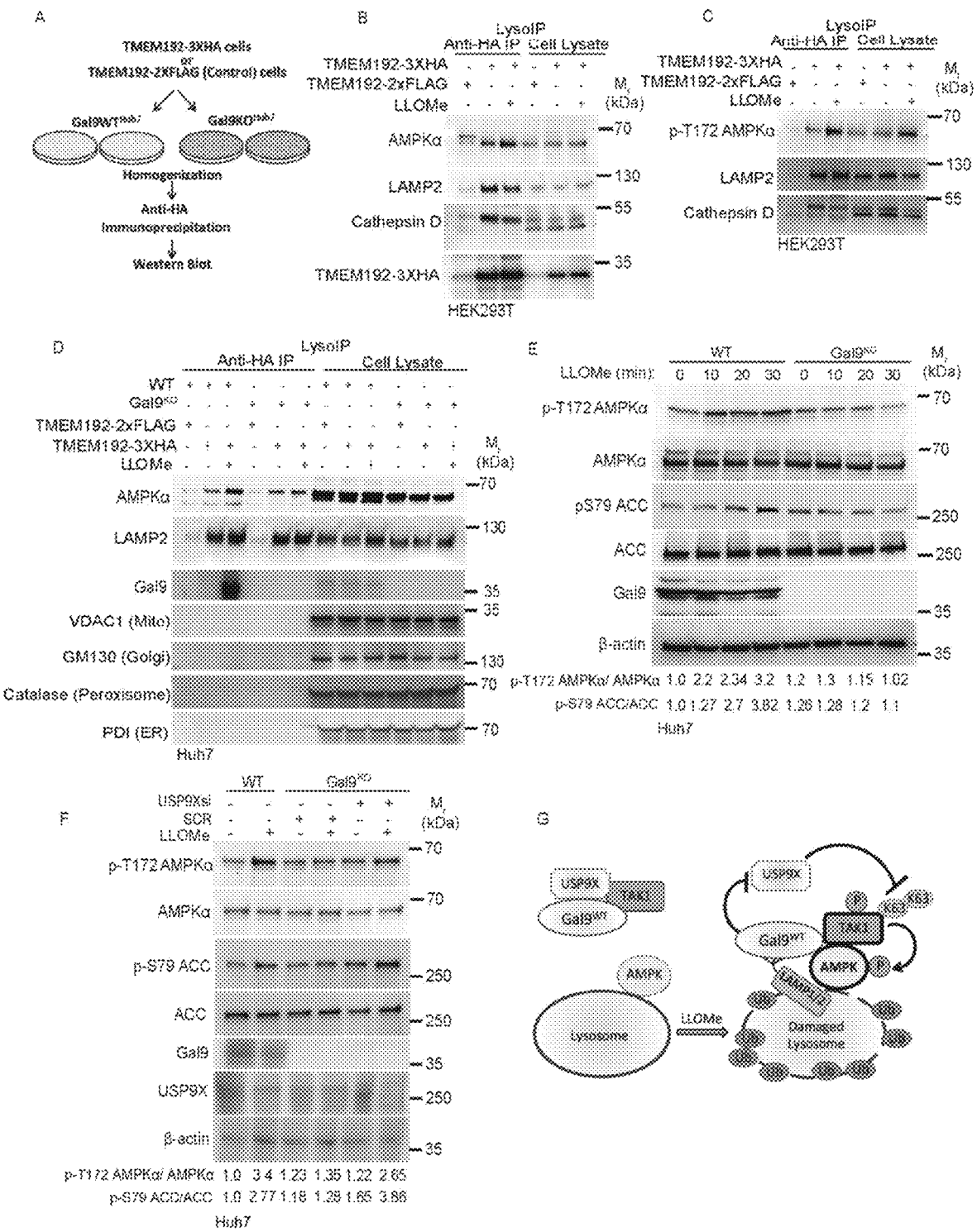
FIG. 6 shows that activated AMPK translocates to lysosomes in a Gal9-dependent manner. (A) Schematic for Lysosome immunoprecipitation (LysoIP) protocol. (B-C) Lyso-IP analysis for indicated proteins in cell lysates or lysosomes purified from HEK293T cells subjected to 1 mM LLOMe treatment for 30 min. FLAG-tagged TMEM192 were used as control. ER, endoplasmic reticulum. (D) LysoIP analysis for indicated proteins in cell lysates or lysosomes purified from Gal9WT$^{Huh7}$ and Gal9KO$^{Huh7}$ cells subjected to 1 mM LLOMe treatment for 30 min. FLAG-tagged TMEM192 were used as control. ER, endoplasmic reticulum. (E) Western Blot analysis in Gal9WT$^{Huh7}$ and Gal9KO$^{Huh7}$ cells treated with 1 mM LLOMe in full medium in time dependent manner. Immunoblotting with respective antibodies. □-actin used as loading control. (F) Western Blot analysis of in Gal9WT$^{Huh7}$ and Gal9KO$^{Huh7}$ cells, with Gal9KO$^{Huh7}$ transfected with respective siRNA and treated with 1 mM LLOMe in full medium for 30 min. Immunoblotting with respective antibodies. Quantification of expression is shown of three independent experiments. SCR, scrambled siRNA control. Data, means±SEM; immunoblots, n≥3; HCM, n≥3 (each experiment: 500 valid primary objects/cells per well, ≥5 wells/sample). (G) Shows a pictoral representation that Gal9 helps activate AMPK and recruits it to lysosomes following damage, whereas the DUB USP9X antagonizes AMPK activation.
Figure 5S:
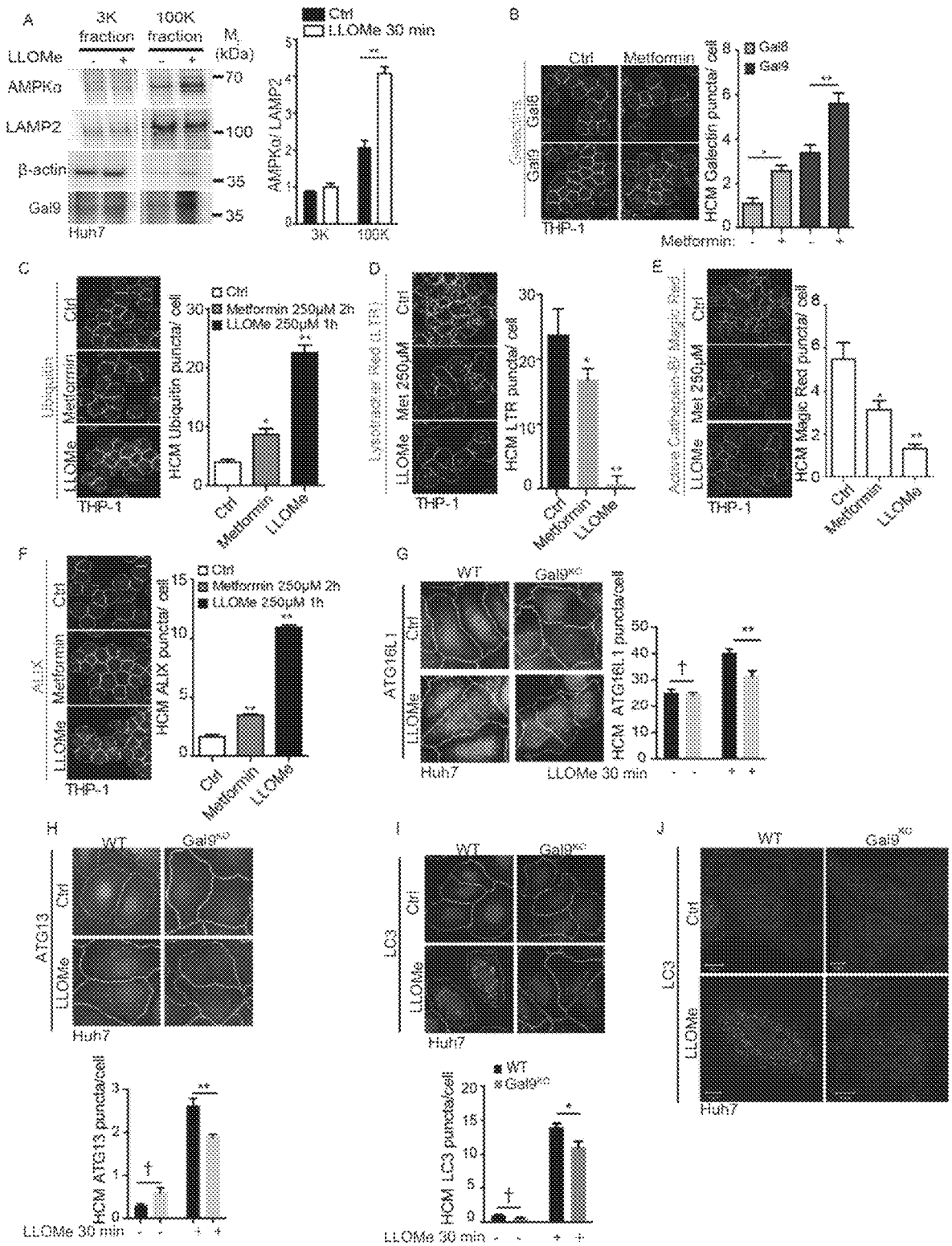
FIG. 5S, related to FIGS. 6 and 7 shows that metformin can cause lysosomal damage. (A) Differential centrifugation to obtain 3K, 100K fractions. Immunoblotting for AMPKα and LAMP2 on the membranes. Quantification to depict enrichment of AMPKα with respect to LAMP2 on the 100K membranes. (B) THP-1 cells were treated with 250 µM metformin for 2 h, and the average area of galectin puncta per cell was analyzed by HCM. White masks, algorithm defined cell boundaries (primary objects); green masks, computer-identified ubiquitin puncta (target objects). Ctrl, control untreated cells. (C) THP-1 cells were treated with 250 µM metformin for 2 h, or 250 µM LLOMe for 1 h, and the average area of ubiquitin puncta per cell was analyzed by HCM. White masks, algorithm defined cell boundaries; green masks, computer-identified ubiquitin puncta. Ctrl, control untreated cells. (D) THP-1 cells were treated with metformin 250 µM metformin for 2 h or 250 µM LLOMe for 1 h, and the average area of lysotracker puncta per cell was analyzed by HCM. White masks, algorithm defined cell boundaries; yellow masks, computer-identified lysotracker puncta. Ctrl, control untreated cells. (E) THP-1 cells were treated with metformin 250 µM metformin for 2 h or 250 µM LLOME for 1 h, and the average area of magic red puncta per cell was analyzed by HCM. White masks, algorithm defined cell boundaries; yellow masks, computer-identified magic red puncta. Ctrl, control untreated cells. (F) THP-1 cells were treated with 250 µM metformin for 2 h, or 250 µM LLOMe for 1 h, and the average area of ALIX puncta per cell was analyzed by HC. White masks, algorithm defined cell boundaries; green masks, computer-identified ALIX puncta. Ctrl, control untreated cells. (G-I) HCM analysis in Gal9WT$^{Huh7}$ and Gal9KO$^{Huh7}$ cells treated with 1 mM LLOMe in full medium for 30 min for (G) ATG16L1 puncta, (H) ATG13 puncta. (I) LC3 puncta, measured by HCM. White masks, algorithm defined cell boundaries, green masks, computer-identified (G) ATG16L1 or (H) ATG13 puncta, red masks, computer-identified (I) LC3 puncta. (J) Immunofluorescence confocal microscopy visualization of LC3 puncta. Cells as in (I) were treated with LLOMe for 30 min in full medium and immunostained for endogenous LC3 (red florescence, Alexa-568). Ctrl, control untreated cells. Scale bar, 10 µM. Data, means±SEM; immunoblots, n≥3; HCM, n≥3 (each experiment: 500 valid primary objects/cells per well, ≥5 wells/sample). † p≥0.05 (not significant), *p<0.05, **p<0.01, ANOVA.

Using the LysoIP lysosome purification strategy (Abu-Remaileh et al., 2017) (FIGS. 1SF and 6A), we detected enrichment of AMPKα1 on lysosomes in cells treated with LLOMe (FIG. 6B). AMPK enrichment on membranes was also detected in 100 k pellets positive for LAMP2 obtained after differential centrifugation at 3K, 25 k and 100 k (FIG. 5SA). Lysosomal AMPK detected by LysoIP was in activated state (pT172-AMPK□1; FIG. 6C). The translocation of AMPK to damaged lysosomes depended on Gal9, because there was less enrichment of AMPKα1 on lysosomes in Gal9KO$^{Huh7}$ then in their parental Huh7 Gal9 WT cells (FIGS. 6A and 6D). AMPK activation and phosphorylation of its target ACC depended on Gal9 (comparing Gal9KO$^{Huh7}$ and parental Gal9WT$^{Huh7}$ cells) (FIG. 6E). Furthermore, the absence of AMPK and ACC activation in Gal9KO$^{Huh7}$ was reversed by USP9X knockdown (FIG. 6F). In conclusion, Gal9 helps activate AMPK and recruits it to lysosomes following damage whereas the DUB USP9X antagonizes AMPK activation (FIG. 6G).

Metformin can Cause Lysosomal Damage

Metformin is a known AMPK inducer and a widely used antidiabetic drug believed to work by affecting AMP levels through inhibition of complex 1 of the mitochondrial electron transport chains (Foretz et al., 2014). However, its precise mode of action remains unclear (He and Wondisford, 2015). Recent studies (Zhang et al., 2016) have shown that metformin can induce AMPK through a lysosomal pathway involving AXIN and LKB1. We thus wondered whether metformin may affect lysosomal membrane integrity. Observable effects of metformin on cells are highly dependent on its transport and higher concentrations are often used experimentally (He and Wondisford, 2015) including 2 mM for 12 h (Zhang et al., 2016). We used a macrophage cell line THP-1 (Huh7 or 293T cells did not respond) with 250 μM metformin for 2 h and observed a lysosomal damage response by detecting Gal9 puncta formation (FIG. 5SB). We furthermore saw an increase in puncta stained for Gal8, another galectin known to respond to lysosomal damage (Aits et al., 2015; Jia et al., 2018) (FIG. 5SB). We next detected a ubiquitination response albeit of a lesser magnitude than when applying an overt lysosomal damaging agent LLOMe (FIG. 5SC). Evidence of lysosomal damage was also detected by a decrease in staining with the acidotropic fluorescent dye LysoTracker Red, which is normally trapped in acidified compartments such as lysosomes (FIG. 5SD). Furthermore, the number of puncta positive for MagicRed, a fluorescent reporter for lysosomal cathepsin B activity, was reduced (FIG. 5SE). Finally, we tested a recently reported marker of mild lysosomal membrane damage, ALIX, which is a component of ESCRT machinery involved in lysosomal damage repair (Radulovic et al., 2018; Skowyra et al., 2018). ALIX showed a robust response to LLOMe, and a milder but significant response to metformin (FIG. 5SF). We conclude that metformin is capable of causing lysosomal damage, which, as shown in the above sections, can induce AMPK.

Gal9 and USP9X Regulate Autophagy Induction in Response to Lysosomal Damage

Figure 7:
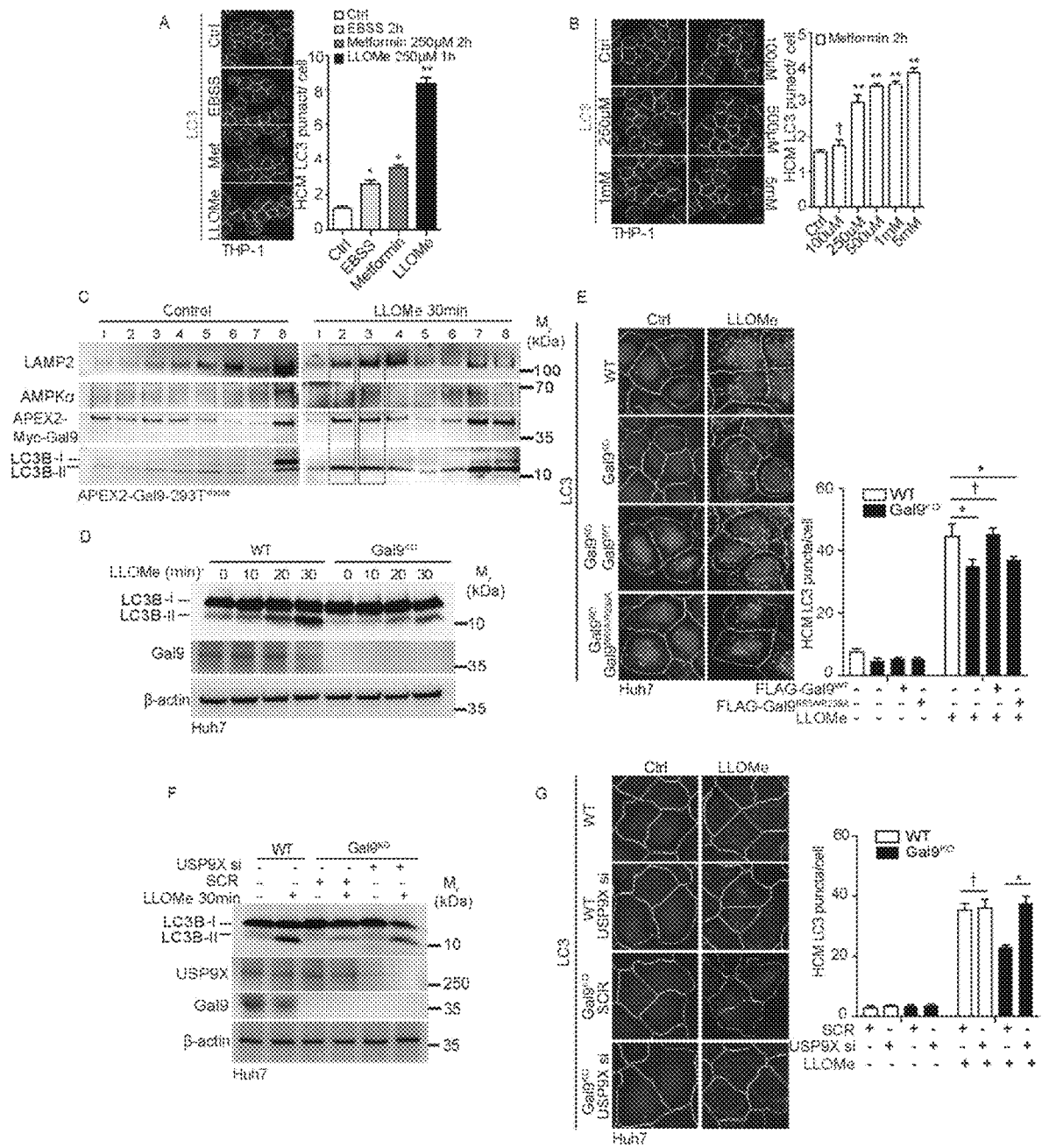
FIG. 7 shows that Gal9 and USP9X regulate autophagy response to lysosomal damage. (A) THP-1 cells were treated with EBSS and 250 μM metformin for 2 h, and 250 μM LLOMe for 1 h, and the average area of LC3 puncta per cell was analyzed by HCM. Ctrl, control untreated cells. White masks, algorithm defined cell boundaries (primary objects); green masks, computer-identified LC3 puncta (target objects). (B) THP-1 cells were treated with metformin as indicated dose for 2 h, and the average area of LC3 puncta per cell was analyzed by automated high-content imaging and analysis (HCM). Ctrl, control untreated cells. White masks, algorithm defined cell boundaries; green masks, computer-identified LC3 puncta. (C) WB analysis of proteins in membrane fractions from OptiPrep gradients (1-8 fractions, light to heavy; see the Membrane fractionation section of Materials and methods for details). (D) Western Blot analysis in Gal9WT$^{Huh7}$ and Gal9KO$^{Huh7}$ cells treated with 1 mM LLOMe in full medium in time dependent manner. Immunoblotting with respective antibodies. □-actin used as loading control. (E) HCM visualization of LC3 puncta. Cells transfected with Gal9$^{WT}$ or its mutant Gal9$^{R65A/R239A}$, were treated with LLOMe for 30 min in full medium and the average area of LC3 puncta per cell was analyzed by HCM. White masks, algorithm defined cell boundaries; green masks, computer-identified LC3 puncta. (F) Western Blot analysis of in Gal9WT$^{Huh7}$ and Gal9KO$^{Huh7}$ cells, with Gal9KO$^{Huh7}$ transfected with respective siRNA and treated with 1 mM LLOMe in full medium for 30 min. Immunoblotting with respective antibodies (G) HCM visualization of LC3 puncta. Cells as in (F) were treated with LLOMe for 30 min in full medium and the average area of LC3 puncta per cell was analyzed by HCM. White masks, algorithm defined cell boundaries; red masks, computer-identified LC3 puncta. Data, means±SEM; immunoblots, n≥3; HCM, n≥3 (each experiment: 500 valid primary objects/cells per well, ≥5 wells/sample). † p≥0.05 (not significant). *p<0.05, **p<0.01, ANOVA.
Figure 8:
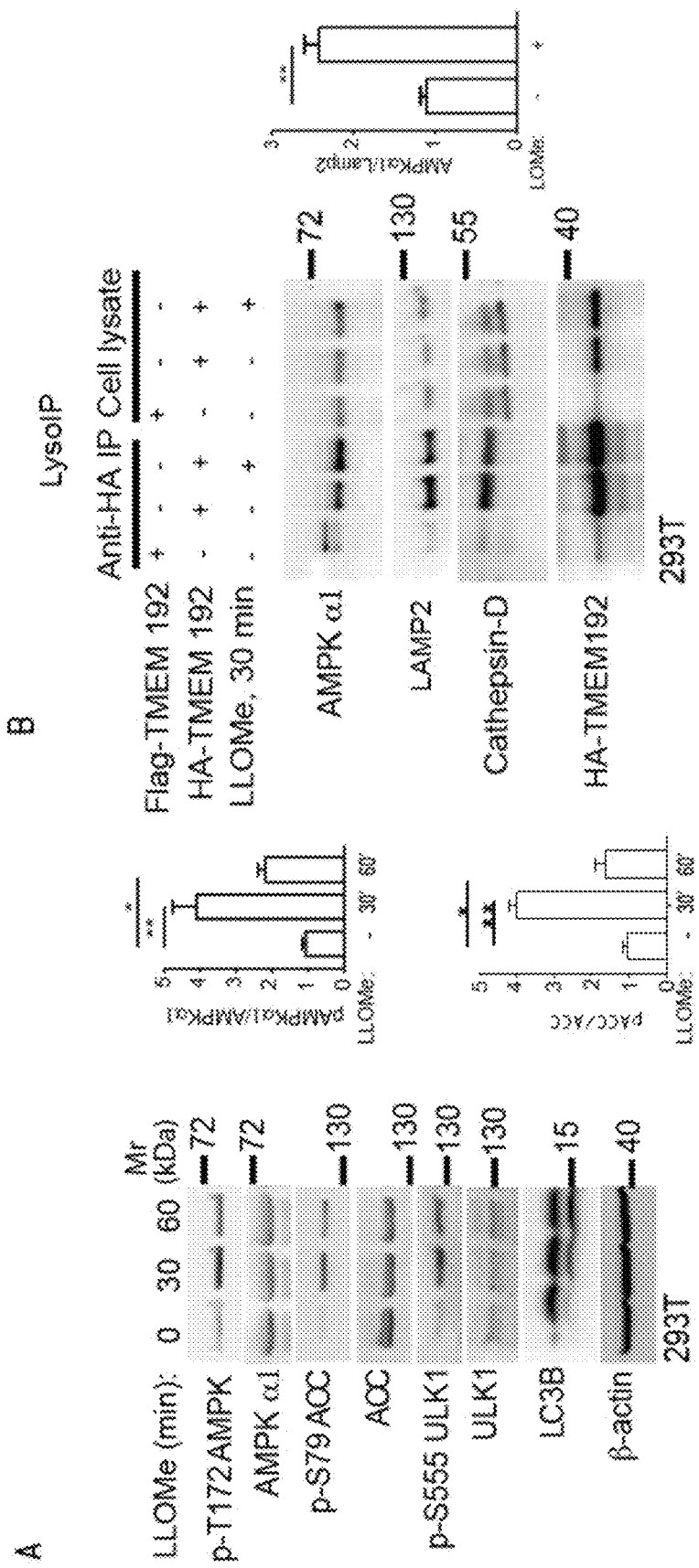
FIG. 8 shows that lysosomal damage induces AMPK activation and translocation to damaged lysosomes. (A) Western blot representing AMPK pathway activation upon lysosomal damage by LLOMe treatment. (B) Lysosomes are isolated by LysoIP method using HA-TMEM192. Lysosomal damage by LLOMe results in increased AMPK at the damaged lysosomes. The blots are probed for HA-TMEM192 and lysosome markers LAMP2 and Cathepsin D.
Figure 9:
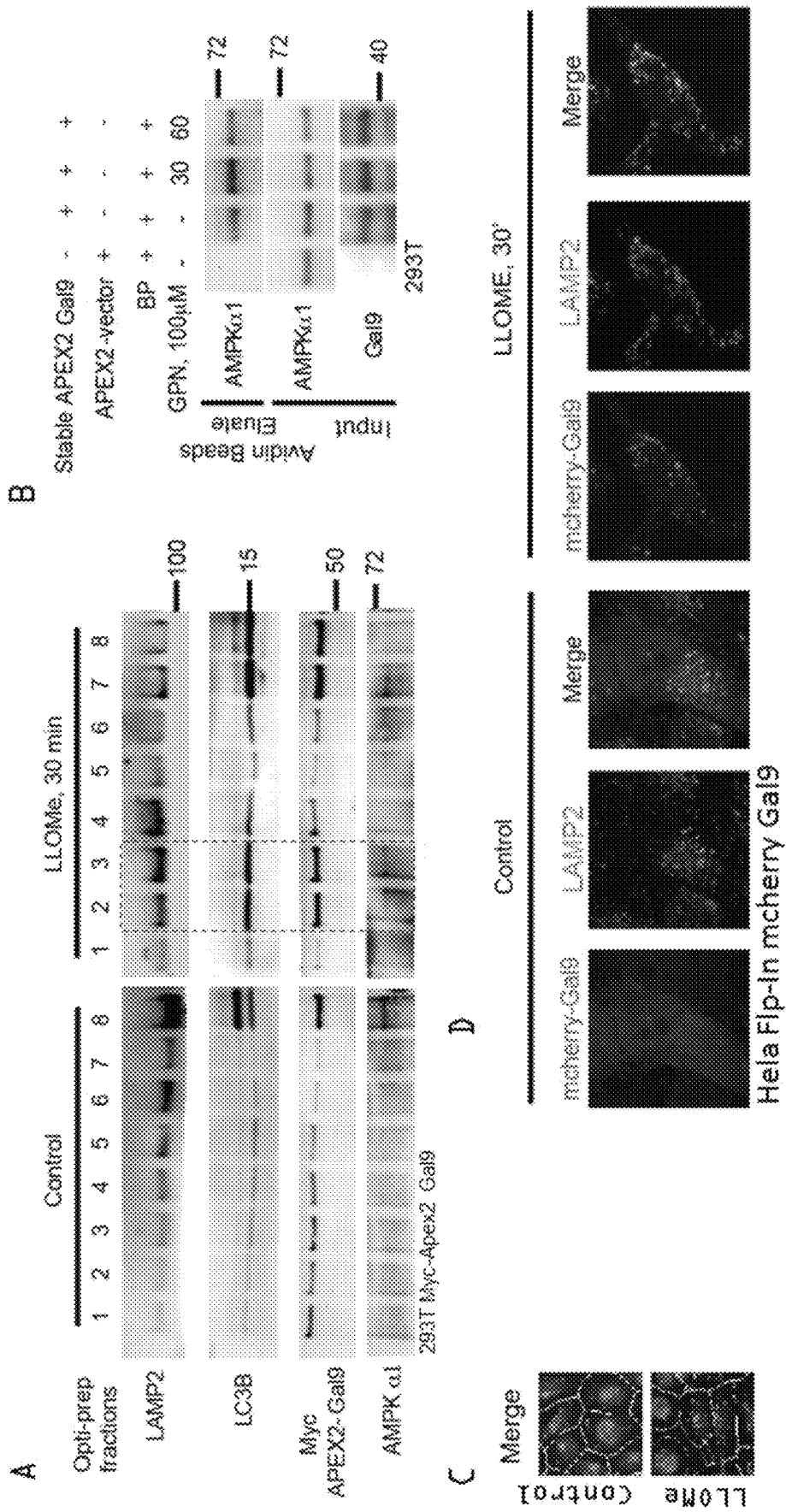
FIG. 9 shows that Gal9 and AMPK localize at damaged lysosomes. (A) Immunoblot analysis for Control and LLOMe treated samples fractionated on 5-22.5% Optiprep density gradients. (B) APEX2 proximity biotinylation analysis for Gal9 and AMPKα1. (C) High content quantification and (D) Confocal analysis of Gal9 and LAMP2 colocalization for Control and LLOMe treated samples.
Figure 10:
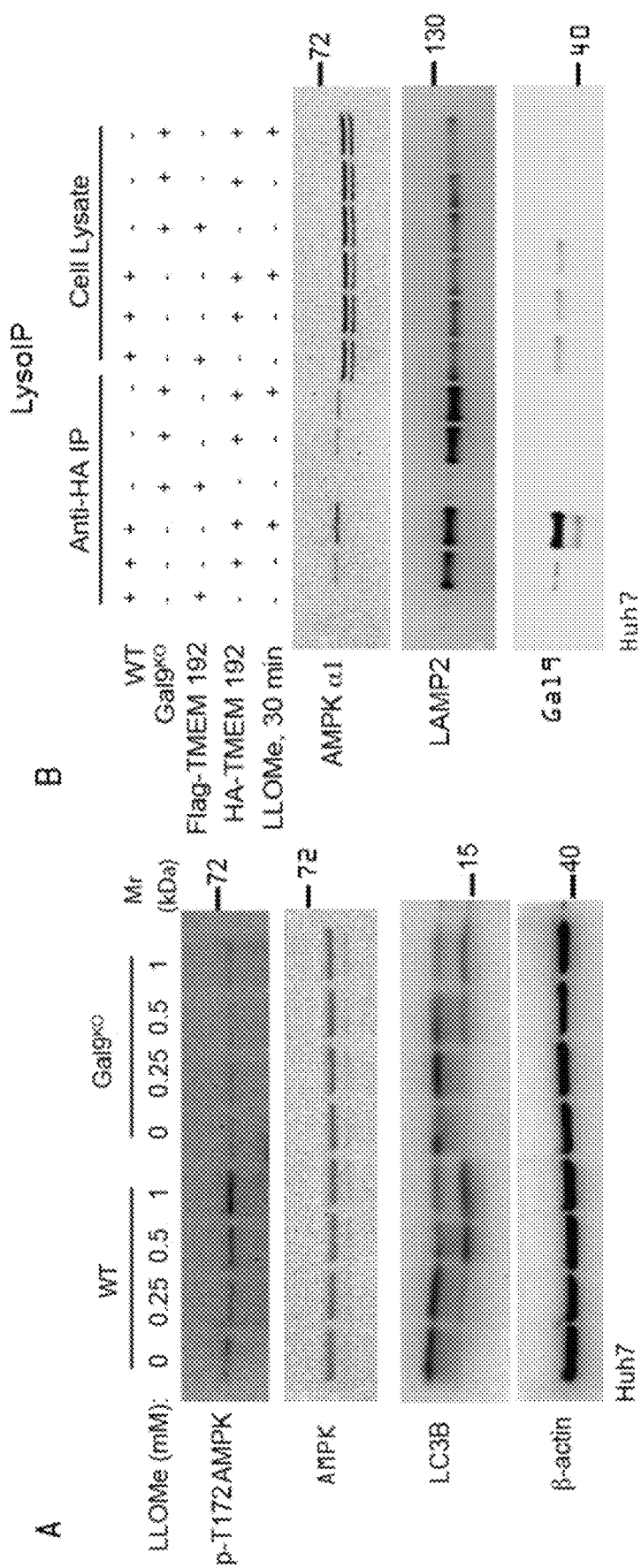
FIG. 10 shows that the loss of Gal9 prevents AMPK activation and translocation to damaged lysosomes. (A) Dose response AMPK activity (p-T172 AMPK) to lysosomal damage by LLOMe in WT and Gal9 KO Huh7 cells. (B) Lysosomal enrichment of AMPKα1 and Gal9 following lysosomal damage by LLOMe as shown by LysoIP in WT and Gal9 KO Huh7 cells.
Figure 11:
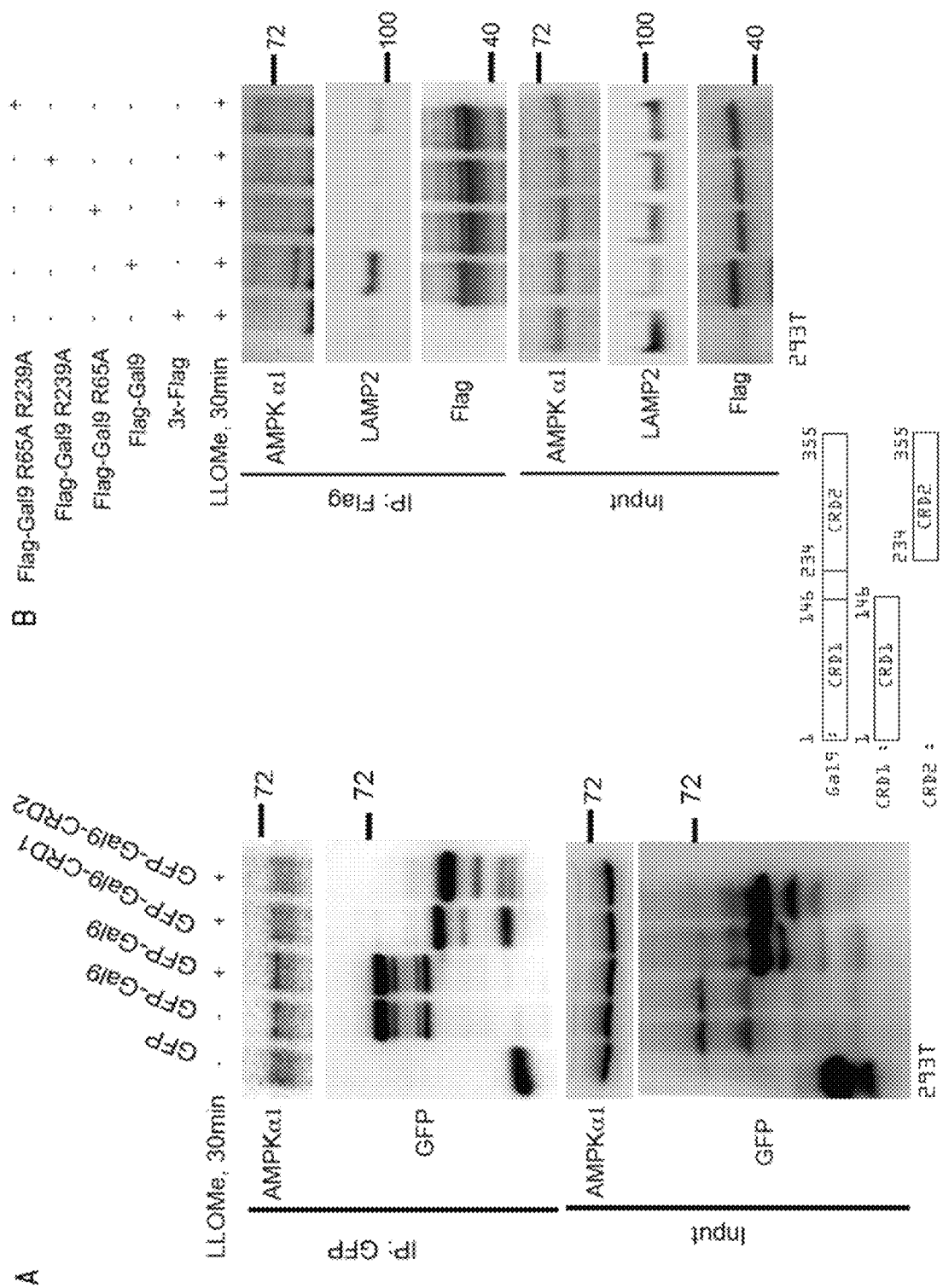
FIG. 11 shows that Gal9 binding to AMPK is glycosylation dependent. (A) Co-immunoprecipitation analysis between Gal9 or CRD deletion mutants and endogenous AMPKα1. (B) Co-IP analysis between Gal9 or glycosylation mutants and endogenous AMPKα1 or LAMP2
Figure 12:
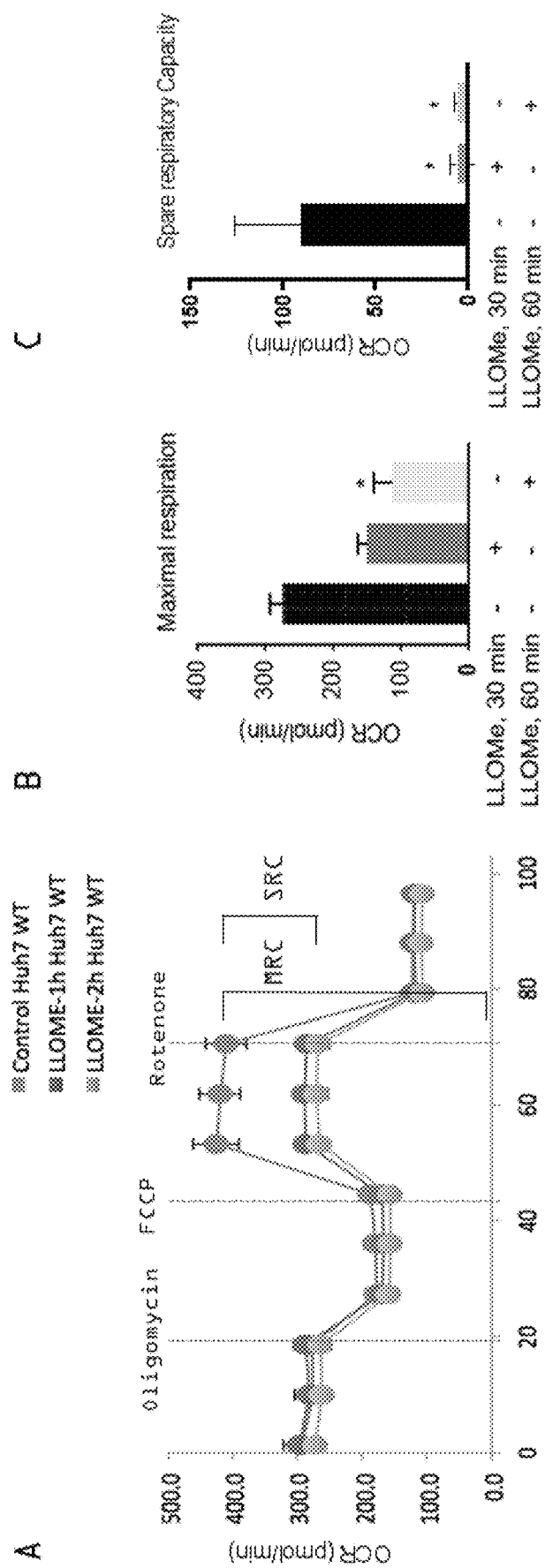
FIG. 12 shows that Lysosomal damage induces metabolic reprogramming. (A) Mito Stress test on Seahorse XF-24 instruments for analysis of Oxygen Consumption Rate (OCR) in Control and LLOMe treated Huh7 cells. (B) Maximal respiratory capacity (MRC) and (C) Spare respiratory capacity (SRC) was quantified by normalization of OCR levels to total protein OD values.

Previous studies have shown that lysosomal damage inhibits mTOR (Jia et al., 2018), a negative regulator of autophagy (Ganley et al., 2009; Hosokawa et al., 2009; Jung et al., 2009; Saxton and Sabatini, 2017), and induces autophagy as a process involved in clearance of damaged lysosomes (Fujita et al., 2013; Jia et al., 2018; Maejima et al., 2013). LLOMe has been shown to induce autophagy (Aits et al., 2015; Chauhan et al., 2016; Jia et al., 2018; Maejima et al., 2013; Thurston et al., 2012). We observed a similar LC3 response to metformin (FIG. 7A), in a dose response dependent manner (FIG. 7B). The studies presented here with AMPK, which is a positive regulator of autophagy (Egan et al., 2011; Kim et al., 2011), prompted us to test whether Gal9 and the machinery delineated above are involved in control of autophagic and LC3 responses to lysosomal damage. We observed by Optiprep membrane fractionations that upon LLOMe treatment LAMP2 moved to lighter fractions along with LC3B-II (FIG. 7C), likely reflecting membranous intermediates in the process of autophagic clearance of damaged lysosomes. These fractions were also positive for Gal9 and AMPKα1 (FIG. 7C), consistent with our other experiments such as LysoIP data (FIGS. 1SF and 6D). Gal9 KO cells (Gal9KO$^{Huh7}$) showed a lower autophagy response as seen by reduced level of LC3B-II relative to WT Huh7 cells treated with LLOMe (FIG. 7D). Gal9KO$^{Huh7}$ also showed reduced puncta for autophagy markers ATG13. ATG16L1 and LC3B (FIGS. 5SG-J, HCM for all markers and FIG. S5J, confocal for LC3B, illustrating LC3B puncta morphology). This defect could be complemented by Gal9 WT, but not by Gal9 mutant Gal9$^{R65A/239A}$ that can no longer recognize glycans exposed by lysosomal damage (FIGS. 7E and 6SA-B). Reduced levels of LC3B-II in response to LLOMe were seen with siRNA manipulations of the pathway controlled by Gal9 analyzed in previous sections. A knockdown of USP9X in Gal9KO$^{Huh7}$ partially restored LC3B-II levels in response to LLOMe (FIG. 7F). The effect of USP9X knockdown on restoring LC3 response to LLOMe in Gal9 KO cells was confirmed by HCM quantification of LC3 puncta (FIG. 7G). However, USP9X knockdown did not affect LC3 response in WT Huh7 cells, indicating that the effects of USP9X are manifested only in Gal9's absence (FIG. 7G). Similar effects of USP9X knockdowns were obtained with ATG13 and ATG16 markers (FIGS. 6SC and 6SD). Moreover, treatment of Huh7 and HeLa cells with the TAK1 inhibitor 5ZO reduced the LC3 response (FIG. 5C). Thus, the Gal9 effectors and the lysosomal-damage response pathway controlled by Gal9, as delineated above, control autophagy during lysosomal damage (FIG. 6SF).

Previous studies of lysosomal/endomembrane damage and galectin-controlled autophagic responses have established effects on microbial survival, with an emphasis on the roles of autophagic receptors (Thurston et al., 2012) receptor-regulators (Chauhan et al., 2016), E3 ligases (Chauhan et al., 2016; Cheng et al., 2017; Maejima et al., 2013), and mTOR (Jia et al., 2018) as effectors of galectin recognition of intracellular membrane damage. Earlier work has shown that immunological, pharmacological or physiological (starvation) induction of autophagy can control *Mycobacterium tuberculosis* (Mtb), an intracellular pathogen causing endomembrane damage (Manzanillo et al., 2012), in macrophages (Gutierrez et al., 2004). Since we here established AMPK as a downstream effector of Gal9, and AMPK plays a role in activating autophagy (Egan et al., 2011; Kim et al., 2011), we wanted to determine its role in autophagic control of intracellular microbes. A positive role of Gal9 in defense against Mth, has already been established (Jayaraman et al., 2010; Zhu et al., 2005). We thus tested here the effects of Gal9's effector AMPK on intracellular survival of Mtb in macrophages. We used our previously established system for assaying the role of autophagy in intracellular control of Mtb (Chauhan et al., 2016; Chauhan et al., 2015) and found that primary bone marrow-derived macrophages (BMM) from mice with Cre recombinase-induced AMPK loss via a CX3CR1-driven Cre-Lox system and AMPKα1$^{fl/fl}$/AMPKα2$^{fl/fl}$, displayed a reduced ability to control intracellular Mtb upon induction of autophagy, as compared to CX3CR1 Cre$^-$ AMPK-sufficient BMMs, showing that AMPK is important for the autophagic control of Mth in infected macrophages (FIG. S6E).

DISCUSSION

The present inventors have identified a link between lysosomal membrane damage and AMPK activation and defined the molecular mechanism of how cells recognize lysosomal injury and transduce this signal to AMPK. Additionally, we have assigned a defined physiological role—namely the response to lysosomal damage—to TAK1 as an AMPK-activating kinase that has hitherto been partially orphaned for a unifying biological role in the context of AMPK activation (Neumann, 2018). Furthermore, the findings reported here and in another study (Jia et al., 2018) assign a broad regulatory role to intracellular galectins. They also define a new type of signal transduction mechanism whereby recognition of membrane damage by galectins signals to the cellular systems that control mTOR and AMPK, the master regulators of cellular metabolism and the QC processes. Lysosomal damage has consequences on metabolism as reflected in the metabolomics changes observed here, and likely involve a multitude of complex events, with the mechanisms described here likely representing one subset. The specific mechanism of AMPK activation in response to lysosomal membrane damage depends on a herein delineated process of galectin-directed ubiquitination. These findings have broader implications for QC of cellular organelles, metabolic switching, cell physiology, and effector functions including autophagy and defense against intracellular pathogens.

The cascade of events activating AMPK in response to lysosomal membrane damage is triggered by exposure of exofacial (lumenal) glycans normally not in contact with the cytosol since the delimiting membrane is not breached. Once the membrane is damaged these exposed "exoglycoepitopes" are accessed by cytosolic galectins to set off a cascade of events, with those initiated by Gal9 culminating in activation of AMPK. This process depends on K63 ubiquitination of TAK1 (Herrero-Martin et al., 2009b; Singhirunnusom et al., 2005; Xie et al., 2006). A previously well characterized agonist of AMPK activation by TAK1 is TRAIL (Herrero-Martin et al., 2009b). Incidentally, TRAIL is known to induce lysosomal permeabilization and release of cathepsin B to the cytosol (Wemeburg et al., 2007). TAK1 furthermore responds to lysosomal rupture in the context of inflammasome activation (Okada et al., 2014). Thus, we propose that a primary physiological context of TAK1 in AMPK activation is lysosomal integrity.

Gal9 promotes AMPK activation by transducing lysosomal damage signals in a glycosylation-dependent manner to displace a specialized deubiquitinating enzyme USP9X (Al-Hakim et al., 2008, Dupont et al., 2009b; Paudel et al., 2019; Schwickart et al., 2010) from TAK1, permitting TAK1 activation. This authorizes K63 ubiquitination of TAK1 as a prelude to AMPK activation. AMPK has been detected on membranes with late endosomal/lysosomal properties (Zhang et al., 2014), thus emphasizing convergence of AMPK signaling upon lysosomal organelles. Our LysoIP data confirm that AMPK is present in small amounts on lysosomes and show that it is vastly increased immediately upon lysosomal damage. The recruitment of activated AMPK to damaged lysosomes occurs in a Gal9-dependent manner. We also find formation of a membranous compartment identified by flotation in Optiprep gradients, which is positive for LC3 as well as for AMPK, Gal9, and LAMP2, consistent with the autophagic response to lysosome injury (Maejima et al., 2013).

The canonical pathway for AMPK activation occurs via binding of AMP to its regulatory subunit γ when cellular AMP/ATP and ADP/ATP ratios increase during metabolic stress (Hardie, 2014). However, recent findings suggest that AMPK can detect glucose depletion before changes in cellular energy status using a non-canonical pathway localized to lysosomes that does not rely on AMP (Li et al., 2019; Lin and Hardie, 2018; Zhang et al., 2017; Zhang et al., 2014; Zhang et al., 2013). There are similarities but also major differences between the glucose-deprivation sensing pathway on lysosomes (Lin and Hardie, 2018) and the lysosome damage signaling pathway described in our study. They are likely two distinct non-canonical pathways occurring on lysosomes. The activation of AMPK by glucose deprivation on lysosomes happens due to shortage of its metabolite FBP normally bound as a substrate and a signaling molecule to aldolase (Zhang et al., 2017). FBP-aldolase orchestrates functional interactions between several components at the ER-lysosome contact sites, including inhibition of TRP channel-dependent local $Ca^{2+}$ fluxes in the absence of glucose (Li et al., 2019). In this case, chelation of cytosolic $Ca^{2+}$ by BAPTA-AM actually induced AMPK activation, ruling out a role for CAMMK2, consistent with our findings reported here and elsewhere (Jia et al., 2018) that CAMKK2 does not play a role in AMPK activation during lysosomal damage. However, the FBP-sensing pathway, which involves vATPase inhibition, depends on LKB1 (Zhang et al., 2014), whereas the dominant kinase during lysosomal damage response of AMPK is TAK1. The lysosomal localized FBP-sensing pathway borrows parts of the mTOR regulatory machinery stationed on the lysosomes (Saxton and Sabatini, 2017) and is composed of the v-ATPase-Ragulator/LAMTOR1-AXIN-LKB1-AMPK complex (Lin and Hardie, 2018; Zhang et al., 2014). In contrast, the TAK1-AMPK activation pathway responding to lysosomal damage is anchored to the lysosomes by Gal9 after its recognition of membrane tears leading to recruitment of activated AMPK to the lysosome. Nevertheless, there may be lateral overlaps between the FPB-sensing and the lysosomal damage-sensing pathways. This is evidenced by detection in our LC-MS/MS experiments with LLOMe (FIG. 1G) of increased Gal9-LAMTOR1 and Gal9-vATPase subunit ATP6V1A associations, as well as additional interactions with other components. e.g. NPC1 (Castellano et al., 2017), of the lysosomal mTOR regulatory apparatus (Saxton and Sabatini, 2017). One scenario is that the partial overlaps (e.g. LAMTOR1) between the Gal9 pathway and the FBP-sensing pathway are due to some structural requirements of AMPK recruitment to the lysosome. However, these overlaps may also be functional since LKB1 contributes low-grade tonic activation of AMPK at the lysosomal locale vastly amplified by TAK1 during lysosomal damage (Jia et al., 2018).

AMPK activation is sensitive to duration and extent of lysosomal damage and diminishes past 30 min of massive damage leading to autophagy/lysophagy. We have considered the possibility that a milder lysosomal damage may be a physiologically-relevant trigger for sustained activation AMPK and detected hallmarks of lysosomal damage during metformin treatment. Metformin, a widely used antidiabetic drug (He and Wondisford, 2015), is a known AMPK inducer believed to act by inhibiting complex I of the mitochondrial electron transport chain thus raising AMP levels (Foretz et al., 2014). Nevertheless, metformin's precise mode of action remains unclear, since activation of AMPK is not always supported by detection of AMP in metformin-treated cells (He and Wondisford, 2015). Furthermore, a plethora of effects is often invoked to explain metformin's mode of action and benefits (Hur and Lee, 2015; Rajani et al., 2017). Recent studies (Kim et al., 2016; Zhang et al., 2016) have implicated endolysosomal compartments in metformin action and it has been shown that metformin can induce AMPK through a lysosomal v-ATPase proposed to act as a sensor or an effector of metformin in AMPK activation (Zhang et al., 2016). In this model, metformin is proposed to engage the lysosomal FBP-sensing complex discussed above. Our metformin findings corroborate with the notion that lysosomal perturbations contribute to metformin's effects. However, as discussed above, the FBP-sensing and Gal9 damage-sensing pathways are distinct, as one operates in glucose metabolite sensing whereas the other detects lysosomal membrane damage. Metformin here induced hallmarks of lysosomal membrane damage including galectin and ubiquitin responses, and a reduction in LysoTracker and MagicRed staining. These were concentrations above metformin's physiological/pharmacological levels (Foretz et al., 2014; He and Wondisford, 2015). However, it is possible that a low-grade lysosomal damage occurs at lower metformin concentrations. Milder or early damage elicits ESCRT-dependent repair (Radulovic et al., 2018; Skowyra et al., 2018). Indeed, we observed that metformin elicited ALIX puncta formation, with ALIX being a component of the ESCRT machinery engaged in membrane repair caused by very mild lysosomal damage (Radulovic et al., 2018; Skowyra et al., 2018). Thus, these responses may represent a physiologically relevant aspect for sustained AMPK activation by metformin This work shows that TAK1 is a key mediator of AMPK activation in lysosomal damage. TAK1 is known for its activation in association with TGF-α1 (Akira, 2003), TNF-β (Sakurai et al., 2003), IL-1β (Ninomiya-Tsuji et al., 1999), LPS (Irie et al., 2000) and inflammasomes (Okada et al., 2014). TAK1 activity is regulated by ubiquitination (Singhirunnusom et al., 2005). There is a number of previously reported E3 ligases that K63-activate TAK1: TRAF6 (Fan et al., 2010; Sorrentino et al., 2008), TRAF2 (Jackson-Bemitsas et al., 2007), XIAP (Lu et al., 2007), Pellino (Strickson et al., 2017), Parkin (Wang et al., 2018), RNF8(Ho et al., 2015), TRIM5 (Pertel et al., 2011) and TRIM8 (Li et al., 2011). None of these were detected in our APEX2-Gal9 screen (Table S1, Tab 5). Another notable absence among Gal9 interactors is SCF$^{FBXO27}$ E3 ligase (Yoshida et al., 2017). SCF$^{FBXO27}$ recognizes lysosomal damage by binding to LAMP2, TMEM192, and VAMP7 (Yoshida et al., 2017), thus partially overlapping with the Gal9 repertoire. The absence of SCF$^{FBXO27}$ in our LC-MS/MS studies does not exclude its action in conjunction with Gal9 or Gal8 (Jia et al., 2018). Gal3 interacts with TRIM16 (Chauhan et al., 2016) and one other TRIM E3 ligase. TRIM25, was detected by LC-MS/MS with Gal9 albeit no dynamic changes were observed.

The complexity of the landscape of known E3 ligases as well as their paucity in our proteomic analyses (Table S1, Tab 5) prevented us from investigating TAK1 ubiquitination from the perspective of E3 ligases. Instead, we noticed dynamic changes in DUBs and VCP/p97 and identified USP9X as a key Gal9-governed DUB regulating the TAK1 ubiquitination state. USP9X acts as a linchpin in the switch caused by Gal9 and lysosomal damage. Other DUBs have been implicated in acting on TAK1, including CYLD (Ji et al., 2018; Reiley et al., 2007), USP4 (Fan et al., 2011), USP14 (Min et al., 2017), USP18 (Yang et al., 2015) and USP19 (Lei et al., 2019). Of these, our proteomic analyses with APEX2-Gal9 identified only USP19 but with low peptide counts below the threshold (Table S1, Tab 6).

Our study uncovers a novel control of ubiquitination responses by galectins. This underlies the TAK1-dependent activation of AMPK during lysosomal damage, a condition that we propose is a major physiological context for TAK1's activation of AMPK. The Gal9-AMPK axis is important in medically relevant contexts. e.g. in Mtb control, as shown here for AMPK and elsewhere for Gal9 (Jayaraman et al., 2010; Zhu et al., 2005). Therapeutic utility of these relationships with implications for metabolic disorders, cancer, and other diseases is underscored by metformin's action suggestive of a need to develop drugs targeting in a measured way lysosomal integrity and signaling.

Experimental Procedures
Antibodies and Reagents

Antibodies from Cell Signaling Technology were used at 1:1000 for WB including p-AMPK (#2535), AMPKα (#2532), p-ACC (#11818), ACC (#3662), p-ULK1 Ser555 (#5869), ULK1 (#6439), p-TAK1 (#4508), TAK1 (#5206), HA (#3724S), ATG13 (#13468) (1:200 for IF). LAMP1 (#9091) (1:500 for IF). Antibodies from Abcam were Galectin9 (ab69630; 1:500 WB), USP9x (ab19879; 1:1000 WB), GFP (ab290) (1:1000 for WB), GFP (ab38689) (2 μg/mL for immunoprecipitation (IP)), mCherry (ab183628) (1:1000 for WB; 1:200 for IF; 2 μg/mL for IP), VDAC1 (ab15895), GM130 (ab1299), PDI (ab2792), LKB1 (ab61122), CaMKK2 (ab96531), Cathepsin D (ab6313) (1:1000 for WB). Antibodies from MBL International were LC3 (PM036) (1:500 for IF) and ATG16L1(PM040) (1:400 for IF). Antibodies from BioLegend were Galectin-3 (#125402) (1:1000 for WB; 1:500 for IF). Other antibodies used in this study were from the following sources: Ubiquitin (FK-2) (Millipore 04-263; 1:1000 WB), Catalase (Calbiochem 219010; 1:1000 for WB), Galectin 9 (R&D AF2045; 1:200 WB), FLAG M2 (F1804) (1:1000 for WB) from Sigma Aldrich: Galectin 8 (sc-28254) (1:200 for WB) and beta-Actin (C4) (1:1000 for WB), c-Myc (sc-40), HRP-labeled anti-rabbit (1:2000 for WB) and anti-mouse (1:2000 for WB) secondary antibodies from Santa Cruz Biotechnology; LAMP2 (H4B4) (1:500 for IF) from DSHB of University of Iowa; Clean-Blot IP Detection Kit (HRP) (21232) (1:1000 for WB), Alexa Fluor 488, 568 (1:500 for IF). Dynabeads Protein G (Thermo Fisher Scientific; 10003D 50 μl/IP. DMEM, RPMI and EBSS media from Life Technologies. TAK1 inhibitor (5Z-oxozeanol) (09890) Sigma.

Cells and Cell Lines

HEK293T cells stably expressing APEX2-GAL9 were obtained by lentiviral transduction followed by selection with antibiotics. Briefly, for virus generation, 1 μg of pMD2.G and 2.7 μg of pPAX2 retroviral packaging plasmid were transfected into 293T cells together with 3.3 μg of pHAGE-Myc-APEX2-GAL9. Target HEK293T cells were transduced with virus containing medium, which was exchanged to growth medium after 24 h. Transduced cells were selected and cultured in Dulbecco's modified Eagle's medium (DMEM), supplemented by 10% fetal bovine serum and 2 μg/ml Puromycin (Sigma). Target-gene expression was confirmed via SDS-PAGE and immunoblot. HEK293T, HeLa and Huh7 cells were obtained from ATCC. Bone marrow derived macrophages (BMMs) were isolated from femurs of AMPKα1$^{fl/fl}$ LysM-Cre mice and its Crenegative litermates cultured in DMEM supplemented with mouse macrophage colony stimulating factor (mM-CSF, #5228, CST). HeLa Flp-In-Gal9$^{TetON}$ were generated using vectors and recipient cells from Terje Johansen. Cell lines for LysoIP were generated using constructs obtained from David M. Sabatini (Whitehead Institute).

Cultured Human Peripheral Blood Monocyte Cells

A trained phlebotomist in our HRRC-approved study drew 40-50 mL blood from healthy, consenting adult volunteers enrolled in the study. The different donors were kept separate and the blood in 10 mL vacutainers was pooled into 2-50 mL conicals. The volume was brought to 50 mL with sterile 1×PBS and mixed by inversion. 25 mL of the blood mix were carefully layered onto 20 mL of Ficoll (Sigma, #1077) in separate conical tubes and centrifuged at 2000 rpm for 30 min at 22° C. The buffer layer containing human peripheral blood monocytes (PBMCs) was removed, pooled, washed with 1×PBS twice and resuspended in ~20 mL RPMI media with 10% human AB serum and Primocin.

Plasmids, siRNAs, and Transfection

For proximity proteomics, human GAL9 was cloned into pHAGE-Myc-APEX2 using Gateway cloning (ThermoFisher Scientifc). Gal9 mutants were generated utilizing the QuikChange site-directed mutagenesis kit (Agilent) and confirmed by sequencing (Genewiz). siRNAs were from GE Dharmacon. Plasmid transfections were performed using the ProFection Mammalian Transfection System (Promega) or Amaxa nucleofection (Lonza). siRNAs were delivered into cells using either Lipofectamine RNAiMAX (ThermoFisher Scientific) or Amaxa nucleofection (Lonza).

Generation of Galectin9 CRISPR Mutant Cells

For generating Gal9 CRISPR mutant cells, the lentiviral vector lentiCRISPRv2 carrying both Cas9 enzyme and a gRNA targeting Gal9 (gRNA target sequence: ACACACACACCTGGTTCCAC SEQ ID NO: 2) was transfected into HEK293T cells together with the packaging plasmids psPAX2 and pCMV-VSV-G at the ratio of 5:3:2. Two days after transfection, the supernatant containing lentiviruses was collected and used to infect Huh7 cells. 36 h after infection, the cells were selected with puromycin (1 μg/mL) for one week in order to select Gal9 knockout cells. Gal9 knockout was confirmed by western blot. Selection of single clones was performed by dilution in 96-well, which were confirmed by western blots (FIG. S1C).

Generating HeLa Flp-In-Gal9$^{TetON}$ Cell Line

Hela Flp-In host cells were transfected with Gal9 reconstructed plasmid and the pOG44 expression plasmid at ratio of 9:1. 24 h after transfection, the cells were washed, and fresh medium was added to the cells. 48 h after transfection, the cells were split into fresh medium at around 25% confluency. The cells are incubated at 37° C. for 2-3 h until they have attached to the culture dish. Then medium was removed and fresh medium containing 100 µg/mL hygromycin was added. The cells were fed with selective medium every 3-4 days until single cell clone can be identified. Hygromycin-resistant clones were picked and expanded each to test. The tested clones were incubated in the medium containing 1 µg/mL tetracycline overnight and were tested by western blot for the expression of Gal9.

LysoIP Assay

Stable LysoIP cells were produced, by utilizing lentiviruses constructs from David M. Sabatini Lab (White Head Institute). HEK293T cells were transfected with pLJC5-TMEM192-3xHA or pLJC5-TMEM192-2XFLAG constructs in combination with pCMV-VSV-G and psPAX2 packaging plasmids, 60 h after transfection, the supernatant containing lentiviruses was collected and centrifuged to remove cells and then frozen at −80° C. To establish LysoIP stably expressing cell lines, HEK293T, Huh7 or Huh7 Gal9$^{KO}$ cells were plated in 10 cm$^2$ dish in DMEM with 10% FBS and infected with 500 µL of virus-containing media overnight followed by addition of 1 µg/mL puromycin for selection. Cells were plated in 15 cm$^2$ culture plates and were used at 90% confluency for each LysoIP. Cells with or without 1 mM LLOMe treatment were quickly rinsed twice with PBS and then scraped in 1 mL of KPBS (136 mM KCl, 10 mM KH$_2$PO$_4$, pH7.25 was adjusted with KOH) and centrifuged at 3000 rpm for 2 min at 4° C. Pelleted cells were resuspended in 950 µL KPBS and reserved 25 µL for further processing of the whole-cell lysate. The remaining cells were gently homogenized with 20 strokes of a 2 mL homogenizer. The homogenate was then centrifuged at 3000 rpm for 2 min at 4° C. and the supernatant was incubated with 100 µL of KPBS prewashed anti-HA magnetic beads (ThermoFisher) on a gentle rotator shaker for 3 min. Immunoprecipitants were then gently washed three times with KPBS and eluted with 2×Laemmli sample buffer (Bio-Rad) and subjected to immunoblot analysis.

Murine Tuberculosis Infection Assay

*Mycobacterium tuberculosis* Erdman (Erdman) culture was prepared by thawing frozen stock aliquot and grown in 7H9 Middlebrook liquid medium supplemented with oleic acid, albumin, dextrose and catalase (OADC. Becton Dickinson, Inc., Sparks, MD, USA), 0.5% glycerol and 0.05% Tween 80. Cultures were grown at 37° C. BMMs were infected with Erdman at MOI 10 and incubated with full medium for 18 h or 16 h with following 2 h EBSS, lysed, and plated on 7H11 agar plates. CFU was enumerated 3~4 weeks later.

High Content Microscopy

The cells were plated in 96 well plates on day 1 and were treated on day 2, followed by fixation in 4% paraformaldehyde for 5 min. After fixation, cells were washed twice with 1×PBS and were then permeabilized with 0.1% saponin in 3% Bovine serum albumin (BSA) for 30 min. The cells were then incubated with primary antibodies O/N at 4° C. On day3, the cells were washed twice with 1×PBS and incubated with secondary antibodies for 1 h followed by 5 min incubation with Hoechst 33342. High content microscopy with automated image acquisition and quantification was carried out using a Cellomics HCS scanner and iDEV software (ThermoFisher Scientific). Automated epifluorescence image collection was performed for a minimum of 500 cells per well. Epifluorescence images were machine analyzed using preset scanning parameters and object mask definitions. Hoechst 33342 staining was used for autofocus and to automatically define cellular outlines based on background staining of the cytoplasm. Primary objects were cells, and regions of interest (ROI) or targets were algorithm-defined by shape/segmentation, maximum/minimum average intensity, total area and total intensity, etc., to automatically identify puncta or other profiles within valid primary objects. All data collection, processing (object, ROI, and target mask assignments) and analyses were computer driven independently of human operators.

Immunofluorescence Confocal Microscopy

For immunofluorescence confocal microscopy, cells were plated onto coverslips in 12 well or 24 well plates. Cells were transfected with plasmids as indicated in figures. Cells were incubated in full media or EBSS for 2 h and fixed in 4% paraformaldehyde for 10 min followed by permeabilization with 0.1% saponin in 3% BSA. Cells were then blocked in 3% BSA and then stained with primary antibodies followed by washings with PBS and then incubation with appropriate secondary antibodies for 1 h at room temperature. Coverslips were mounted using ProLong Gold Antifade Mountant (Invitrogen) and analyzed by confocal microscopy using the Zeiss LSM510 Laser Scanning Microscope.

Membrane Fractionation

Membrane fractionation was performed as described previously (Ge et al., 2013). HEK293T cells (10 dishes per sample) were plated in 15-cm$^2$ dishes and treated with 1 mM LLOMe for 30 mins. For sequential centrifugation cells were harvested, and the pellet was resuspended in 2.7×cell pellet volume of B1 buffer (20 mM Hepes-KOH, pH 7.2, 400 mM sucrose, and 1 mM EDTA) containing protease and phosphatase inhibitors (Roche) and 0.3 mM DTT and then was homogenized by passing through a 22-G needle until 85-90% lysis was achieved (analyzed by trypan blue staining). Homogenates were subjected to sequential differential centrifugation at 3,000 g for 10 min, 25.000 g for 20 min, and 100,000 g for 30 min to collect the pelleted membranes (3K, 25K, and 100K, respectively) using a TLA100.3 rotor (Beckman Coulter) and a polypropylene tube. The pellets were suspended in B88 buffer (20 mM Hepes, pH 7.2, 150 mM potassium acetate, 5 mM magnesium acetate, and 250 mM sorbitol). 5×SDS loading buffer was added, and samples were boiled for 5 min and analyzed by immunoblotting. Further fractionation using membrane floatation in a sucrose step gradient followed by centrifugation in OptiPrep step gradients was performed as described previously (Ge et al., 2013). For this, 25K membrane pellets were suspended in 1 ml of 19% OptiPrep for a step gradient containing 0.5 ml of 22.5%, 1 ml of 19% (sample), 0.9 of ml 16%, 0.9 ml of 12%, 1 ml of 8%, 0.5 ml of 5%, and 0.2 ml of 0% OptiPrep each. The OptiPrep gradient was centrifuged at 150,000 g for 3 h, and subsequently, eight fractions of 0.5 ml each were collected from the top. Fractions were diluted with B88 buffer, and membranes were collected by centrifugation at 100,000 g for 1 h. Samples were subjected to SDS-PAGE, and Western blotting for LAMP2, AMPK☐, myc-Gal9 and LC3B was done as described in the following section.

Immunoblotting and Co-Immunoprecipitation Assay

Western blotting and co-immunoprecipitation (co-IP) were performed as described previously (Chauhan et al., 2016). For TAK1 inhibition, the cells were treated with TAK1 inhibitor (5Z-oxozeanol) 1 h prior to LLOMe treatment. For co-IP, cells were transfected with plasmids as indicated in figures and lysed in NP-40 buffer containing protease inhibitor cocktail and PMSF. Lysates were incubated with antibodies at 4° C. for 4 h followed by incubation with protein G Dynabeads for 2 h at 4° C. Beads were washed three times with PBS and boiled with SDS containing sample buffer, samples were processed for immunoblotting to analyze the interactions between immunoprecipitated proteins.

LysoTracker Assay

Prepare fresh LysoTracker Staining Solution (2 µL LysoTracker in 1 mL medium). Add 10 µL LysoTracker Staining Solution to no treatment, LLOMe treated or Metformin treated THP-1 cells in 96 wells for total 100 µL per well and incubate at 37° C. for 30 min protected from light. Rinse gently by 1×PBS and fix in 4% Paraformaldehyde for 2 min. Wash once by 1×PBS and blot with Hoechst 33342 for 2 min before detecting by high content microscopy.

Magic Red Assay

Reconstitute Magic Red by adding DMSO and dilute Magic Red 1:10 by adding $H_2O$. Add 4 µL Magic Red to no treatment, LLOMe treated or Metformin treated THP-1 cells in 96 wells for total 100 µL per well and incubate at 37° C. for 15 min and protected from light. Rinse gently by 1×PBS and fix in 4% Paraformaldehyde for 2 min. Wash once by 1×PBS and blot with Hoechst 33342 for 2 min before detecting by high content microscopy.

Proteomic Mass Spectrometry, Data Processing and Analysis (i) SILAC Labelling and Treatment for Proteomic Analyses HEK293T cells stably expressing APEX2-GAL9 were grown in lysine- and arginine-free DMEM supplemented with fetal bovine serum (FBS), L-Glutamine, Sodium pyruvate, heavy arginine (R10) (38 µg/m) and lysine (K8) (66 µg/ml) or light arginine (R0) (38 µg/ml) and lysin (K0) (66 µg/ml), respectively. Further experiments were conducted as soon as the cells reached a protein labelling with heavy amino acids of at least 95%. Heavy-labeled cells were either treated with 1 mM Leu-Leu methyl ester hydrobromide (LLOMe. Sigma) for one hour or with 100 µM Gly-Phe β-naphthylamide (GPN, Sigma) for one hour at 37° C. while light-labelled cells were treated with control (DMSO).

(ii) Proximity Labeling for Proteomic Mass Spectrometry

Proximity labeling was performed in SILAC labelled HEK293T cells stably expressing APEX2-GAL9 as described before (Le Guerroue et al., 2017). Briefly, cells were incubated with 500 µM Biotin-Phenol during the last 30 min of LLOMe or GPN treatment and subsequently pulsed by addition of $H_2O_2$ for 1 min at room temperature. To stop the biotinylation reaction, they were washed 3× with quencher solution (10 mM sodium azide, 10 mM sodium ascorbate, 5 mM Trolox in DPBS) and 3× with PBS. All further steps were performed at 4° C. unless indicated otherwise. After cell harvest with 0.25% Trypsin/EDTA (ThermoFisher Scientific), cells were counted and heavy- and light-labelled cells were mixed at a 1:1 ratio based on total cell numbers. After centrifugation, the resulting cell pellets were lysed in RIPA (50 mM Tris, 150 mM NaCl, 0.1% SDS, 1% Triton X-100, 0.5% sodium deoxycholate) supplemented with 10 mM sodium ascorbate, 1 mM sodium azide, 1 mM Trolox and protease inhibitors (Roche Complete). Samples were sonicated 2× for 1 s, spun down at 10.000 g for 10 min before application to streptavidin agarose resin (Thermo) and incubation with overhead shaking overnight.

(iii) Proteomic Mass Spectrometry

IP-MS was performed as described before (Lobingier et al., 2017). Briefly, samples were washed 3× in RIPA buffer and 3× in 3 M Urea buffer (in 50 mM ABC) followed by incubation with TCEP (5 mM final) for 30 min at 55° C. with orbital shaking. After alkylation with IAA (10 mM final) for 20 min at room temperature in the dark the reaction was quenched with DTT (20 mM final). Samples were washed 2× with 2M Urea (in 50 mM ABC) before trypsin digestion overnight at 37° C. (20 µg/ml final). The resin was spun down and supernatants containing digested peptides were collected. After washing the resin 2× with 2 M Urea and pooling all supernatants the samples were acidified with TFA (1% final). Digested peptides were desalted on custom-made C18 stage tips. Using an Easy-nLC1200 liquid chromatography, peptides were loaded onto 75 µm×15 cm fused silica capillaries (New Objective) packed with C18AQ resin (Reprosil-Pur 120, 1.9 µm, Dr. Maisch HPLC). Peptide mixtures were separated using a gradient of 5%-33% acetonitrile in 0.1% acetic acid over 35 min and detected on an Orbitrap Elite mass spectrometer (Thermo Scientific). Dynamic exclusion was enabled for 30 s and singly charged species or species for which a charge could not be assigned were rejected. MS data was processed and analyzed using MaxQuant (version 1.6.0.1) (Cox and Mann, 2008) and Perseus (version 1.5.8.4) (Tyanova et al., 2016). All proximity experiments were performed in triplicates. Unique and razor peptides were used for semiquantive analyses. Matches to common contaminants, reverse identifications and identifications based only on site-specific modifications were removed prior to further analysis. Log 2 Heavy/Light ratios were calculated. A threshold based on a log 2 fold change of greater than 1-fold or less than −1-fold was chosen so as to focus the data analysis on a smaller set of proteins with the largest alterations in abundance. Student t-tests were used to determine statistical significance between treatments. A p-value<0.05 was considered statistically significant.

Metabolomic Analyses by CE-QaQ/TOFMS CE-MS/MS

Cultured cells ($10^6$ cells/sample) were used for the extraction of intracellular metabolites. The culture medium was aspirated from the dish and cells were washed twice by 5% mannitol solution (10 mL first and then 2 mL). The cells were then treated with 800 µL of methanol and left at rest for 30 s in order to inactivate enzymes. Next, the cell extract was treated with 550 µL of Milli-Q water containing internal standards (H3304-1002, Human Metabolome Technologies, Inc., Tsuruoka, Japan) and left at rest for another 30 s. The extract was obtained and centrifuged at 2,300×g and 4° C. for 5 min and then 800 µL of upper aqueous layer was centrifugally filtered through a Millipore 5-kDa cutoff filter at 9,100×g and 4° C. for 120 min to remove proteins. The filtrate was centrifugally concentrated and re-suspended in 50 µL of Milli-Q water for CE-MS analysis. Cationic compounds were measured in the positive mode of CE-TOFMS and anionic compounds were measured in the positive and negative modes of CE-MS/MS according to the methods developed by Soga, et al (Soga and Heiger, 2000, Soga et al., 2003; Soga et al., 2002). Peaks detected by CE-TOFMS and CE-MS/MS were extracted using automatic integration software (MasterHands, Keio University, Tsuruoka, Japan (Sugimoto et al., 2010) and MassHunter Quantitative Analysis B.04.00, Agilent Technologies, Santa Clara. CA, USA, respectively) in order to obtain peak information including m/z, migration time (MT), and peak area. The peaks were annotated with putative metabolites from the HMT metabolite database based on their MTs in CE and m/z values determined by TOFMS. The tolerance range for the peak annotation was configured at ±0.5 min for MT and ±10 ppm for m/z. In addition, concentrations of metabolites were calculated by normalizing the peak area of each metabolite with respect to the area of the internal standard and by using standard curves, which were obtained by three-point calibrations. Hierarchical cluster analysis (HCA) and principal component analysis (PCA) were performed by PeakStat and SampleStat software, respectively. Detected metabolites were plotted on metabolic pathway maps using VANTED (Visualization and Analysis of Networks containing Experimental Data) software (Junker et al., 2006).

Table S1, shows the metabolomic and proteomic data referred to in the examples section. See, Jia, et al., (2020) *Mol. Cell.* 77, 951-969 e959 which is incorporated by reference in its entirety herein. Available at: sciencedirect.com/science/article/abs/pii/S109727651930958X Statistical Analyses Data are expressed as means±SEM (n≥3). Data were analyzed with a paired two-tailed Student's t-test or analysis of variance (ANOVA) was used. Statistical significance was defined as † $p>0.05$; *$p<0.05$. **$p<0.01$.

REFERENCES

Abu-Remaileh, M., Wyant, G. A., Kim, C., Laqtom, N. N., Abbasi, M., Chan, S. H., Freinkman. E., and Sabatini, D. M. (2017). Lysosomal metabolomics reveals V-ATPase- and mTOR-dependent regulation of amino acid efflux from lysosomes. Science 358, 807-813.

Aits, S., Kricker, J., Liu, B., Ellegaard, A. M., Hamalisto, S., Tvingsholm, S., Corcelle-Termeau. E., Hogh, S., Farkas, T., Holm Jonassen, A., et al. (2015). Sensitive detection of lysosomal membrane permeabilization by lysosomal galectin puncta assay. Autophagy 11, 1408-1424.

Akira, S. (2003). Toll-like receptor signaling. The Journal of biological chemistry 278, 38105-38108.

Al-Hakim, A. K., Zagorska, A., Chapman, L., Deak, M., Peggie, M., and Alessi, D. R. (2008). Control of AMPK-related kinases by USP9X and atypical Lys(29)/Lys(33)-linked polyubiquitin chains. The Biochemical journal 411, 249-260.

An, H., and Harper, J. W. (2018). Systematic analysis of ribophagy in human cells reveals bystander flux during selective autophagy. Nature cell biology 20, 135-143.

Arhzaouy, K., Papadopoulos, C., Schulze, N., Pittman, S. K., Meyer, H., and Weihl, C. C. (2019). VCP maintains lysosomal homeostasis and TFEB activity in differentiated skeletal muscle. Autophagy 15, 1082-1099.

Berg, T. O., Stromhaug, E., Lovdal, T., Seglen, O., and Berg, T. (1994). Use of glycyl-L-phenylalanine 2-naphthylamide, a lysosome-disrupting cathepsin C substrate, to distinguish between lysosomes and prelysosomal endocytic vacuoles. The Biochemical journal 300 (Pt 1), 229-236.

Bjorkoy, G., Lamark, T., Brech, A., Outzen, H., Perander, M., Overvatn, A., Stenmark, H., and Johansen, T. (2005). p62/SQSTM1 forms protein aggregates degraded by autophagy and has a protective effect on huntingtin-induced cell death. The Journal of cell biology 171, 603-614.

Castellano, B. M., Thelen, A. M., Moldavski, O., Feltes, M., van der Welle, R. E., Mydock-McGrane, L., Jiang, X., van Eijkeren, R. J., Davis, O. B., Louie, S. M., et al. (2017). Lysosomal cholesterol activates mTORC1 via an SLC38A9-Niemann-Pick $C_1$ signaling complex. Science 355, 1306-1311.

Chauhan, S., Kumar, S., Jain, A., Ponpuak, M., Mudd, M. H., Kimura, T., Choi, S. W., Peters, R., Mandell, M., Bruun, J. A., et al. (2016). TRIMs and Galectins Globally Cooperate and TRIM16 and Galectin-3 Co-direct Autophagy in Endomembrane Damage Homeostasis. Developmental cell 39, 13-27.

Chauhan, S., Mandell, M. A., and Deretic, V. (2015). IRGM Governs the Core Autophagy Machinery to Conduct Antimicrobial Defense. Molecular cell 58, 507-521.

Chen, Z., Shen, X., Shen, F., Zhong, W., Wu, H., Liu, S., and Lai, J. (2013). TAK1 activates AMPK-dependent cell death pathway in hydrogen peroxide-treated cardiomyocytes, inhibited by heat shock protein-70. Molecular and cellular biochemistry 377, 35-44.

Cheng, Y. L., Wu, Y. W., Kuo, C. F., Lu, S. L., Liu, F. T., Anderson, R., Lin, C. F., Liu, Y. L., Wang. W. Y., Chen, Y. D., et al. (2017). Galectin-3 Inhibits Galectin-8/Parkin-Mediated Ubiquitination of Group A *Streptococcus*. mBio 8.

Cox, J., and Mann, M. (2008). MaxQuant enables high peptide identification rates, individualized p.p.b.-range mass accuracies and proteome-wide protein quantification. Nature biotechnology 26, 1367-1372.

Criollo, A., Niso-Santano, M., Malik, S. A., Michaud. M., Morselli. E., Marino, G., Lachkar, S., Arkhipenko, A. V., Harper, F., Pierron, G., et al. (2011). Inhibition of autophagy by TAB2 and TAB3. The EMBO journal 30, 4908-4920.

Deretic, V., Saitoh, T., and Akira, S. (2013). Autophagy in infection, inflammation and immunity. Nat Rev Immunol 13, 722-737.

Dikic, I., and Elazar, Z. (2018). Mechanism and medical implications of mammalian autophagy. Nature reviews Molecular cell biology 19, 349-364.

Dupont, N., Chauhan, S., Arko-Mensah, J., Castillo, E. F., Masedunskas, A., Weigert, R., Robenek. H., Proikas-Cezanne, T., and Deretic. V. (2014). Neutral lipid stores and lipase PNPLA5 contribute to autophagosome biogenesis. Current biology: CB 24, 609-620.

Dupont, N., Lacas-Gervais, S., Bertout, J., Paz, I., Freche, B., Van Nhieu, G. T., van der Goot. F. G., Sansonetti, P. J., and Lafont. F. (2009a). *Shigella* phagocytic vacuolar membrane remnants participate in the cellular response to pathogen invasion and are regulated by autophagy. Cell Host Microbe 6, 137-149.

Dupont, S., Mamidi, A., Cordenonsi, M., Montagner, M., Zacchigna, L., Adomo, M., Martello, G., Stinchfield, M. J., Soligo, S., Morsut, L., et al. (2009b). FAM/USP9x, a deubiquitinating enzyme essential for TGFbeta signaling, controls Smad4 monoubiquitination. Cell 136, 123-135.

Egan, D. F., Shackelford, D. B., Mihaylova, M. M., Gelino, S., Kohnz. R. A., Mair. W., Vasquez, D. S., Joshi, A., Gwinn, D. M., Taylor, R., et al. (2011). Phosphorylation of ULK1 (hATG1) by AMP-activated protein kinase connects energy sensing to mitophagy. Science 331, 456-461.

Elgendy, M., Ciro, M., Abdel-Aziz, A. K., Belmonte, G., Dal Zuffo, R., Mercurio, C., Miracco, C., Lanfrancone, L., Foiani, M., and Minucci, S. (2014). Beclin I restrains tumorigenesis through Mcl-1 destabilization in an autophagy-independent reciprocal manner. Nature communications 5, 5637.

Fan, Y., Yu, Y., Shi, Y., Sun, W., Xie, M., Ge, N., Mao, R., Chang, A., Xu, G., Schneider, M. D., et al. (2010). Lysine 63-linked polyubiquitination of TAK1 at lysine 158 is required for tumor necrosis factor alpha- and interleukin- 1beta-induced IKK/NF-kappaB and JNK/AP-1 activation. The Journal of biological chemistry 285, 5347-5360.

Fan, Y. H., Yu, Y., Mao. R. F., Tan, X. J., Xu, G. F., Zhang, H., Lu, X. B., Fu, S. B., and Yang, J. (2011). USP4 targets TAK1 to downregulate TNFalpha-induced NF-kappaB activation. Cell death and differentiation 18, 1547-1560.

Foretz, M., Guigas. B., Bertrand, L., Pollak, M., and Viollet, B. (2014). Metformin: from mechanisms of action to therapies. Cell metabolism 20, 953-966.

Fujita, N., Morita, E., Itoh, T., Tanaka, A., Nakaoka. M., Osada, Y., Umemoto, T., Saitoh, T., Nakatogawa, H., Kobayashi, S., et al. (2013). Recruitment of the autophagic machinery to endosomes during infection is mediated by ubiquitin. The Journal of cell biology 203, 115-128.

Gaber, T., Strehl, C., and Buttgereit, F. (2017). Metabolic regulation of inflammation. Nat Rev Rheumatol 13, 267-279.

Gack, M. U., Shin, Y. C., Joo, C. H., Urano. T., Liang, C., Sun, L., Takeuchi, O., Akira, S., Chen, Z., Inoue, S., et al. (2007). TRIM25 RING-finger E3 ubiquitin ligase is essential for RIG-I-mediated antiviral activity. Nature 446, 916-920.

Ganley, I. G., Lam du. H., Wang, J., Ding, X., Chen, S., and Jiang, X. (2009). ULK1.ATG13.FIP200 complex mediates mTOR signaling and is essential for autophagy. The Journal of biological chemistry 284, 12297-12305.

Garcia. D., and Shaw, R. J. (2017). AMPK: Mechanisms of Cellular Energy Sensing and Restoration of Metabolic Balance. Molecular cell 66, 789-800.

Garin, J., Diez, R., Kieffer, S., Dermine, J. F., Duclos, S., Gagnon, E., Sadoul, R., Rondeau, C., and Desjardins, M. (2001). The phagosome proteome: insight into phagosome functions. The Journal of cell biology 152, 165-180.

Ge, L., Melville, D., Zhang, M., and Schekman, R. (2013). The ER-Golgi intermediate compartment is a key membrane source for the LC3 lipidation step of autophagosome biogenesis. eLife 2, e00947.

Gonzalez, A., Valeiras, M., Sidransky. E., and Tayebi, N. (2014). Lysosomal integral membrane protein-2: a new player in lysosome-related pathology. Molecular genetics and metabolism 111, 84-91.

Gutierrez, M. G., Master, S. S., Singh, S. B., Taylor, G. A., Colombo, M. I., and Deretic, V. (2004). Autophagy is a defense mechanism inhibiting BCG and *Mycobacterium tuberculosis* survival in infected macrophages. Cell 119, 753-766.

Hansen, M., Rubinsztein, D. C., and Walker, D. W. (2018). Autophagy as a promoter of longevity: insights from model organisms. Nature reviews Molecular cell biology 19, 579-593.

Hardie, D. G. (2011). AMP-activated protein kinase; an energy sensor that regulates all aspects of cell function. Genes Dev 23, 1895-1908.

Hardie, D. G. (2014). AMPK-sensing energy while talking to other signaling pathways. Cell metabolism 20, 939-952.

Hawley, S. A., Pan, D. A., Mustard, K. J., Ross, L., Bain, J., Edelman, A. M., Frenguelli, B. G., and Hardie, D. G. (2005). Calmodulin-dependent protein kinase kinase-beta is an alternative upstream kinase for AMP-activated protein kinase. Cell metabolism 2, 9-19.

He, L., and Wondisford, F. E. (2015). Metformin action: concentrations matter. Cell metabolism 21, 159-162.

Heneka, M. T., Kummer, M. P., Stutz, A., Delekate, A., Schwartz, S., Vieira-Saecker, A., Griep, A., Axt. D., Remus, A., Tzeng, T. C., et al. (2013). NLRP3 is activated in Alzheimer's disease and contributes to pathology in APP/PS1 mice. Nature 493, 674-678.

Herrero-Martin, G., Hover-Hansen, M., Garcia-Garcia. C., Fumarola, C., Farkas, T., Lopez-Rivas, A., and Jaattela. M. (2009a). TAK1 activates AMPK-dependent cytoprotective autophagy in TRAIL-treated epithelial cells. The EMBO journal 28, 677-685.

Herrero-Martin, G., Hoyer-Hansen, M., Garcia-Garcia, C., Fumarola, C., Farkas, T., Lopez-Rivas, A., and Jaattela, M. (2009b). TAK1 activates AMPK-dependent cytoprotective autophagy in TRAIL-treated epithelial cells. The EMBO journal 28, 677-685.

Herzig. S., and Shaw, R. J. (2018). AMPK: guardian of metabolism and mitochondrial homeostasis. Nature reviews Molecular cell biology 19, 121-135.

Ho, Y. K., Zhi, H., Bowlin, T., Dorjbal, B., Philip, S., Zahoor, M. A., Shih, H. M., Semmes. O. J., Schaefer, B., Glover, J. N., et al. (2015). HTLV-1 Tax Stimulates Ubiquitin E3 Ligase, Ring Finger Protein 8, to Assemble Lysine 63-Linked Polyubiquitin Chains for TAK1 and IKK Activation. PLoS pathogens 11, e1005102.

Hosokawa. N., Hara, T., Kaizuka, T., Kishi, C., Takamura, A., Miura, Y., Iemura, S., Natsume, T., Takehana, K., Yamada, N., et al. (2009). Nutrient-dependent mTORC1 association with the ULK1-Atg13-FIP200 complex required for autophagy. Mol Biol Cell 20, 1981-1991.

Hur, K. Y., and Lee, M. S. (2015). New mechanisms of metformin action: Focusing on mitochondria and the gut. J Diabetes Investig 6, 600-609.

Irie, T., Muta, T., and Takeshige, K. (2000). TAK1 mediates an activation signal from toll-like receptor(s) to nuclear factor-kappaB in lipopolysaccharide-stimulated macrophages. FEBS letters 467, 160-164.

Jackson-Bemitsas, D. G., Ichikawa, H., Takada, Y., Myers, J. N., Lin, X. L., Damay, B. G., Chaturvedi, M. M., and Aggarwal, B. B. (2007). Evidence that TNF-TNFR1-TRADD-TRAF2-RIP-TAK1-IKK pathway mediates constitutive NF-kappaB activation and proliferation in human head and neck squamous cell carcinoma. Oncogene 26, 1385-1397.

Jager, S., Handschin, C., St-Pierre, J., and Spiegelman, B. M. (2007). AMP-activated protein kinase (AMPK) action in skeletal muscle via direct phosphorylation of PGC-1alpha. Proceedings of the National Academy of Sciences of the United States of America 104, 12017-12022.

Jayaraman, P., Sada-Ovalle, I., Beladi, S., Anderson, A. C., Dardalhon. V., Hotta, C., Kuchroo, V. K., and Behar, S. M. (2010). Tim3 binding to galectin-9 stimulates antimicrobial immunity. The Journal of experimental medicine 207, 2343-2354.

Ji. Y. X., Huang, Z., Yang, X., Wang. X., Zhao, L. P., Wang, P. X., Zhang, X. J., Alves-Bezerra, M., Cai, L., Zhang, P., et al. (2018). The deubiquitinating enzyme cylindromatosis mitigates nonalcoholic steatohepatitis. Nature medicine 24, 213-223.

Jia, J., Abudu, Y. P., Claude-Taupin, A., Gu, Y., Kumar, S., Choi, S. W., Peters, R., Mudd, M. H., Allers, L., Salemi, M., et al. (2018). Galectins Control mTOR in Response to Endomembrane Damage. Molecular cell 70, 120-135 e128.

Jing, Y., Liu, W., Cao, H., Zhang, D., Yao, X., Zhang, S., Xia, H., Li, D., Wang, Y. C., Yan, J., et al. (2015). Hepatic p38alpha regulates gluconeogenesis by suppressing AMPK. Journal of hepatology 62, 1319-1327.

Johannes, L., Jacob, R., and Leffler, H. (2018). Galectins at a glance. Journal of cell science 131.

Jones, R. G., Plas, D. R., Kubek, S., Buzzai. M., Mu, J., Xu, Y., Bimbaum, M. J., and Thompson, C. B. (2005). AMP-activated protein kinase induces a p53-dependent metabolic checkpoint. Molecular cell 18, 283-293.

Jung, C. H., Jun, C. B., Ro, S. H., Kim, Y. M., Otto, N. M., Cao, J., Kundu, M., and Kim, D. H. (2009). ULK-Atg13-FIP200 complexes mediate mTOR signaling to the autophagy machinery. Mol Biol Cell 20, 1992-2003.

Junker, B. H., Klukas, C., and Schreiber, F. (2006). VANTED: a system for advanced data analysis and visualization in the context of biological networks. BMC bioinformatics 7, 109.

Khaminets, A., Heinrich, T., Mari, M., Grumati, P., Huebner, A. K., Akutsu, M., Liebmann, L., Stolz, A., Nietzsche, S., Koch, N., et al. (2015). Regulation of endoplasmic reticulum turnover by selective autophagy. Nature 522, 354-358.

Kim, J., Kim, Y. C., Fang, C., Russell, R. C., Kim, J. H., Fan, W., Liu, R., Zhong, Q., and Guan, K. L. (2013). Differential regulation of distinct Vps34 complexes by AMPK in nutrient stress and autophagy. Cell 152, 290-303.

Kim, J., Kundu, M., Viollet. B., and Guan, K. L. (2011). AMPK and mTOR regulate autophagy through direct phosphorylation of Ulk1. Nature cell biology 13, 132-141.

Kim. J., Lee, H. Y., Ahn, J., Hyun, M., Lee, I., Min, K. J., and You, Y. J. (2016). NHX-5, an Endosomal Na+/H+ Exchanger, Is Associated with Metformin Action. The Journal of biological chemistry 291, 18591-18599.

Kimmelman, A. C., and White, E. (2017). Autophagy and Tumor Metabolism. Cell metabolism 25, 1037-1043.

Kirkin, V., McEwan, D. G., Novak, I., and Dikic, I. (2009). A role for ubiquitin in selective autophagy. Molecular cell 34, 259-269.

Kopitz, J., Kisen, G. O., Gordon, P. B., Bohley, P., and Seglen, P. O. (1990). Nonselective autophagy of cytosolic enzymes by isolated rat hepatocytes. The Journal of cell biology 111, 941-953.

Lazarou, M., Sliter, D. A., Kane, L. A., Sarraf, S. A., Wang, C., Burman, J. L., Sideris, D. P., Fogel, A. I., and Youle, R. J. (2015). The ubiquitin kinase PINK1 recruits autophagy receptors to induce mitophagy. Nature 524, 309-314.

Le Guerroue, F., Eck, F., Jung, J., Starzetz, T., Mittelbronn, M., Kaulich, M., and Behrends, C. (2017). Autophagosomal Content Profiling Reveals an LC3C-Dependent Piecemeal Mitophagy Pathway. Molecular cell 68, 786-796 e786.

Lee, J. H., Koh, H., Kim. M., Kim, Y., Lee, S. Y., Karess, R. E., Lee, S. H., Shong, M., Kim, J. M., Kim, J., el al. (2007). Energy-dependent regulation of cell structure by AMP-activated protein kinase. Nature 447, 1017-1020.

Lee, Y. S., Kim, Y. S., Lee, S. Y., Kim, G. H., Kim, B. J., Lee, S. H., Lee, K. U., Kim, G. S., Kim, S. W., and Koh, J. M. (2010). AMP kinase acts as a negative regulator of RANKL in the differentiation of osteoclasts. Bone 47, 926-937.

Lei, C. Q., Wu, X., Zhong, X., Jiang. L., Zhong. B., and Shu. H. B. (2019). USP19 Inhibits TNF-alpha- and IL-1beta-Triggered NF-kappaB Activation by Deubiquitinating TAK1. Journal of immunology.

Levine, B., and Kroemer, G. (2019). Biological Functions of Autophagy Genes: A Disease Perspective. Cell 176, 11-42.

Li, L., Liu, T., Li. Y., Wu, C., Luo, K., Yin, Y., Chen. Y., Nowsheen, S., Wu. J., Lou, Z., el al. (2018). The deubiquitinase USP9X promotes tumor cell survival and confers chemoresistance through YAP1 stabilization. Oncogene 37, 2422-2431.

Li, M., Zhang, C. S., Zong, Y., Feng, J. W., Ma. T., Hu. M., Lin, Z., Li, X., Xie, C., Wu, Y., et al. (2019). Transient Receptor Potential V Channels Are Essential for Glucose Sensing by Aldolase and AMPK. Cell metabolism.

Li, Q., Yan, J., Mao, A. P., Li, C., Ran, Y., Shu, H. B., and Wang, Y. Y. (2011). Tripartite motif 8 (TRIM8) modulates TNFalpha- and IL-1beta-triggered NF-kappaB activation by targeting TAK1 for K63-linked polyubiquitination. Proceedings of the National Academy of Sciences of the United States of America 108, 19341-19346.

Lin, S. C., and Hardie. D. G. (2018). AMPK: Sensing Glucose as well as Cellular Energy Status. Cell metabolism 27, 299-313.

Liu, C. C., Lin, Y. C., Chen, Y. H., Chen, C. M., Pang, L. Y., Chen. H. A., Wu. P. R., Lin, M. Y, Jiang, S. T., Tsai, T. F., et al. (2016). Cul3-KLHL20 Ubiquitin Ligase Governs the Turnover of ULK1 and VPS34 Complexes to Control Autophagy Termination. Molecular cell 61, 84-97.

Liu, W., Jiang, Y., Sun, J., Geng, S., Pan, Z., Prinz, R. A., Wang, C., Sun, J., Jiao, X., and Xu, X. (2018). Activation of TGF-beta-activated kinase 1 (TAK1) restricts *Salmonella Typhimurium* growth by inducing AMPK activation and autophagy. Cell death & disease 9, 570.

Liu, Z., Lv, Y. J., Song, Y. P., Li, X. H., Du, Y. N., Wang, C. H., and Hu, L. K. (2012). Lysosomal membrane protein TMEM192 deficiency triggers crosstalk between autophagy and apoptosis in HepG2 hepatoma cells. Oncology reports 28, 985-991.

Lobingier, B. T., Huttenhain, R., Eichel, K., Miller, K. B., Ting, A. Y., von Zastrow, M., and Krogan. N. J. (2017). An Approach to Spatiotemporally Resolve Protein Interaction Networks in Living Cells. Cell 169, 350-360 e312.

Lu, M., Lin, S. C., Huang, Y., Kang, Y. J., Rich, R., Lo, Y. C., Myszka. D., Han, J., and Wu, H. (2007). XIAP induces NF-kappaB activation via the BIR1/TAB1 interaction and BIR1 dimerization. Molecular cell 26, 689-702.

Madeo, F., Carmona-Gutierrez, D., Hofer, S. J., and Kroemer, G. (2019). Caloric Restriction Mimetics against Age-Associated Disease: Targets, Mechanisms, and Therapeutic Potential. Cell metabolism 29, 592-610.

Maejima. I., Takahashi, A., Omori, H., Kimura, T., Takabatake, Y., Saitoh, T., Yamamoto, A., Hamasaki, M., Noda, T., Isaka, Y., et al. (2013). Autophagy sequesters damaged lysosomes to control lysosomal biogenesis and kidney injury. The EMBO journal 32, 2336-2347.

Manzanillo, P. S., Shiloh, M. U., Portnoy. D. A., and Cox, J. S. (2012). *Mycobacterium Tuberculosis* Activates the DNA-Dependent Cytosolic Surveillance Pathway within Macrophages. Cell host & microbe 11, 469-480.

Marcassa, E., Kallinos, A., Jardine, J., Rusilowicz-Jones, E. V., Martinez, A., Kuehl, S., Islinger. M., Clague, M. J., and Urbe, S. (2018). Dual role of USP30 in controlling basal pexophagy and mitophagy. EMBO reports 19.

Masters, S. L., Dunne, A., Subramanian, S. L., Hull, R. L., Tannahill, G. M., Sharp, F. A., Becker, C., Franchi, L., Yoshihara, E., Chen, Z., et al. (2010). Activation of the NLRP3 inflammasome by islet amyloid polypeptide provides a mechanism for enhanced IL-1beta in type 2 diabetes. Nature immunology 11, 897-904.

Matsushita. N., Nishi, N., Seki, M., Matsumoto, R., Kuwabara, I., Liu, F. T., Hata, Y., Nakamura, T., and Hirashima, M. (2000). Requirement of divalent galactoside-binding activity of ecalectin/galectin-9 for eosinophil chemoattraction. The Journal of biological chemistry 275, 8355-8360.

McCabe, M. T., Powell, D. R., Zhou, W., and Vertino, P. M. (2010). Homozygous deletion of the STK11/LKB1 locus and the generation of novel fusion transcripts in cervical cancer cells. Cancer genetics and cytogenetics 197, 130-141.

Min, Y., Lee, S., Kim, M. J., Chun, E., and Lee, K. Y. (2017). Ubiquitin-Specific Protease 14 Negatively Regulates Toll-Like Receptor 4-Mediated Signaling and Autophagy Induction by Inhibiting Ubiquitination of TAK1-Binding Protein 2 and Beclin 1. Frontiers in immunology 8, 1827.

Mizushima, N., Levine, B., Cuervo, A. M., and Klionsky, D. J. (2008). Autophagy fights disease through cellular self-digestion. Nature 451, 1069-1075.

Momcilovic, M., Hong, S. P., and Carlson, M. (2006). Mammalian TAK1 activates Snf1 protein kinase in yeast and phosphorylates AMP-activated protein kinase in vitro. The Journal of biological chemistry 281, 25336-25343.

Nazio, F., Strappazzon, F., Antonioli, M., Bielli, P., Cianfanelli, V., Bordi, M., Gretzmeier, C., Dengjel, J., Piacentini, M., Fimia. G. M., et al. (2013). mTOR inhibits autophagy by controlling ULK1 ubiquitylation, self-association and function through AMBRA1 and TRAF6. Nature cell biology 15, 406-416.

Neumann, D. (2018). Is TAK1 a Direct Upstream Kinase of AMPK? Int J Mol Sci 19.

Ninomiya-Tsuji, J., Kishimoto, K., Hiyama, A., Inoue, J., Cao. Z., and Matsumoto. K. (1999). The kinase TAK1 can activate the NIK-I kappaB as well as the MAP kinase cascade in the IL-1 signalling pathway. Nature 398, 252-256.

O'Neill, L. A., Kishton, R. J., and Rathmell, J. (2016). A guide to immunometabolism for immunologists. Nat Rev Immunol 16, 553-565.

Okada, M., Matsuzawa, A., Yoshimura. A., and Ichijo, H. (2014). The lysosome rupture-activated TAK1-JNK pathway regulates NLRP3 inflammasome activation. The Journal of biological chemistry 289, 32926-32936.

Papadopoulos, C., Kirchner, P., Bug, M., Grum, D., Koerver, L., Schulze. N., Poehler, R., Dressler, A., Fengler, S., Arhzaouy, K., et al. (2017). VCP/p97 cooperates with YOD1, UBXD1 and PLAA to drive clearance of ruptured lysosomes by autophagy. The EMBO journal 36, 135-150.

Pam, T. L., Melehani, J. H., Ranek, M. J., and Willis, M. S. (2015). Functional Amyloid Signaling via the Inflammasome, Necrosome, and Signalosome: New Therapeutic Targets in Heart Failure. Front Cardiovasc Med 2, 25.

Paudel, P., Zhang, Q., Leung, C., Greenberg, H. C., Guo, Y., Chem, Y. H., Dong, A., Li, Y., Vedadi, M., Zhuang, Z., et al. (2019). Crystal structure and activity-based labeling reveal the mechanisms for linkage-specific substrate recognition by deubiquitinase USP9X. Proceedings of the National Academy of Sciences of the United States of America 116, 7288-7297.

Paz, I., Sachse, M., Dupont, N., Mounier, J., Cederfur, C., Enninga. J., Leffler, H., Poirier, F., Prevost. M. C., Lafont, F., et al. (2010). Galectin-3, a marker for vacuole lysis by invasive pathogens. Cell Microbiol 12, 530-544.

Pertel, T., Hausmann, S., Morger, D., Zuger, S., Guerra, J., Lascano, J., Reinhard, C., Santoni, F. A., Uchil, P. D., Chatel, L., et al. (2011). TRIM5 is an innate immune sensor for the retrovirus capsid lattice. Nature 472, 361-365.

Pineda, C. T., Ramanathan, S., Fon Tacer, K., Weon, J. L., Potts, M. B., Ou, Y. H., White, M. A., and Potts, P. R. (2015). Degradation of AMPK by a Cancer-Specific Ubiquitin Ligase. Cell 160, 715-728.

Pozhidaeva, A., and Bezsonova, 1. (2019). USP7: Structure, substrate specificity, and inhibition. DNA repair 76, 30-39.

Rabinowitz, J. D., and White, E. (2010). Autophagy and metabolism. Science 330, 1344-1348.

Radulovic, M., Schink, K. O., Wenzel, E. M., Nahse, V., Bongiovanni, A., Lafont, F., and Stenmark, H. (2018). ESCRT-mediated lysosome repair precedes lysophagy and promotes cell survival. The EMBO journal 37.

Rajani, R., Pastor-Soler, N. M., and Hallows, K. R. (2017). Role of AMP-activated protein kinase in kidney tubular transport, metabolism, and disease. Curr Opin Nephrol Hypertens 26, 375-383.

Rambold, A. S., Cohen, S., and Lippincott-Schwartz, J. (2015). Fatty acid trafficking in starved cells: regulation by lipid droplet lipolysis, autophagy, and mitochondrial fusion dynamics. Developmental cell 32, 678-692.

Randow, F., and Youle, R. J. (2014). Self and nonself: how autophagy targets mitochondria and bacteria. Cell Host Microbe 15, 403-411.

Razani, B., Feng, C., Coleman, T., Emanuel, R., Wen. H., Hwang, S., Ting, J. P., Virgin, H. W., Kastan, M. B., and Semenkovich, C. F. (2012). Autophagy links inflammasomes to atherosclerotic progression. Cell metabolism 15, 534-544.

Reiley, W. W., Jin, W., Lee, A. J., Wright, A., Wu, X., Tewalt, E. F., Leonard, T. O., Norbury, C. C., Fitzpatrick, L., Zhang, M., et al. (2007). Deubiquitinating enzyme CYLD negatively regulates the ubiquitin-dependent kinase Tak1 and prevents abnormal T cell responses. The Journal of experimental medicine 204, 1475-1485.

Rivera, J. F., Costes, S., Gurlo, T., Glabe. C. G., and Butler, P. C. (2014). Autophagy defends pancreatic beta cells from human islet amyloid polypeptide-induced toxicity. The Journal of clinical investigation 124, 3489-3500.

Rogov. V., Dotsch, V., Johansen, T., and Kirkin, V. (2014). Interactions between autophagy receptors and ubiquitin-like proteins form the molecular basis for selective autophagy. Molecular cell 53, 167-178.

Rubinsztein, D. C., Bento, C. F., and Deretic, V. (2015). Therapeutic targeting of autophagy in neurodegenerative and infectious diseases. The Journal of experimental medicine 212, 979-990.

Sakurai, H., Suzuki, S., Kawasaki, N., Nakano, H., Okazaki, T., Chino, A., Doi, T., and Saiki, I. (2003). Tumor necrosis factor-alpha-induced IKK phosphorylation of NF-kappaB p65 on serine 536 is mediated through the TRAF2, TRAF5, and TAK1 signaling pathway. The Journal of biological chemistry 278, 36916-36923.

Sardiello, M., Palmieri, M., di Ronza, A., Medina, D. L., Valenza, M., Gennarino, V. A., Di Malta, C., Donaudy. F., Embrione, V., Polishchuk, R. S., et al. (2009). A gene network regulating lysosomal biogenesis and function. Science 325, 473-477.

Saxton, R. A., and Sabatini, D. M. (2017). mTOR Signaling in Growth, Metabolism, and Disease. Cell 168, %0-976.

Schroder, K., and Tschopp, J. (2010). The inflammasomes. Cell 140, 821-832.

Schwickart, M., Huang, X., Lill, J. R., Liu, J., Ferrando, R., French, D. M., Maecker, H., O'Rourke, K., Bazan, F., Eastham-Anderson, J., et al. (2010). Deubiquitinase USP9X stabilizes MCL1 and promotes tumour cell survival. Nature 463, 103-107.

Seglen, P. O., Gordon. P. B., and Holen, 1. (1990). Nonselective autophagy. Semin Cell Biol 1, 441-448.

Seo, A. Y., Lau, P. W., Feliciano, D., Sengupta, P., Gros, M. A. L., Cinquin, B., Larabell, C. A., and Lippincott-Schwartz., J. (2017). AMPK and vacuole-associated Atg14p orchestrate mu-lipophagy for energy production and long-term survival under glucose starvation. eLife 6.

Settembre, C., De Cegli, R., Mansueto, G., Saha, P. K., Vetrini, F., Visvikis, O., Huynh, T., Carissimo, A., Palmer, D., Jurgen Klisch, T., et al. (2013). TFEB controls cellular lipid metabolism through a starvation-induced autoregulatory loop. Nature cell biology 15, 647-658.

Settembre, C., Di Malta. C., Polito, V. A., Garcia Arencibia. M., Vetrini, F., Erdin, S., Erdin, S. U., Huynh, T., Medina. D., Colella, P., et al. (2011). TFEB links autophagy to lysosomal biogenesis. Science 332, 1429-1433.

Singh, R, Kaushik, S., Wang, Y., Xiang, Y., Novak, I., Komatsu, M., Tanaka. K., Cuervo, A. M., and Czaja, M. J. (2009). Autophagy regulates lipid metabolism. Nature 458, 1131-1135.

Singhirunnusorn, P., Suzuki, S., Kawasaki, N., Saiki, I., and Sakurai. H. (2005). Critical roles of threonine 187 phosphorylation in cellular stress-induced rapid and transient activation of transforming growth factor-beta-activated kinase 1 (TAK1) in a signaling complex containing TAK1-binding protein TAB1 and TAB2. The Journal of biological chemistry 280, 7359-7368.

Skowyra. M. L., Schlesinger, P. H., Naismith, T. V., and Hanson, P. I. (2018). Triggered recruitment of ESCRT machinery promotes endolysosomal repair. Science 360.

Soga, T., and Heiger, D. N. (2000). Amino acid analysis by capillary electrophoresis electrospray ionization mass spectrometry. Analytical chemistry 72, 1236-1241.

Soga, T., Ohashi, Y., Ueno, Y., Naraoka, H., Tomita, M., and Nishioka, T. (2003). Quantitative metabolome analysis using capillary electrophoresis mass spectrometry. Journal of proteome research 2, 488-494.

Soga, T., Ueno, Y., Naraoka, H., Ohashi, Y., Tomita, M., and Nishioka, T. (2002). Simultaneous determination of anionic intermediates for *Bacillus subtilis* metabolic pathways by capillary electrophoresis electrospray ionization mass spectrometry. Analytical chemistry 74, 2233-2239.

Sorrentino, A., Thakur, N., Grimsby, S., Marcusson, A., von Bulow, V., Schuster, N., Zhang, S., Heldin, C. H., and Landstrom, M. (2008). The type I TGF-beta receptor engages TRAF6 to activate TAK1 in a receptor kinase-independent manner. Nature cell biology 10, 1199-1207.

Strickson, S., Emmerich, C. H., Goh, E. T. H., Zhang. J., Kelsall, I. R., Macartney, T., Hastie, C. J., Knebel, A., Peggie, M., Marchesi, F., et al. (2017). Roles of the TRAF6 and Pellino E3 ligases in MyD88 and RANKL signaling. Proceedings of the National Academy of Sciences of the United States of America 114, E3481-E3489.

Sugimoto, M., Wong, D. T., Hirayama, A., Soga, T., and Tomita, M. (2010). Capillary electrophoresis mass spectrometry-based saliva metabolomics identified oral, breast and pancreatic cancer-specific profiles. Metabolomics: Official journal of the Metabolomic Society 6, 78-95.

Takaesu, G., Kobayashi, T., and Yoshimura, A. (2012). TGFbeta-activated kinase 1 (TAK1)-binding proteins (TAB) 2 and 3 negatively regulate autophagy. Journal of biochemistry 151, 157-166.

Thiele, D. L., and Lipsky, P. E. (1990). Mechanism of L-leucyl-L-leucine methyl ester-mediated killing of cytotoxic lymphocytes: dependence on a lysosomal thiol protease, dipeptidyl peptidase I, that is enriched in these cells. Proceedings of the National Academy of Sciences of the United States of America 87, 83-87.

Thurston, T. L., Wandel, M. P., von Muhlinen, N., Foeglein, A., and Randow, F. (2012). Galectin 8 targets damaged vesicles for autophagy to defend cells against bacterial invasion. Nature 482, 414-418.

Tyanova, S., Temu, T., Sinitcyn, P., Carlson, A., Hein, M. Y., Geiger, T., Mann, M., and Cox, J. (2016). The Perseus computational platform for comprehensive analysis of (prote)omics data. Nature methods 13, 731-740.

Wang, C., Deng, L., Hong, M., Akkaraju, G. R., Inoue, J., and Chen, Z. J. (2001). TAK1 is a ubiquitin-dependent kinase of MKK and IKK. Nature 412, 346-351.

Wang, Y., Shan, B., Liang, Y., Wei, H., and Yuan, J. (2018). Parkin regulates NF-kappaB by mediating site-specific ubiquitination of RIPK1. Cell death & disease 9, 732.

Werneburg, N. W., Guicciardi, M. E., Bronk, S. F., Kaufmann, S. H., and Gores, G. J. (2007). Tumor necrosis factor-related apoptosis-inducing ligand activates a lysosomal pathway of apoptosis that is regulated by Bcl-2 proteins. The Journal of biological chemistry 282, 28960-28970.

Woods, A., Johnstone. S. R., Dickerson, K., Leiper, F. C., Fryer, L. G., Neumann, D., Schlattner, U., Wallimann. T., Carlson, M., and Carling, D. (2003). LKB1 is the upstream kinase in the AMP-activated protein kinase cascade. Current biology: CB 13, 2004-2008.

Wu, J., Powell, F., Larsen, N. A., Lai, Z., Byth, K. F., Read, J., Gu, R. F., Roth, M., Toader, D., Saeh, J. C., et al. (2013). Mechanism and in vitro pharmacology of TAK1 inhibition by (5Z)-7-Oxozeaenol. ACS chemical biology 8, 643-650.

Wyant, G. A., Abu-Remaileh, M., Frenkel, E. M., Laqtom, N. N., Dharamdasani, V., Lewis, C. A., Chan, S. H., Heinze, I., Ori, A., and Sabatini. D. M. (2018). NUFIP1 is a ribosome receptor for starvation-induced ribophagy. Science 360, 751-758.

Xie, M., Zhang, D., Dyck, J. R., Li, Y., Zhang, H., Morishima. M., Mann, D. L., Taffet, G. E., Baldini, A., Khourv, D. S., et al. (2006). A pivotal role for endogenous TGF-beta-activated kinase-1 in the LKB1/AMP-activated protein kinase energy-sensor pathway. Proceedings of the National Academy of Sciences of the United States of America 103, 17378-17383.

Yang, Z., Xian, H., Hu, J., Tian, S., Qin, Y., Wang, R. F., and Cui, J. (2015). USP18 negatively regulates NF-kappaB signaling by targeting TAK1 and NEMO for deubiquitination through distinct mechanisms. Scientific reports 5, 12738.

Yoshida, Y., Yasuda, S., Fujita, T., Hamasaki, M., Murakami, A., Kawawaki, J., Iwai, K., Saeki, Y., Yoshimori, T., Matsuda, N., et al. (2017). Ubiquitination of exposed glycoproteins by SCF(FBXO27) directs damaged lysosomes for autophagy. Proceedings of the National Academy of Sciences of the United States of America 114, 8574-8579.

Yu, L., McPhee, C. K., Zheng, L., Mardones, G. A., Rong, Y., Peng, J., Mi, N., Zhao, Y., Liu, Z., Wan, F., et al. (2010). Termination of autophagy and reformation of lysosomes regulated by mTOR. Nature 465, 942-946.

Yu, Y., Ge, N., Xie, M., Sun, W., Burlingame, S., Pass, A. K., Nuchtem, J. G., Zhang, D., Fu, S., Schneider, M. D., et al. (2008). Phosphorylation of Thr-178 and Thr-184 in the TAK1 T-loop is required for interleukin (IL)-1-mediated optimal NFkappaB and AP-1 activation as well as IL-6 gene expression. The Journal of biological chemistry 283, 24497-24505.

Zhang, C. S., Hawley, S. A., Zong, Y., Li, M., Wang, Z., Gray, A., Ma, T., Cui, J., Feng, J. W., Zhu, M., et al. (2017). Fructose-1,6-bisphosphate and aldolase mediate glucose sensing by AMPK. Nature 548, 112-116.

Zhang, C. S., Jiang, B., Li, M., Zhu, M., Peng, Y., Zhang, Y. L., Wu, Y. Q., Li, T. Y., Liang, Y., Lu, Z., et al. (2014). The lysosomal v-ATPase-Ragulator complex is a common activator for AMPK and mTORC1, acting as a switch between catabolism and anabolism. Cell metabolism 20, 526-540.

Zhang, C. S., Li, M., Ma, T., Zong, Y., Cui, J., Feng, J. W., Wu, Y. Q., Lin, S. Y., and Lin, S. C. (2016). Metformin Activates AMPK through the Lysosomal Pathway. Cell metabolism 24, 521-522.

Zhang, Y., Sowers, J. R., and Ren, J. (2018). Targeting autophagy in obesity: from pathophysiology to management. Nat Rev Endocrinol 14, 356-376.

Zhang, Y. L., Guo, H., Zhang, C. S., Lin. S. Y., Yin, Z., Peng, Y., Luo, H., Shi, Y., Lian, G., Zhang, C., et al. (2013). AMP as a low-energy charge signal autonomously initiates assembly of AXIN-AMPK-LKB1 complex for AMPK activation. Cell metabolism 18, 546-555.

Zhou, G., Myers, R., Li, Y., Chen, Y., Shen, X., Fenyk-Melody, J., Wu, M., Ventre, J., Doebber, T., Fujii, N., et al. (2001). Role of AMP-activated protein kinase in mechanism of metformin action. The Journal of clinical investigation 108, 1167-1174.

Zhu, C., Anderson, A. C., Schubart, A., Xiong, H., Imitola, J., Khoury, S. J., Zheng, X. X., Strom, T. B., and Kuchroo, V. K. (2005). The Tim-3 ligand galectin-9 negatively regulates T helper type 1 immunity. Nature immunology 6, 1245-1252.

Zippel, N., Malik, R. A., Fromel, T., Popp, R., Bess, E., Strilic, B., Wettschureck, N., Fleming, I., and Fisslthaler, B. (2013). Transforming growth factor-beta-activated kinase 1 regulates angiogenesis via AMP-activated protein kinase-alpha1 and redox balance in endothelial cells. Arteriosclerosis, thrombosis, and vascular biology 33, 2792-2799.

Zirin, J., Nieuwenhuis, J., and Perrimon, N. (2013). Role of autophagy in glycogen breakdown and its relevance to chloroquine myopathy. PLoS biology 11, e1001708.

The invention claimed is:

1. A method of treating a tuberculosis infection in a subject in need comprising administering to said subject a combination of an effective amount of metformin or its pharmaceutically acceptable salt and at least one lysosomotropic agent selected from the group consisting of O-methyl-serinedodecyl amide (MSDA), (2-(1-ethyl-6-fluoro-4-oxo-7-(piperazin-1-yl)-1,4-dihydro-1,8-naphthyridin-3-yl)-1H-benzo[d]imidazole-6-carbonitril (LZ-106), siramesine, sphingosine, N-dodecylimidazole, L-leucyl-L-leucine methyl ester (LLOMe) or a pharmaceutically acceptable salt thereof.

2. The method according to claim 1 wherein said lysosomotropic agent is MSDA, LLOMe or a pharmaceutically acceptable salt or mixture there.

3. The method according to claim 1 wherein said lysosomotropic agent is MSDA or a pharmaceutically acceptable salt thereof.

* * * * *